(12) United States Patent
Woloszko et al.

(10) Patent No.: US 7,824,405 B2
(45) Date of Patent: *Nov. 2, 2010

(54) ELECTROSURGICAL APPARATUS AND METHODS FOR LAPAROSCOPY

(75) Inventors: Jean Woloszko, Austin, TX (US); Maria B. Ellsberry, Fremont, CA (US)

(73) Assignee: ArthroCare Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/031,771

(22) Filed: Feb. 15, 2008

(65) Prior Publication Data

US 2008/0132890 A1 Jun. 5, 2008

Related U.S. Application Data

(60) Division of application No. 10/365,759, filed on Feb. 14, 2003, now Pat. No. 7,331,957, which is a continuation-in-part of application No. 09/766,168, filed on Jan. 19, 2001, now Pat. No. 6,589,237, and a continuation-in-part of application No. 09/197,013, filed on Nov. 20, 1998, now Pat. No. 6,296,638, which is a continuation-in-part of application No. 09/010,382, filed on Jan. 21, 1998, now Pat. No. 6,190,381, which is a continuation-in-part of application No. 08/990,374, filed on Dec. 15, 1997, now Pat. No. 6,109,268, which is a continuation-in-part of application No. 08/485,219, filed on Jun. 7, 1995, now Pat. No. 5,697,281, which is a continuation-in-part of application No. 08/446,767, filed as application No. PCT/US94/05168 on May 10, 1994, now Pat. No. 5,697,909, which is a continuation-in-part of application No. 08/059,681, filed on May 10, 1993, now abandoned, which is a continuation-in-part of application No. 07/958,977, filed on Oct. 9, 1992, now Pat. No. 5,366,443, which is a continuation-in-part of application No. 07/817,575, filed on Jan. 7, 1992, now abandoned.

(60) Provisional application No. 60/233,345, filed on Sep. 18, 2000, provisional application No. 60/210,567, filed on Jun. 9, 2000.

(51) Int. Cl.
*A61B 18/14* (2006.01)

(52) U.S. Cl. .............. 606/41; 606/45; 606/46; 606/48; 606/50; 604/35; 607/99

(58) Field of Classification Search .......... 606/41, 606/45, 46, 48–50
See application file for complete search history.

(56) References Cited

U.S. PATENT DOCUMENTS 2,056,377 A 10/1939 Wappler ................ 125/303

(Continued)

FOREIGN PATENT DOCUMENTS

DE 3930451 A1 3/1991

(Continued)

OTHER PUBLICATIONS

BiLAP IFU 910033-002 Rev A for BiLAP Model 3527, L-Hook; BiLAP Model 3525, J-Hook; BiLAP Model 3529, High Angle, 2 pgs., Nov. 30, 1993.

(Continued)

*Primary Examiner*—Lee S Cohen
(74) *Attorney, Agent, or Firm*—Matthew Scheele; Brian Szymczak

(57) ABSTRACT

Electrosurgical methods and apparatus for treating tissue at a target site of a patient. An electrosurgical instrument includes a shaft, having a shaft distal end and a shaft proximal end, and an electrode assembly disposed at the shaft distal end. The electrode assembly includes at least one active electrode disposed on an electrode support. The instrument is adapted for coupling to a high frequency power supply or electrosurgical generator. Each active electrode is adapted for removing tissue from a target site and/or for localized coagulation of the target tissue. In one embodiment, the instrument is adapted for laparoscopic procedures.

23 Claims, 35 Drawing Sheets

U.S. PATENT DOCUMENTS

| | | | |
|---|---|---|---|
| 3,633,425 A | 1/1972 | Sanford | 73/356 |
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,248,231 A | 2/1981 | Herczog et al. | 128/303 |
| 4,326,529 A | 4/1982 | Doss et al. | 128/303 |
| 4,381,007 A | 4/1983 | Doss | 128/303 |
| 4,474,179 A | 10/1984 | Koch | 606/40 |
| 4,476,862 A | 10/1984 | Pao | 128/303 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,590,934 A | 5/1986 | Malis et al. | 128/303 |
| 4,593,691 A | 6/1986 | Lindstrom et al. | 128/303 |
| 4,632,109 A | 12/1986 | Paterson | 606/39 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,727,874 A | 3/1988 | Bowers et al. | 128/303 |
| 4,765,331 A | 8/1988 | Petruzzi et al. | 128/303 |
| 4,785,807 A | 11/1988 | Blancch | 606/45 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,078,717 A | 1/1992 | Parins et al. | 606/48 |
| 5,080,660 A | 1/1992 | Buelna | 606/45 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble et al. | 128/422 |
| 5,100,402 A | 3/1992 | Fan | 606/41 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,190,541 A | 3/1993 | Abele et al. | 606/46 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,197,964 A | 3/1993 | Parins | 606/48 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,217,460 A | 6/1993 | Knoepfler | 606/52 |
| 5,246,440 A | 9/1993 | Vannoord | 606/39 |
| 5,261,410 A | 11/1993 | Alfano et al. | 600/475 |
| 5,261,905 A | 11/1993 | Doresey | 606/45 |
| 5,267,994 A | 12/1993 | Gentelia et al. | 606/15 |
| 5,267,997 A | 12/1993 | Farin et al. | 606/38 |
| 5,267,998 A | 12/1993 | Hagen | 606/45 |
| 5,269,780 A | 12/1993 | Roos | 606/42 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,282,799 A | 2/1994 | Rydell | 606/48 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,336,443 A | 8/1994 | Eggers | 252/511 |
| 5,342,357 A | 8/1994 | Nardella | 606/40 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita et al. | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,431,649 A | 7/1995 | Mulier et al. | 606/41 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,451,224 A | 9/1995 | Goble et al. | 606/48 |
| 5,454,809 A | 10/1995 | Janssen | 606/41 |
| 5,472,443 A | 12/1995 | Cordis et al. | 606/48 |
| 5,490,850 A | 2/1996 | Ellman et al. | 606/45 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,514,130 A | 5/1996 | Baker | 606/41 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,584,872 A | 12/1996 | LaFontaine et al. | 607/117 |
| 5,609,151 A | 3/1997 | Mulier et al. | 128/642 |
| 5,633,578 A | 5/1997 | Eggers et al. | 323/301 |
| 5,647,869 A | 7/1997 | Goble et al. | 606/37 |

| Patent | Kind | Date | Inventor | Class |
|---|---|---|---|---|
| 5,662,680 | A | 9/1997 | Desai | 606/210 |
| 5,676,693 | A | 10/1997 | LaFontaine et al. | 607/116 |
| 5,681,282 | A | 10/1997 | Eggers et al. | 604/114 |
| 5,683,366 | A | 11/1997 | Eggers et al. | 604/114 |
| 5,697,281 | A | 12/1997 | Eggers et al. | 604/114 |
| 5,697,536 | A | 12/1997 | Eggers et al. | 604/114 |
| 5,697,882 | A | 12/1997 | Eggers et al. | 604/114 |
| 5,697,909 | A | 12/1997 | Eggers et al. | 604/114 |
| 5,700,262 | A | 12/1997 | Acosta et al. | 606/48 |
| 5,702,390 | A | 12/1997 | Austin et al. | 606/48 |
| 5,725,524 | A | 3/1998 | Mulier et al. | 606/41 |
| 5,733,283 | A | 3/1998 | Malis et al. | 606/48 |
| 5,746,746 | A | 5/1998 | Garito et al. | 606/41 |
| 5,766,153 | A | 6/1998 | Eggers et al. | 604/114 |
| 5,807,392 | A | 9/1998 | Eggers | 606/31 |
| 5,807,395 | A | 9/1998 | Mulier et al. | 606/41 |
| 5,810,764 | A | 9/1998 | Eggers et al. | 604/23 |
| 5,810,809 | A | 9/1998 | Rydell | 606/49 |
| 5,836,875 | A | 11/1998 | Webster, Jr. | 600/374 |
| 5,843,019 | A | 12/1998 | Eggers et al. | 604/22 |
| 5,860,951 | A | 1/1999 | Eggers | 604/510 |
| 5,860,974 | A | 1/1999 | Abele | 606/41 |
| 5,860,975 | A | 1/1999 | Goble et al. | 606/45 |
| 5,871,469 | A | 2/1999 | Eggers et al. | 604/114 |
| 5,873,855 | A | 2/1999 | Eggers et al. | 604/114 |
| 5,885,277 | A | 3/1999 | Korth | 606/35 |
| 5,888,198 | A | 3/1999 | Eggers et al. | 604/114 |
| 5,891,095 | A | 4/1999 | Eggers et al. | 604/114 |
| 5,891,134 | A | 4/1999 | Goble et al. | 606/27 |
| 5,893,849 | A | 4/1999 | Weaver | 606/41 |
| 5,897,553 | A | 4/1999 | Mulier et al. | 606/41 |
| 5,902,272 | A | 5/1999 | Eggers et al. | 604/114 |
| 5,944,715 | A | 8/1999 | Goble et al. | 606/41 |
| 5,954,716 | A | 9/1999 | Sharkey et al. | 606/32 |
| 6,004,319 | A | 12/1999 | Goble et al. | 606/48 |
| 6,013,076 | A | 1/2000 | Goble et al. | 606/41 |
| 6,015,406 | A | 1/2000 | Goble et al. | 606/41 |
| 6,024,733 | A | 2/2000 | Eggers et al. | 604/500 |
| 6,027,501 | A | 2/2000 | Goble et al. | 606/41 |
| 6,039,734 | A | 3/2000 | Goble et al. | 606/41 |
| 6,047,700 | A | 4/2000 | Eggers et al. | 128/898 |
| 6,056,746 | A | 5/2000 | Goble et al. | 606/48 |
| 6,063,079 | A | 5/2000 | Hovda et al. | 606/41 |
| 6,063,083 | A | 5/2000 | Duong-Yan | 606/45 |
| 6,066,134 | A | 5/2000 | Eggers et al. | 606/32 |
| 6,066,137 | A | 5/2000 | Greep | 606/45 |
| 6,068,628 | A | 5/2000 | Fanton et al. | 606/41 |
| 6,074,386 | A | 6/2000 | Goble et al. | 606/34 |
| 6,090,106 | A | 7/2000 | Goble et al. | 606/41 |
| 6,093,186 | A | 7/2000 | Goble et al. | 606/34 |
| 6,096,037 | A | 8/2000 | Mulier et al. | 606/49 |
| 6,102,046 | A | 8/2000 | Weinstein et al. | 128/898 |
| 6,105,581 | A | 8/2000 | Eggers et al. | 128/898 |
| 6,109,268 | A | 8/2000 | Thapliyal et al. | 128/898 |
| 6,117,109 | A | 9/2000 | Eggers et al. | 604/114 |
| 6,126,658 | A | 10/2000 | Baker | 606/51 |
| 6,126,682 | A | 10/2000 | Sharkey et al. | 607/96 |
| 6,142,992 | A | 11/2000 | Cheng et al. | 606/34 |
| 6,149,620 | A | 11/2000 | Baker et al. | 604/22 |
| 6,159,194 | A | 12/2000 | Eggers et al. | 604/500 |
| 6,159,208 | A | 12/2000 | Hovda et al. | 606/41 |
| 6,168,593 | B1 | 1/2001 | Sharkey et al. | 606/34 |
| 6,174,309 | B1 | 1/2001 | Wrublewski et al. | 606/45 |
| 6,179,824 | B1 | 1/2001 | Eggers et al. | 604/500 |
| 6,179,836 | B1 | 1/2001 | Eggers et al. | 606/45 |
| 6,183,469 | B1 | 2/2001 | Thapliyal et al. | 606/41 |
| 6,190,381 | B1 | 2/2001 | Olsen et al. | 606/32 |
| 6,203,542 | B1 | 3/2001 | Ellsberry et al. | 606/41 |
| 6,210,402 | B1 | 4/2001 | Olsen et al. | 606/32 |
| 6,214,001 | B1 | 4/2001 | Casscells et al. | 606/41 |
| 6,217,575 | B1 | 4/2001 | DeVore et al. | 606/41 |
| 6,224,592 | B1 | 5/2001 | Eggers et al. | 606/32 |
| 6,228,078 | B1 | 5/2001 | Eggers et al. | 606/32 |
| 6,228,081 | B1 | 5/2001 | Goble | 606/34 |
| 6,234,178 | B1 | 5/2001 | Eggers | 606/32 |
| 6,235,020 | B1 | 5/2001 | Cheng et al. | 606/34 |
| 6,237,604 | B1 | 5/2001 | Burnside et al. | 128/897 |
| 6,238,391 | B1 | 5/2001 | Olsen et al. | 606/41 |
| 6,254,600 | B1 | 7/2001 | Willink et al. | 606/41 |
| 6,261,286 | B1 | 7/2001 | Goble et al. | 606/34 |
| 6,261,311 | B1 | 7/2001 | Sharkey et al. | 607/96 |
| 6,264,652 | B1 | 7/2001 | Eggers et al. | 606/41 |
| 6,270,460 | B1 | 8/2001 | McCartan et al. | 600/459 |
| 6,273,887 | B1 | 8/2001 | Yamauchi et al. | 606/48 |
| 6,277,112 | B1 | 8/2001 | Underwood et al. | 606/32 |
| 6,280,441 | B1 | 8/2001 | Ryan | 606/45 |
| 6,293,942 | B1 | 9/2001 | Goble et al. | 606/38 |
| 6,296,636 | B1 | 10/2001 | Cheng et al. | 606/32 |
| 6,296,638 | B1 | 10/2001 | Davison et al. | 606/41 |
| 6,306,134 | B1 | 10/2001 | Goble et al. | 606/42 |
| 6,308,089 | B1 | 10/2001 | von der Ruhr et al. | 600/338 |
| 6,309,387 | B1 | 10/2001 | Eggers et al. | 606/41 |
| 6,312,408 | B1 | 11/2001 | Eggers et al. | 604/114 |
| 6,322,549 | B1 | 11/2001 | Eggers et al. | 604/500 |
| 6,355,032 | B1 | 3/2002 | Hovda et al. | 606/32 |
| 6,363,937 | B1 | 4/2002 | Hovda et al. | 128/898 |
| 6,364,877 | B1 | 4/2002 | Goble et al. | 606/34 |
| 6,379,350 | B1 | 4/2002 | Sharkey et al. | 606/41 |
| 6,379,351 | B1 | 4/2002 | Thapliyal et al. | 606/41 |
| 6,391,025 | B1 | 5/2002 | Weinstein et al. | 606/41 |
| 6,416,507 | B1 | 7/2002 | Eggers et al. | 606/32 |
| 6,416,508 | B1 | 7/2002 | Eggers et al. | 606/32 |
| 6,416,509 | B1 | 7/2002 | Goble et al. | 606/37 |
| 6,427,089 | B1 | 7/2002 | Knowlton | 607/101 |
| 6,432,103 | B1 | 8/2002 | Ellsberry et al. | 606/41 |
| 6,468,274 | B1 | 10/2002 | Alleyne et al. | 606/32 |
| 6,468,275 | B1 | 10/2002 | Wampler et al. | 606/48 |
| 6,482,201 | B1 | 11/2002 | Olsen et al. | 606/41 |
| 6,488,679 | B1 | 12/2002 | Swanson et al. | 606/40 |
| 6,517,498 | B1 | 2/2003 | Burbank et al. | 600/564 |
| 6,530,922 | B2 | 3/2003 | Cosman | 606/34 |
| 6,558,385 | B1 | 5/2003 | McClurken et al. | 606/50 |
| 6,578,579 | B2 | 6/2003 | Burnside | 128/897 |
| 6,589,237 | B2 | 7/2003 | Woloszko et al. | 606/41 |
| 6,602,248 | B1 | 8/2003 | Sharps et al. | 606/32 |
| 6,620,156 | B1 | 9/2003 | Garito et al. | 606/50 |
| 6,632,193 | B1 | 10/2003 | Davison et al. | 604/22 |
| 6,632,220 | B1 | 10/2003 | Eggers et al. | 606/41 |
| 6,749,604 | B1 | 6/2004 | Eggers et al. | 606/41 |
| 6,749,608 | B2 | 6/2004 | Garito et al. | 606/45 |
| 6,770,071 | B2 | 8/2004 | Woloszko et al. | 606/41 |
| 6,780,178 | B2 | 8/2004 | Palanker et al. | 600/41 |
| 6,780,180 | B1 | 8/2004 | Goble et al. | 606/41 |
| 6,790,217 | B2 | 9/2004 | Schulze et al. | 606/171 |
| 6,802,842 | B2 | 10/2004 | Ellman et al. | 606/45 |
| 6,808,525 | B2 | 10/2004 | Latterell et al. | 606/42 |
| 6,837,887 | B2 | 1/2005 | Woloszko et al. | 606/41 |
| 6,837,888 | B2 | 1/2005 | Ciarrocca et al. | 606/41 |
| 6,852,112 | B2 | 2/2005 | Platt | 606/49 |
| 6,920,883 | B2 | 7/2005 | Bessette et al. | 128/898 |
| 6,929,640 | B1 | 8/2005 | Underwood et al. | 606/32 |
| 6,949,096 | B2 | 9/2005 | Davison et al. | 606/41 |
| 6,960,204 | B2 | 11/2005 | Eggers et al. | 606/32 |
| 6,974,453 | B2 | 12/2005 | Woloszko et al. | 606/41 |
| 6,984,231 | B2 | 1/2006 | Goble et al. | 606/37 |
| 6,991,631 | B2 | 1/2006 | Woloszko et al. | 606/41 |
| 7,004,941 | B2 | 2/2006 | Tvinnereim et al. | 606/41 |
| 7,041,102 | B2 | 5/2006 | Truckai et al. | 606/51 |
| 7,070,596 | B1 | 7/2006 | Woloszko et al. | 606/41 |
| 7,090,672 | B2 | 8/2006 | Underwood et al. | 606/41 |
| 7,094,215 | B2 | 8/2006 | Davison et al. | 604/22 |
| 7,104,986 | B2 | 9/2006 | Hovda et al. | 606/32 |
| 7,128,742 | B2 | 10/2006 | Ohyama et al. | 606/34 |
| 7,131,969 | B1 | 11/2006 | Hovda et al. | 606/45 |
| 7,169,143 | B2 | 1/2007 | Eggers et al. | 606/32 |
| 7,179,255 | B2 | 2/2007 | Lettice et al. | 606/32 |

| | | | |
|---|---|---|---|
| 7,186,234 B2 | 3/2007 | Dahla et al. ............... 604/22 |
| 7,192,428 B2 | 3/2007 | Eggers et al. ............. 606/41 |
| 7,201,750 B1 | 4/2007 | Eggers et al. ............. 606/41 |
| 7,217,268 B2 | 5/2007 | Eggers et al. ............. 606/32 |
| 7,241,293 B2 | 7/2007 | Davison ...................... 600/410 |
| 7,270,658 B2 | 9/2007 | Woloszko et al. ......... 606/32 |
| 7,270,659 B2 | 9/2007 | Hovda et al. .............. 606/32 |
| 7,270,661 B2 | 9/2007 | Dahla et al. ............... 606/41 |
| 7,276,063 B2 | 10/2007 | Davison et al. ........... 606/45 |
| 7,297,143 B2 | 11/2007 | Woloszko et al. ......... 606/41 |
| 7,297,145 B2 | 11/2007 | Woloszko et al. ......... 606/41 |
| 7,318,823 B2 | 1/2008 | Sharps et al. .............. 606/32 |
| 7,331,956 B2 | 2/2008 | Hovda et al. .............. 606/32 |
| 7,331,957 B2 * | 2/2008 | Woloszko et al. ......... 606/41 |
| RE40,156 E | 3/2008 | Sharps et al. .............. 606/32 |
| 7,357,798 B2 | 4/2008 | Sharps et al. .............. 606/32 |
| 7,387,625 B2 | 6/2008 | Hovda et al. .............. 606/32 |
| 7,419,488 B2 | 9/2008 | Ciarrocca et al. ......... 606/41 |
| 7,429,260 B2 | 9/2008 | Underwood et al. ...... 606/32 |
| 7,429,262 B2 | 9/2008 | Woloszko et al. ......... 606/46 |
| 7,435,247 B2 | 10/2008 | Woloszko et al. ......... 604/45 |
| 2001/0025177 A1 | 9/2001 | Woloszko et al. ......... 606/46 |
| 2002/0029036 A1 | 3/2002 | Goble et al. ............... 606/32 |
| 2003/0013986 A1 | 1/2003 | Saadat ....................... 600/549 |
| 2003/0028189 A1 | 2/2003 | Woloszko et al. ......... 604/45 |
| 2003/0088245 A1 | 5/2003 | Woloszko et al. ......... 606/41 |
| 2003/0158545 A1 | 8/2003 | Hovda et al. .............. 606/32 |
| 2003/0171743 A1 | 9/2003 | Tasto et al. ................ 606/32 |
| 2003/0181898 A1 | 9/2003 | Bowers ...................... 606/304 |
| 2003/0208194 A1 | 11/2003 | Hovda et al. .............. 606/41 |
| 2003/0208196 A1 | 11/2003 | Stone ......................... 606/41 |
| 2003/0212396 A1 | 11/2003 | Eggers et al. ............. 606/41 |
| 2004/0049180 A1 | 3/2004 | Sharps et al. .............. 606/32 |
| 2004/0116922 A1 | 6/2004 | Hovda et al. .............. 606/41 |
| 2004/0127893 A1 | 7/2004 | Hovda ........................ 606/41 |
| 2004/0230190 A1 | 11/2004 | Dahla et al. ............... 604/41 |
| 2005/0004634 A1 | 1/2005 | Hovda et al. .............. 606/41 |
| 2005/0010205 A1 | 1/2005 | Hovda et al. .............. 606/32 |
| 2005/0119650 A1 | 6/2005 | Sanders et al. ............ 424/426 |
| 2005/0131402 A1 | 6/2005 | Ciarrocca et al. ......... 600/450 |
| 2005/0171533 A1 | 8/2005 | Latterell et al. ............ 606/48 |
| 2005/0187543 A1 | 8/2005 | Underwood et al. ...... 606/41 |
| 2005/0234439 A1 | 10/2005 | Underwood et al. ...... 606/32 |
| 2005/0251134 A1 | 11/2005 | Woloszko et al. ......... 606/32 |
| 2005/0261754 A1 | 11/2005 | Woloszko et al. ......... 606/32 |
| 2005/0288665 A1 | 12/2005 | Woloszko et al. ......... 606/41 |
| 2006/0036237 A1 | 2/2006 | Davison et al. ........... 606/41 |
| 2006/0095031 A1 | 5/2006 | Ormsby ..................... 606/34 |
| 2006/0178670 A1 | 8/2006 | Woloszko et al. ......... 606/48 |
| 2006/0189971 A1 | 8/2006 | Eggers et al. ............. 606/32 |
| 2006/0253117 A1 | 11/2006 | Hovda et al. .............. 128/898 |
| 2006/0259025 A1 | 11/2006 | Dahla ......................... 607/108 |
| 2007/0010808 A1 | 1/2007 | Dahla ......................... 606/41 |
| 2007/0106288 A1 | 5/2007 | Woloszko et al. ......... 606/41 |
| 2007/0112348 A1 | 5/2007 | Eggers et al. ............. 606/41 |
| 2007/0129715 A1 | 6/2007 | Eggers et al. ............. 606/32 |
| 2007/0149966 A1 | 6/2007 | Dahla et al. ............... 606/41 |
| 2007/0161981 A1 | 7/2007 | Sanders et al. ............ 606/41 |
| 2007/0179497 A1 | 8/2007 | Eggers et al. ............. 606/41 |
| 2007/0208334 A1 | 9/2007 | Woloszko et al. ......... 606/41 |
| 2007/0208335 A1 | 9/2007 | Woloszko et al. ......... 606/41 |
| 2007/0213700 A1 | 9/2007 | Davison et al. ........... 606/32 |
| 2007/0282323 A1 | 12/2007 | Woloszko et al. ......... 606/41 |

FOREIGN PATENT DOCUMENTS

| | | |
|---|---|---|
| EP | 0 623 316 B1 | 11/1994 |
| EP | 0703461 A2 | 3/1996 |
| EP | 0 717 966 B1 | 6/1996 |
| EP | 0740926 A2 | 11/1996 |
| EP | 0 754 437 | 1/1997 |
| EP | 0 694 290 | 11/2000 |
| FR | 2313949 | 1/1977 |
| GB | 2037167 | 7/1980 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| GB | 2 379 878 A | 3/2003 |
| JP | 57-57802 | 4/1982 |
| JP | 57-117843 | 7/1982 |
| WO | 90/03152 | 4/1990 |
| WO | 90/07303 | 7/1990 |
| WO | 92/21278 | 12/1992 |
| WO | 93/13816 | 7/1993 |
| WO | 93/20747 | 10/1993 |
| WO | 94/04220 | 3/1994 |
| WO | 94/08654 | 4/1994 |
| WO | 95/34259 | 12/1995 |
| WO | 96/00042 | 1/1996 |
| WO | 97/00646 | 1/1997 |
| WO | 97/00647 | 1/1997 |
| WO | 97/24073 | 7/1997 |
| WO | 97/24074 | 7/1997 |
| WO | 97/24993 | 7/1997 |
| WO | 97/24994 | 7/1997 |
| WO | 97/48345 | 12/1997 |
| WO | 97/48346 | 12/1997 |
| WO | 98/07468 | 2/1998 |
| WO | 98/27879 | 7/1998 |
| WO | 98/27880 | 7/1998 |
| WO | 99/51155 | 10/1999 |
| WO | 99/51158 | 10/1999 |
| WO | 01/87154 | 5/2001 |
| WO | 01/60273 | 8/2001 |
| WO | 02/36028 | 5/2002 |
| WO | 03/005882 | 1/2003 |
| WO | 03/028540 | 4/2003 |
| WO | 03/068055 | 8/2003 |
| WO | 2005/125287 | 12/2005 |

OTHER PUBLICATIONS

BiLAP IFU 910026-001 Rev A for BiLAP Model 3525, J-Hook, 4 pgs., May 20, 1991.
BiLAP Generator Settings, Jun. 1991.
Tucker et al. "The interaction between electrosurgical generators, endoscopic electrodes, and tissue," Gastrointestinal Endoscopy, vol. 38, No. 2, pp. 118-122, 1992.
PCT International Search Report for PCT/US01/04647, 2 pgs., Mailed Jul. 17, 2001.
PCT International Search Report for PCT/US02/21582, 2 pgs., Mailed Mar. 27, 2003.
PCT International Search Report for PCT/US02/31409, 1 pg., Mailed May 21, 2003.
PCT International Search Report for PCT/US03/07223, 1 pg., Mailed Oct. 22, 2003.
PCT International Preliminary Examination Report for PCT/US02/21582, 4 pgs., Nov. 4, 2003.
PCT International Preliminary Examination Report for PCT/US01/04647, 6 pgs., Sep. 17, 2002.
Barry et al., "The Effect of Radiofrequency-generated Thermal Energy on the Mechanical and Histologic Characteristics of the Arterial Wall in Vivo: Implications of Radiofrequency Angioplasty" American Heart Journal vol. 117, pp. 332-341, 1982.
Codman & Shurtleff, Inc. "The Malis Bipolar Coagulating and Bipolar Cutting System CMC-II" brochure, early, 2 pgs., 1991.
Codman & Shurtleff, Inc. "The Malis Bipolar Electrosurgical System CMC—III Instruction Manual", 15 pgs., Jul. 1991.
Cook et al., "Therapeutic Medical Devices: Application and Design", Prentice Hall, Inc., 3pgs., 1982.
Dennis et al. "Evolution of Electrofulguration in Control of Bleeding of Experimental Gastric Ulcers," Digestive Diseases and Sciences, vol. 24, No. 11, 845-848, Nov. 1979.

Dobbie, A.K., "The Electrical Aspects of Surgical Diathermy, Bio Medical Engineering" *Bio-Medical Engineering* vol. 4, pp. 206-216, May 1969.

Elsasser, V.E. et al., "An Instrument for Transurethral Resection without Leakage of Current" *Acta Medicotechnica* vol. 24, No. 4, pp. 129-134, 1976.

Geddes, "Medical Device Accidents: With Illustrative Cases" CRC Press, 3 pgs., 1998.

Honig, W., "The Mechanism of Cutting in Electrosurgery" *IEEE* pp. 58-65, 1975.

Kramolowsky et al. "The Urological App of Electorsurgery" *J. of Urology* vol. 146, pp. 669-674, 1991.

Kramolowsky et al. "Use of 5F Bipolar Electrosurgical Probe in Endoscopic Urological Procedures" *J. of Urology* vol. 143, pp. 275-277, 1990.

Lee, B et al. "Thermal Compression and Molding of Artherosclerotic Vascular Tissue with Use" JACC vol. 13(5), pp. 1167-1171, 1989.

Letter from Department of Health to Jerry Malis dated Jan. 24, 1991, 3 pgs.

Letter from Department of Health to Jerry Malis dated Jul. 25, 1985, 1 pg.

Letter from Jerry Malis to FDA dated Jul. 25, 1985, 2 pgs.

Lu, et al., "Electrical Thermal Angioplasty: Catheter Design Features, In Vitro Tissue Ablation Studies and in Vitro Experimental Findings," *Am J. Cardiol* vol. 60, pp. 1117-1122, Nov. 1, 1987.

Malis, L., "Electrosurgery, Technical Note," *J. Neursurg.*, vol. 85, pp. 970-975, Nov. 1996.

Malis, L., "Excerpted from a seminar by Leonard I. Malis, M.D. at the 1995 American Association of Neurological Surgeons Meeting," 1pg., 1995.

Malis, L., "Instrumentation for Microvascular Neurosurgery" *Cerebrovascular Surgery*, vol. 1, pp. 245-260 1985.

Malis, L., "New Trends in Microsurgery and Applied Technology," *Advanced Technology in Neurosurgery*, pp. 1-16, 1988.

Malls, L., "The Value of Irrigation During Bipolar Coagulation" See ARTC 21602, 1 pg., Apr. 9, 1993.

Nardella, P.C., *SPIE* 1068: pp. 42-49, Radio Frequency Energy and Impedance Feedback, 1989.

O'Malley, Schaum's Outline of Theory and Problems of Basic Circuit Analysis, McGraw-Hill, $2^{nd}$ Ed., pp. 3-5, 1992.

Pearce, John A. "Electrosurgery", pp. 17, 69-75, 87, John Wiley & Sons, New York, 1986.

Pearce, John A., "Electrosurgery", Handbook of Biomedical Engineering, chapter 3, Academic Press Inc., N.Y., pp. 98-113, 1988.

Piercey et al., "Electrosurgical Treatment of Experimental Bleeding Canine Gastric Ulcers" *Gastroenterology* vol. 74(3), pp. 527-534, 1978.

Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.

Ramsey et al., "A Comparison of Bipolar and Monopolar Diathermy Probes in Experimental Animals", *Urological Research* vol. 13, pp. 99-102, 1985.

Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.

Shuman, "Bipolar Versus Monopolar Electrosurgery: Clinical Applications," *Dentistry Today*, vol. 20, No. 12, 7 pgs, Dec. 2001.

Slager et al. "Spark Erosion of Arteriosclerotic Plaques" *Z. Kardiol.* 76:Suppl. 6, pp. 67-71, 1987.

Slager et al. "Vaporization of Atherosclerotice Plaques by Spark Erosion" *JACC* 5(6): pp. 1382-1386, Jun. 1985.

Stoffels, E. et al., "Investigation on the Interaction Plasma-Bone Tissue", E-MRS Spring Meeting, 1 pg., Jun. 18-21, 2002.

Stoffels, E. et al., "Biomedical Applications of Plasmas", Tutorial presented prior to the $55^{th}$ Gaseous Electronics Conference in Minneapolis, MN, 41 pgs., Oct. 14, 2002.

Stoffels, E. et al., "Plasma Interactions with Living Cells", Eindhoven University of Technology, 1 pg., 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg., Nov. 28, 2003.

Stoffels, E. et al., "Plasma Physicists Move into Medicine", Physicsweb, 1 pg., Nov. 2003.

Stoffels, E. et al., "Plasma Treated Tissue Engineered Skin to Study Skin Damage", Biomechanics and Tissue Engineering, Materials Technology, 1 pg., 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs., 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia Coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for in Vivo Medical Treatment: Recent Developments and Perspectives", Plasma Sources Sci. Technol. 15, pp. S169-S180, Oct. 6, 2006.

Swain, C.P., et al., "Which Electrode, A Comparison of four endoscopic methods of electrocoagulation in experimental bleeding ulcers" *Gut* vol. 25, pp. 1424-1431, 1987.

Tucker, R. et al. "A Comparison of Urologic Application of Bipolar Versus Monopolar Five French Electrosurgical Probes" *J. of Urology* vol. 141, pp. 662-665, 1989.

Tucker, R. et al. "In vivo effect of 5 French Bipolar and Monopolar Electrosurgical Probes on the Porcine Bladder" *Urological Research* vol. 18, pp. 291-294, 1990.

Tucker, R. et al., "Demodulated Low Frequency Currents from Electrosurgical Procedures," *Surgery, Gynecology and Obstetrics*, 159:39-43, 1984.

Tucker, R. et al., Abstract P14-11, p. 248, "A Bipolar Electrosurgical Turp Loop", Nov. 1989.

Valley Forge Scientific Corp., "Summary of Safety and Effective Information from 510K", 2pgs., 1991.

Valley Forge's New Products, CLINICA, 475, 5, Nov. 6, 1991.

Valleylab SSE2L Instruction Manual, 11 pgs., Jan. 6, 1983.

Valleylab, Inc. "Valleylab Part No. 945 100 102 A" Surgistat Service Manual, pp. 1-46, Jul. 1988.

Wattiez, Arnaud et al., "Electrosurgery in Operative Endoscopy," Electrosurgical Effects, Blackwell Science, pp. 85-93, 1995.

Wyeth, "Electrosurgical Unit" pp. 1181-1202, 2000.

\* cited by examiner

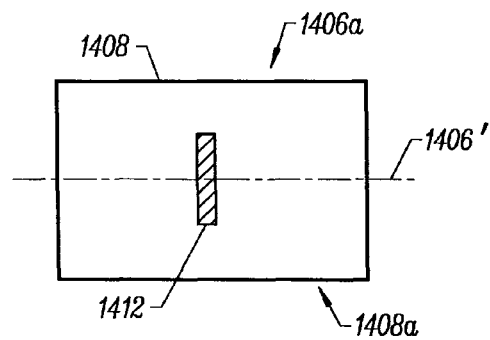
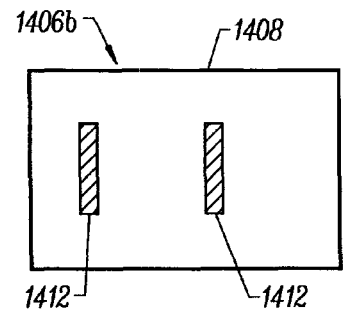
FIG. 16A             FIG. 16B
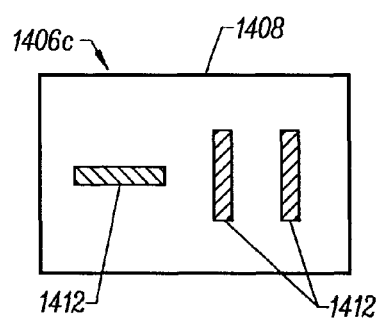
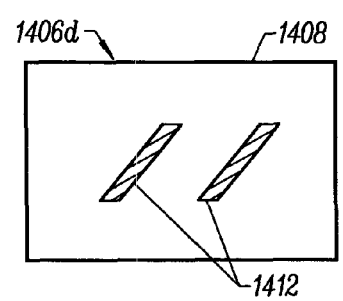
FIG. 16C             FIG. 16D
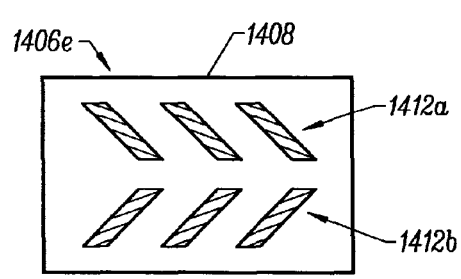
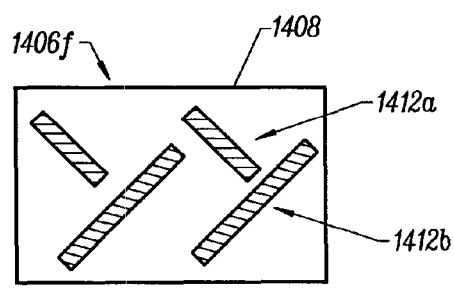
FIG. 16E             FIG. 16F

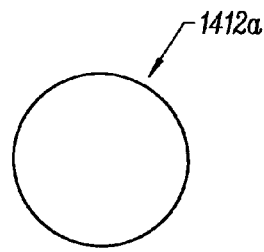
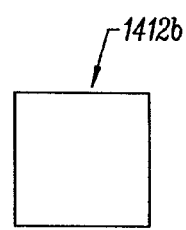
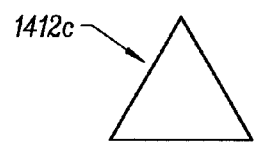
FIG. 19A          FIG. 19B          FIG. 19C
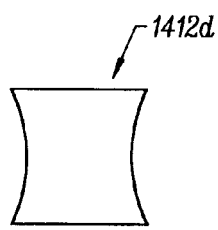
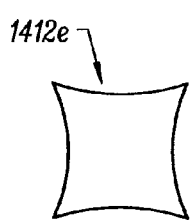
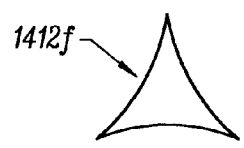
FIG. 19D          FIG. 19E          FIG. 19F
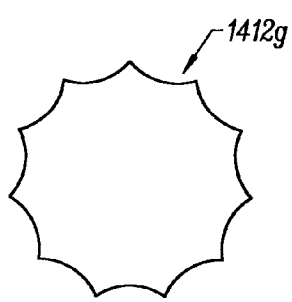
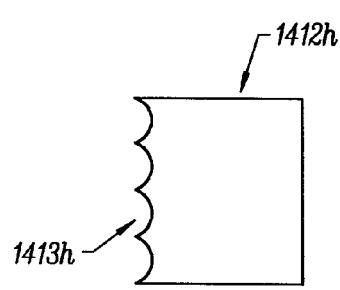
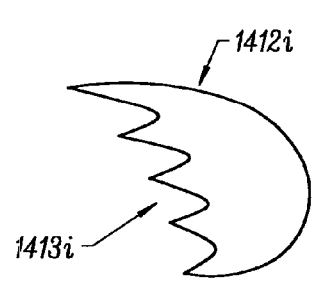
FIG. 19G          FIG. 19H          FIG. 19I

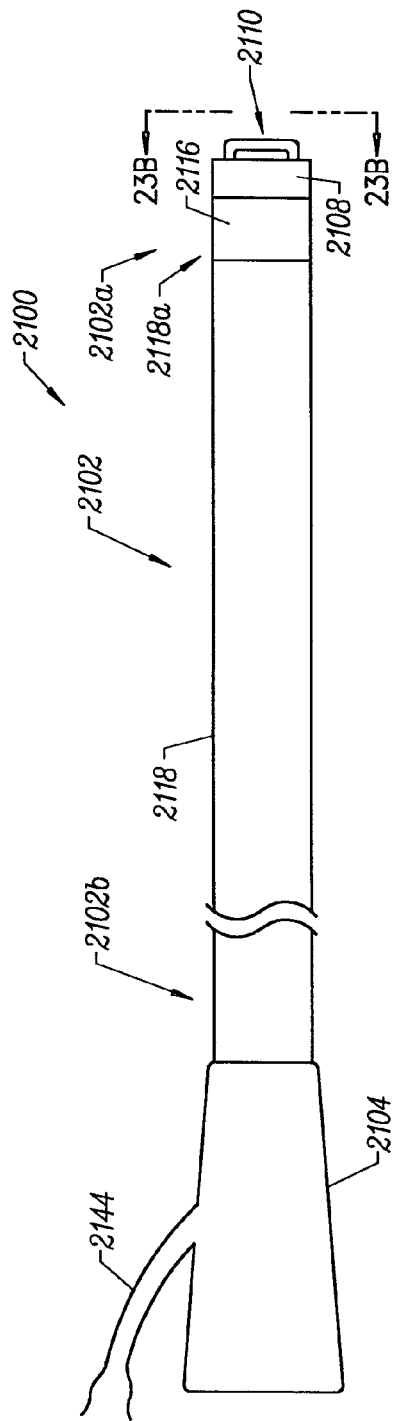
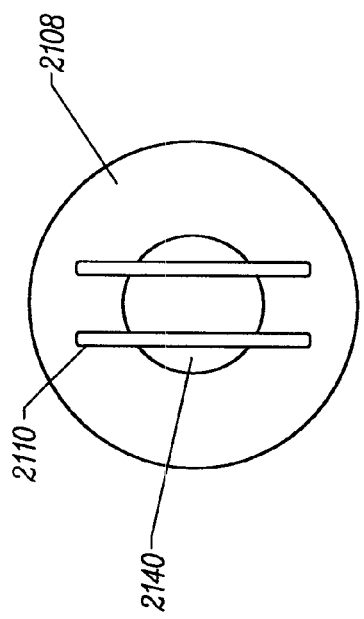
FIG. 23A
FIG. 23B

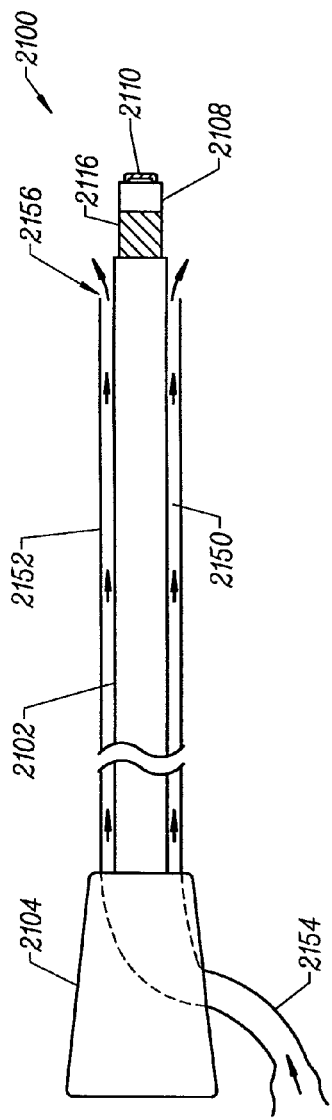
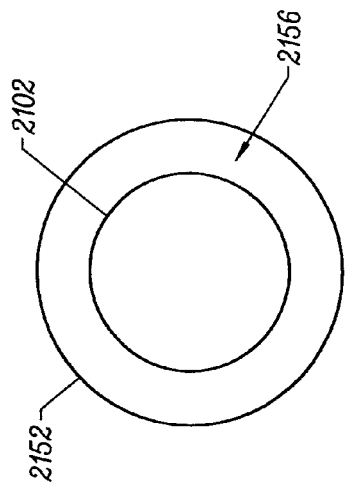
FIG. 25A
FIG. 25B

ELECTROSURGICAL APPARATUS AND METHODS FOR LAPAROSCOPY

RELATED APPLICATIONS

The present application is a divisional of U.S. patent application Ser. No. 10/365,759, filed Feb. 14, 2003, now U.S. Pat. No. 7,331,957, the complete disclosure of which is incorporated by reference. U.S. application Ser. No. 10/365,759 is a continuation-in-part of U.S. patent application Ser. No. 09/766,168 filed Jan. 19, 2001, now U.S. Pat. No. 6,589,237 which claims priority from U.S. Provisional Patent Application No. 60/233,345 filed Sep. 18, 2000, and claims priority from U.S. Provisional Patent Application No. 60/210,567 filed Jun. 9, 2000. U.S. patent application Ser. No. 09/766,168, now U.S. Pat. No. 6,589,237 filed Jan. 19, 2001, is a continuation-in-part of U.S. patent application Ser. No. 09/197,013, filed Nov. 20, 1998, now U.S. Pat. No. 6,296,638 which is a continuation-in-part of U.S. patent application Ser. No. 09/010,382, filed Jan. 21, 1998, now U.S. Pat. No. 6,190,381, which is a continuation-in-part of U.S. patent application Ser. No. 08/990,374, filed on Dec. 15, 1997, now U.S. Pat. No. 6,109,268, which is a continuation-in-part of U.S. patent application Ser. No. 08/485,219, filed on Jun. 7, 1995, now U.S. Pat. No. 5,697,281, which is a continuation-in-part of U.S. patent application Ser. No. 08/446,767 filed Jun. 2, 1995, now U.S. Pat. No. 5,697,909, which is U.S. national stage entry of International Application No. PCT/US94/05168 filed May 10, 1994, which is a continuation-in-part of U.S. patent application Ser. No. 08/059,681, filed on May 10, 1993, now abandoned, which is a continuation-in part of U.S. patent application Ser. No. 07/958,977 filed Oct. 9, 1992, now U.S. Pat. No. 5,366,443, which is a continuation-in-part of U.S. patent application Ser. No. 07/817,575 filed Jan. 7, 1992, now abandoned, the complete disclosures of which are incorporated herein by reference for all purposes.

The present invention is related to commonly assigned U.S. Provisional Patent Application No. 60/062,997 filed on Oct. 23, 1997, U.S. patent application Ser. No. 08/977,845 filed Nov. 25, 1997, now U.S. Pat. No. 6,210,402, which is a continuation-in-part of U.S. patent application Ser. No. 08/562,332 filed Nov. 22, 1995, now U.S. Pat. No. 6,024,733, the complete disclosures of which are incorporated herein by reference for all purposes. The present invention is also related to U.S. patent application Ser. Nos. 09/109,219, 09/058,571, 08/874,173 and 09/002,315, filed on Jun. 30, 1998, Apr. 10, 1998, Jun. 13, 1997, and Jan. 2, 1998, respectively and U.S. patent application Ser. No. 09/054,323 filed on Apr. 2, 1998, U.S. patent application Ser. No. 09/010,382 filed Jan. 21, 1998, and U.S. patent application Ser. No. 09/032,375 filed Feb. 27, 1998, U.S. patent application Ser. No. 08/942,580, filed on Oct. 2, 1997, U.S. patent application Ser. No. 08/753,227 filed on Nov. 22, 1996, and U.S. patent application Ser. No. 08/687,792 filed on Jul. 18, 1996, the complete disclosures of which are incorporated herein by reference for all purposes. The present invention is also related to commonly assigned U.S. patent application Ser. No. 08/562,331 filed Nov. 22, 1995, now U.S. Pat. No. 5,683,366, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to ablate, resect, coagulate, or otherwise modify a target tissue. The present invention also relates to apparatus and methods for the controlled removal of tissue at a target site by electrosurgical ablation (e.g., Coblation®), and for efficiently aspirating resected tissue from the target site, wherein the depth to which tissue is removed can be precisely controlled with minimal or no collateral damage, and all ablation by-products are removed via an aspiration unit.

Conventional electrosurgical methods generally reduce patient bleeding associated with tissue cutting operations and improve the surgeon's visibility. These electrosurgical devices and procedures, however, suffer from a number of disadvantages. For example, monopolar electrosurgery methods generally direct electric current along a defined path from the exposed or active electrode through the patient's body to the return electrode, which is externally attached to a suitable location on the patient's skin. In addition, since the defined path through the patient's body has a relatively high electrical impedance, large voltage differences must typically be applied between the active and return electrodes to generate a current suitable for cutting or coagulation of the target tissue. This current, however, may inadvertently flow along localized pathways in the body having less impedance than the defined electrical path. This situation will substantially increase the current flowing through these paths, possibly causing damage to or destroying tissue along and surrounding this pathway.

Bipolar electrosurgical devices have an inherent advantage over monopolar devices because the return current path does not flow through the patient beyond the immediate site of application of the bipolar electrodes. In bipolar devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue.

Another limitation of conventional bipolar and monopolar electrosurgery devices is that they are not suitable for the precise removal (ablation) of tissue. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. The tissue is parted along the pathway of vaporized cellular fluid, inducing undesirable collateral tissue damage in regions surrounding the target tissue site.

In addition, conventional electrosurgical methods are generally ineffective for ablating certain types of tissue, and in certain types of environments within the body. For example, loose or elastic connective tissue, such as the synovial tissue in joints, is extremely difficult (if not impossible) to remove with conventional electrosurgical instruments because the flexible tissue tends to move away from the instrument when it is brought against this tissue. Since conventional techniques rely mainly on conducting current through the tissue, they are not effective when the instrument cannot be brought adjacent to or in contact with the elastic tissue for a long enough period of time to energize the electrode and conduct current through the tissue.

The use of electrosurgical procedures (both monopolar and bipolar) in electrically conductive environments can be further problematic. For example, many arthroscopic procedures require flushing of the region to be treated with isotonic saline, both to maintain an isotonic environment and to keep the field of view clear. However, the presence of saline, which is a highly conductive electrolyte, can cause shorting of the active electrode(s) in conventional monopolar and bipolar electrosurgery. Such shorting causes unnecessary heating in the treatment environment and can further cause non-specific tissue destruction.

Conventional electrosurgical cutting or resecting devices also tend to leave the operating field cluttered with tissue fragments that have been removed or resected from the target tissue. These tissue fragments make visualization of the surgical site extremely difficult. Removing these tissue fragments can also be problematic. Similar to synovial tissue, it is difficult to maintain contact with tissue fragments long enough to ablate the tissue fragments in situ with conventional devices. To solve this problem, the surgical site is periodically or continuously aspirated during the procedure. However, the tissue fragments often clog the aspiration lumen of the suction instrument, forcing the surgeon to remove the instrument to clear the aspiration lumen or to introduce another suction instrument, which increases the length and complexity of the procedure.

Endometriosis is a common condition due to the presence of ectopic endometrial tissue, usually within the abdominal cavity, which can lead to infertility in women. Endometrial lesions or implants respond to ovarian hormonal changes, similar to the uterine endometrium. Symptoms of endometriosis include localized bleeding, pain, inflammation, scarring, and adhesion formation.

There is a need for improved treatment of endometriosis. Medical therapy for endometriosis is basically hormonal. Treatment with continuous progesterone can shrink endometriotic implants. Treatment that causes a significant decrease in estrogen levels (pseudomenopausal state) is generally more effective than a prolonged progesterone effect. Agents that suppress ovarian estrogen production include Danazol (a weak androgenic hormone), and Lupron (a gonadotropin-releasing hormone agonist). Prescription of such products is usually limited to periods of not more than six months due to their side effects (including bone demineralization and increased risk of cardiovascular disease). Often, the beneficial effects of such products are short-lived following cessation of treatment. Prior to recent advances in laparoscopic instrumentation and procedures, a common treatment for endometriosis was pelvic laparotomy. Lasers have been used for removal of endometrial lesions. However, in the context of surgical ablation, lasers suffer from a number of disadvantages, as outlined hereinabove. Thus, there is a need for improved electrosurgical instruments which allow the removal of ectopic endometrial tissue from various sites during minimally invasive laparoscopic procedures, wherein the target tissue is removed in a highly controlled manner with little or no collateral damage.

The instant invention provides methods and electrosurgical apparatus for the controlled removal or coagulation of target tissue during laparoscopic procedures with no or minimal damage to delicate, easily damaged underlying tissue.

SUMMARY OF THE INVENTION

The present invention provides systems, apparatus, and methods for selectively applying electrical energy to structures or tissue of a patient's body. In particular, methods and apparatus are provided for resecting, cutting, ablating, aspirating, or otherwise removing tissue from a target site in situ, during laparoscopic procedures. The invention also provides systems and apparatus for spot coagulation and ablation of target tissue, such as ectopic endometrial tissue present on delicate underlying tissue or organs, such as the ovaries, ureter, urinary bladder, and bowel.

In one aspect, the present invention provides an electrosurgical instrument for treating tissue at a target site. The instrument comprises a shaft having a proximal portion and a distal end portion. One or more active loop electrodes are disposed at the distal end of the shaft. The loop electrodes preferably have one or more edges that promote high electric fields. A connector is disposed near the proximal end of the shaft for electrically coupling the active loop electrodes to a high frequency source.

The active loop electrodes typically have an exposed semicircular shape that facilitates the removing or ablating of tissue at the target site. During the procedure, bodily fluid, non-ablated tissue fragments and/or air bubbles are aspirated from the target site to improve visualization.

At least one return electrode is preferably spaced from the active electrode(s) a sufficient distance to prevent arcing therebetween at the voltages suitable for tissue removal and or heating, and to prevent contact of the return electrode(s) with the tissue. The current flow path between the active and return electrodes may be generated by immersing the target site within electrically conductive fluid (as is typical in arthroscopic procedures), or by directing an electrically conductive fluid along a fluid path past the return electrode and to the target site (e.g., in open procedures). Alternatively, the electrodes may be positioned within a viscous electrically conductive fluid, such as a gel, at the target site, and submersing the active and return electrode(s) within the conductive gel. The electrically conductive fluid will be selected to have sufficient electrical conductivity to allow current to pass therethrough from the active to the return electrode(s), and such that the fluid ionizes into a plasma when subject to sufficient electrical energy, as discussed below. In the exemplary embodiment, the conductive fluid is isotonic saline, although other fluids may be selected, as described in co-pending Provisional Patent Application No. 60/098,122, filed Aug. 27, 1998, the complete disclosure of which is incorporated herein by reference.

In a specific embodiment, tissue ablation results from molecular dissociation or disintegration processes. Conventional electrosurgery ablates or cuts through tissue by rapidly heating the tissue until cellular fluids explode, producing a cutting effect along the pathway of localized heating. The present invention volumetrically removes tissue, e.g., cartilage tissue, in a cool ablation process known as Coblation®, wherein thermal damage to surrounding tissue is minimized. During this process, a high frequency voltage applied to the active electrode(s) is sufficient to vaporize an electrically conductive fluid (e.g., gel or saline) between the electrode(s) and the tissue. Within the vaporized fluid, an ionized plasma is formed and charged particles (e.g., electrons) cause the molecular breakdown or disintegration of tissue components in contact with the plasma. This molecular dissociation is accompanied by the volumetric removal of the tissue. This process can be precisely controlled to effect the volumetric removal of tissue as thin as 10 to 50 microns with minimal heating of, or damage to, surrounding or underlying tissue structures. A more complete description of this Coblation® phenomenon is described in commonly assigned U.S. Pat. No. 5,683,366, the complete disclosure of which is incorporated herein by reference.

In variations of the invention which use Coblation® technology, the high frequency voltage is sufficient to convert the electrically conductive fluid between the target tissue and active electrodes into an ionized vapor layer or plasma. As a result of the applied voltage difference between active electrode(s) and the target tissue (i.e., the voltage gradient across the plasma layer), charged particles in the plasma (e.g., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. The short range of the accelerated charged particles within the tissue confines the molecular dissociation process to the surface layer to minimize damage and necrosis to the underlying tissue.

During the process, the gases may be aspirated through opening 609 and/or a suction tube to a vacuum source or collection reservoir. In addition, excess electrically conductive fluid and other fluids (e.g., blood) will be aspirated from the target site to facilitate the surgeon's view. Applicant has also found that tissue fragments are also aspirated through opening into suction lumen and tube during the procedure. These tissue fragments are ablated or dissociated with electrodes with a mechanism similar to that described above. Namely, as electrically conductive fluid and tissue fragments are aspirated towards loop electrodes, these electrodes are activated so that a high frequency voltage is applied to loop electrodes and return electrode (of course, the probe may include a different, separate return electrode for this purpose). The voltage is sufficient to vaporize the fluid, and create a plasma layer between loop electrodes 540 and the tissue fragments so that portions of the tissue fragments are ablated or removed. This reduces the volume of the tissue fragments as they pass through suction lumen to minimize clogging of the lumen.

The present invention offers a number of advantages over conventional electrosurgery, microdebrider, shaver and laser techniques for removing soft tissue in arthroscopic, sinus or other surgical procedures. The ability to precisely control the volumetric removal of tissue results in a field of tissue ablation or removal that is very defined, consistent and predictable. In one embodiment, the shallow depth of tissue heating also helps to minimize or completely eliminate damage to healthy tissue structures, e.g., cartilage, bone and/or nerves that are often adjacent the target tissue. In addition, small blood vessels at the target site are simultaneously cauterized and sealed as the tissue is removed to continuously maintain hemostasis during the procedure. This increases the surgeon's field of view, and shortens the length of the procedure. Moreover, since the present invention allows for the use of electrically conductive fluid (contrary to prior art bipolar and monopolar electrosurgery techniques), isotonic saline may be used during the procedure. Saline is the preferred medium for irrigation because it has the same concentration as the body's fluids and, therefore, is not absorbed into the body as much as certain other fluids.

Systems according to the present invention generally include an electrosurgical instrument having a shaft with proximal and distal end portions, one or more active electrode(s) at the distal end of the shaft and one or more return electrode(s). The system can further include a high frequency power supply for applying a high frequency voltage difference between the active electrode(s) and the return electrode(s). The instrument typically includes an aspiration lumen within the shaft having an opening positioned proximal of the active electrode(s) so as to draw excess or unwanted materials into the aspiration lumen under vacuum pressure.

In another aspect, the present invention provides an electrosurgical probe having a fluid delivery element for delivering electrically conductive fluid to the active electrode(s) and the target site. In one exemplary configuration, the fluid delivery element includes at least one opening that is positioned around the active electrodes. Such a configuration provides an improved flow of electrically conductive fluid and promotes more aggressive generation of a plasma at the active electrode(s).

Alternatively, in some embodiments an electrically conductive fluid, such as a gel or liquid spray, e.g., saline, may be applied to the tissue using an ancillary device. In arthroscopic procedures, the target site will typically be immersed in a conductive irrigant, e.g., saline. In these embodiments, the apparatus may lack a fluid delivery element. In both embodiments, the electrically conductive fluid will preferably generate a current flow path between the active electrode(s) and the return electrode(s). In an exemplary embodiment, a return electrode is located on the instrument and spaced a sufficient distance from the active electrode(s) to substantially avoid or minimize current shorting therebetween and to shield the tissue from the return electrode at the target site.

In another aspect, the present invention provides a method for applying electrical energy to a target site within or on a patient's body. The method comprises positioning one or more active electrodes into at least close proximity with the target site. An electrically conductive fluid is provided to the target site and a high frequency voltage is applied between the active electrodes and a return electrode to generate relatively high, localized electric field intensities at the surface of the active electrode(s). The active electrodes may be moved in relation to the targeted tissue to resect or ablate the tissue at the target site.

In another aspect, the present invention provides an electrosurgical suction apparatus adapted for coupling to a high frequency power supply and for removing tissue from a target site to be treated. The apparatus includes an aspiration channel terminating in a distal opening or aspiration port, and a plurality of active electrodes in the vicinity of the distal opening. The plurality of active electrodes may be structurally similar or dissimilar.

In one embodiment, a plurality of active electrodes are arranged substantially parallel to each other on an electrode support. In some embodiments, one or more of the plurality of active electrodes traverses a void in the electrode support. Typically, each of the plurality of active electrodes extends distally from a treatment surface of the electrode support. According to another aspect of the invention, the plurality of active electrodes may be oriented in a plurality of different directions with respect to the treatment surface. In one embodiment, a loop portion of each of the plurality of active electrodes is oriented in a different direction with respect to the treatment surface. In one embodiment, the orthogonal distance from the treatment surface to a distal face of each active electrode is substantially the same.

According to one aspect of the invention, a baffle or screen is provided at the distal end of the apparatus. In one embodiment the baffle is recessed within the void to impede the flow of solid material into the aspiration channel, and to trap the solid material in the vicinity of at least one of the plurality of active electrodes, whereby the trapped material may be readily digested.

In use, the plurality of active electrodes are coupled to a first pole of the high frequency power supply, and a return electrode is coupled to a second pole of the high frequency power supply for supplying high frequency alternating current to the device. Each of the plurality of active electrodes is capable of ablating tissue via a controlled ablation mechanism involving molecular dissociation of tissue components to yield low molecular weight ablation by-products. During this process, tissue fragments may be resected from the target site. Such resected tissue fragments may be digested by one or more of the plurality of active electrodes via essentially the same cool ablation mechanism as described above (i.e., involving molecular dissociation of tissue components), to form smaller tissue fragments and/or low molecular weight ablation by-products. The smaller tissue fragments and low molecular weight ablation by-products, together with any other unwanted materials (e.g., bodily fluids, extraneous saline) may be aspirated from the target site via the aspiration channel.

In another aspect, the present invention provides a method for removing tissue from a target site via an electrosurgical suction device, wherein a plurality of active electrodes are juxtaposed with the target tissue, and a high frequency voltage is applied to the plurality of active electrodes sufficient to ablate the tissue via localized molecular dissociation of tissue components. In one embodiment, the apparatus is adapted for efficiently ablating tissue and for rapidly removing unwanted materials, including resected tissue fragments, from the target site. In another aspect of the invention, the apparatus is adapted for providing a relatively smooth, even contour to a treated tissue.

In another aspect, the present invention provides an electrosurgical instrument or probe adapted for coupling to a high frequency power supply and for treating tissue at a target site. The instrument includes an electrode assembly including at least one active electrode disposed on an electrode support. In one embodiment, a plurality of active electrodes are arranged substantially parallel to each other on the electrode support.

According to another aspect of the invention, an electrosurgical instrument includes an electrode support having a treatment surface and a recess within the treatment surface, and each of a plurality of active electrodes spans or traverses the recess. In one embodiment, each of the plurality of active electrodes includes a bridge portion spaced from the treatment surface.

In another embodiment, an electrode support of an electrosurgical instrument includes a treatment surface and a recess within the treatment surface, wherein the recess includes a void therein, the void defining an aspiration port adapted for aspirating unwanted or excess materials from a surgical site during a procedure.

In another aspect, the present invention provides an electrosurgical instrument including a shaft, and an electrode assembly disposed at a distal end of the shaft. In one embodiment, the shaft includes an inner shaft and an outer shaft. According to one aspect of the invention, a proximal portion of the inner shaft lies within a distal portion of the outer shaft. In one embodiment, the inner shaft comprises a metal tube or cylinder, while the outer shaft comprises an electrically insulating tube.

According to another aspect of the invention, there is provided an electrosurgical instrument including a shaft, having a shaft distal end and a shaft proximal end, and an integral fluid delivery element or unit. In one embodiment, the fluid delivery unit includes a plurality of fluid channels, each fluid channel defined jointly by an external groove in the shaft distal end and an inner surface of a sleeve, wherein the sleeve ensheathes a distal portion of the shaft.

In another aspect, the invention provides a method of treating tissue at a target site using an electrosurgical instrument having at least one active electrode disposed on an electrode support. The active electrode(s) is/are positioned in at least close proximity to the target tissue, and a high frequency voltage is applied between the active electrode(s) and a return electrode, wherein the applied voltage is effective in removing the target tissue in a controlled manner, such that underlying tissue exhibits little or no damage. According to one aspect of the invention, the instrument and method are adapted for laparoscopic procedures. In one embodiment, the method involves spot coagulation and/or ablation of endometrial implants, and the instrument is adapted for removing endometrial implants from delicate tissues or organs, such as the bowel, ureter, and ovaries.

A further understanding of the nature and advantages of the invention will become apparent by reference to the remaining portions of the specification and drawings.

BRIEF DESCRIPTION OF THE DRAWINGS

FIGS. 16A-F each show a resection unit having at least one resection electrode head arranged on a resection electrode support, according to various embodiments of the invention;

FIGS. 19A-I each show a cross-section of a resection electrode head, according to one embodiment of the invention, as seen along the lines 19A-I of FIG. 18B;

FIGS. 23A and 23B show a side view and an end-view, respectively, of an electrosurgical suction apparatus, according to another embodiment of the invention;

FIG. 25A shows an electrosurgical suction apparatus having an outer sheath, according to another embodiment of the invention;

FIG. 25B shows a transverse cross-section of the apparatus of FIG. 25A;

DESCRIPTION OF SPECIFIC EMBODIMENTS

Figure 1:
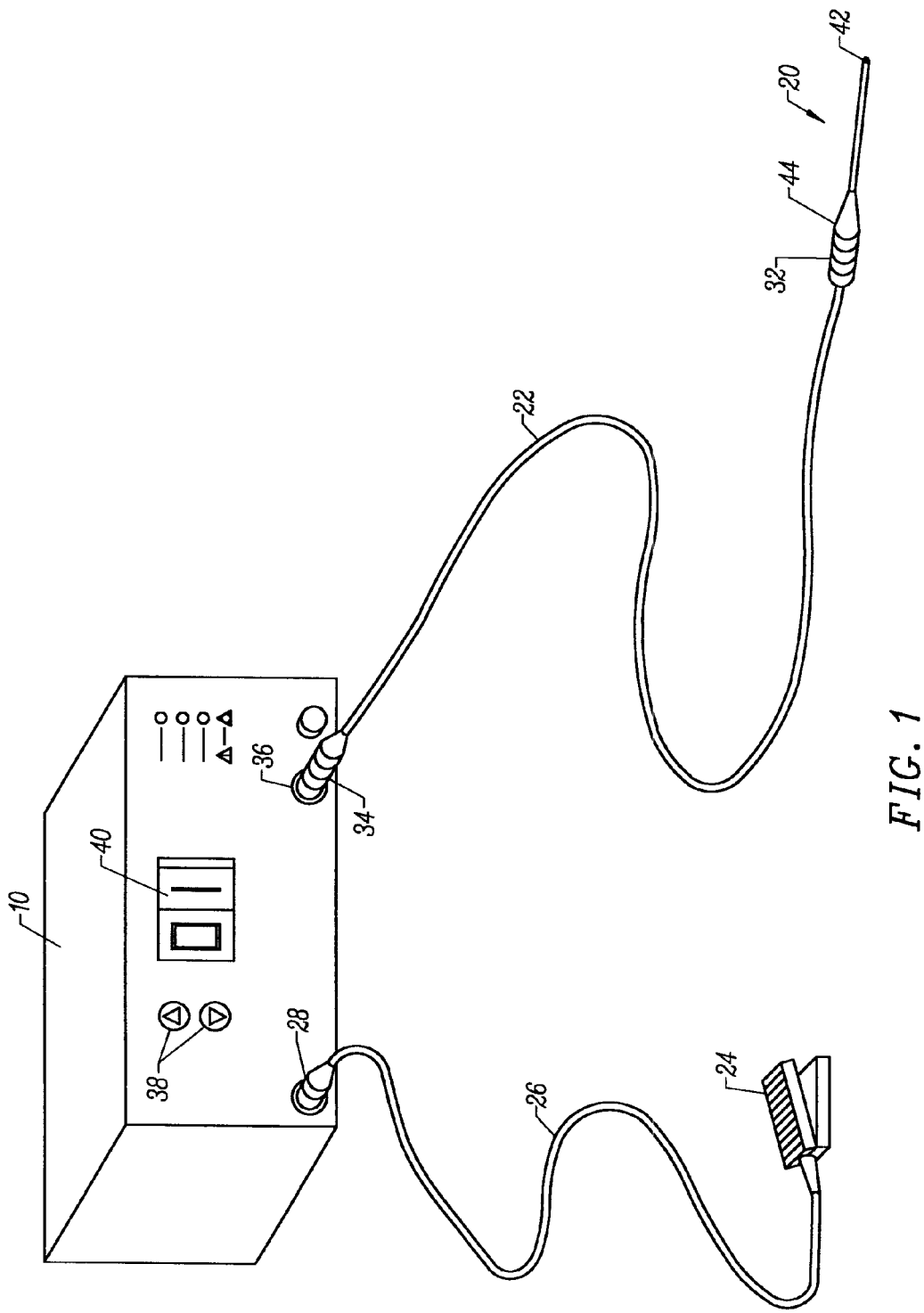
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body. The present invention is particularly useful in laparoscopic procedures, such as procedures for the treatment of endometriosis, and in laparoscopic oncology. In addition, tissues which may be treated by the system and method of the present invention include, but are not limited to, prostate tissue and leiomyomas (fibroids) located within the uterus, gingival tissues and mucosal tissues located in the mouth, tumors, scar tissue, myocardial tissue, collagenous tissue within the eye or epidermal and dermal tissues on the surface of the skin. Other procedures for which the present invention may be used include arthroscopic procedures, laminectomy/diskectomy procedures for treating herniated disks, decompressive laminectomy for stenosis in the lumbosacral and cervical spine, posterior lumbosacral and cervical spine fusions, treatment of scoliosis associated with vertebral disease, foraminotomies to remove the roof of the intervertebral foramina to relieve nerve root compression, as well as anterior cervical and lumbar diskectomies. The present invention is also useful for resecting tissue within accessible sites of the body that are suitable for electrode loop resection, such as the resection of prostate tissue, leiomyomas (fibroids) located within the uterus, and other diseased or abnormal tissue within the body.

The present invention may also be used to treat tissue or organs of the head and neck, such as the ear, mouth, pharynx, larynx, esophagus, nasal cavity and sinuses. Such procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucous linings, polyps and/or neoplasms from the various anatomical sinuses of the skull, the turbinates and nasal passages, in the tonsil, adenoid, epiglottic and supra-glottic regions, salivary glands, and other tissues; submucous resection of the nasal septum; and excision of diseased tissue, and the like. In other procedures, the present invention may be useful for collagen shrinkage, ablation, and/or hemostasis in procedures for treating snoring and obstructive sleep apnea (e.g., soft palate, such as the uvula, or tongue/pharynx stiffening, and midline glossectomies); for gross tissue removal, such as tonsillectomies, adenoidectomies, tracheal stenosis and vocal cord polyps and lesions; or for the resection or ablation of facial tumors or tumors within the mouth and pharynx, such as glossectomies, laryngectomies, acoustic neuroma procedures; and nasal ablation procedures. In addition, the present invention may also be used for procedures within the ear, such as stapedotomies, tympanostomies, or the like.

The present invention may also be useful for cosmetic and plastic surgery procedures in the head and neck. For example, the present invention may be used for ablation and sculpting of cartilage tissue, such as the cartilage within the nose that is sculpted during rhinoplasty procedures. The present invention may also be employed for skin tissue removal and/or collagen shrinkage in the epidermis or dermis tissue in the head and neck, e.g., the removal of pigmentations, vascular lesions (e.g., leg veins), scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

For convenience, certain embodiments of the invention will be described primarily with respect to the treatment of endometrial implants; resection and/or ablation of the meniscus and the synovial tissue within a joint during an arthroscopic procedure; and to the ablation, resection and/or aspiration of sinus tissue during an endoscopic sinus surgery procedure. However, it will be appreciated that the systems, apparatus, and methods of the invention may also be applied to procedures involving other tissues or organs of the body, including open procedures, intravascular procedures, urological procedures, laparoscopy, arthroscopy, thoracoscopy or other cardiac procedures, dermatology, orthopedics, gynecology, otorhinolaryngology, spinal and neurologic procedures, oncology, and the like.

In the present invention, high frequency (RF) electrical energy is applied to one or more active electrodes in the presence of electrically conductive fluid to remove and/or modify a target tissue or organ. Depending on the specific procedure, the present invention may be used to: (1) volumetrically remove tissue, bone or cartilage (i.e., ablate or effect molecular dissociation of the tissue structure); (2) cut or resect tissue; (3) shrink or contract collagen connective tissue; and/or (4) coagulate severed blood vessels.

In one aspect of the invention, systems and methods are provided for the volumetric removal or ablation of tissue structures. In these procedures, a high frequency voltage difference is applied between one or more active electrode(s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid from within the cells of the tissue, as is typically the case with electrosurgical desiccation and vaporization.

The high electric field intensities may be generated by applying a high frequency voltage that is sufficient to vaporize an electrically conductive fluid over at least a portion of the active electrode(s) in the region between the distal tip of the active electrode(s) and the target tissue. The electrically conductive fluid may be a gas or liquid, such as isotonic saline, delivered to the target site, or a viscous fluid, such as a gel, that is located at the target site. In the latter embodiment, the active electrode(s) are submersed in the electrically conductive gel during the surgical procedure. Since the vapor layer or vaporized region has a relatively high electrical impedance, it minimizes the current flow into the electrically conductive fluid. This ionization, under optimal conditions, induces the discharge of energetic electrons and photons from the vapor layer to the surface of the target tissue. A more detailed description of this cold ablation phenomenon, termed Coblation®, can be found in commonly assigned U.S. Pat. No. 5,683,366 the complete disclosure of which is incorporated herein by reference.

In one embodiment, the present invention applies high frequency (RF) electrical energy in an electrically conductive fluid environment to remove (i.e., resect, cut, or ablate) or contract a tissue structure, and to seal transected vessels within the region of the target tissue. The present invention may be used for sealing larger arterial vessels, e.g., on the order of 1 mm in diameter or greater. In some embodiments, a high frequency power supply is provided having an ablation mode, wherein a first voltage is applied to an active electrode sufficient to effect molecular dissociation or disintegration of the tissue, and a coagulation (or sub-ablation) mode, wherein a second, lower voltage is applied to an active electrode (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more active electrodes configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate tissue with the coagulation electrode(s), and to ablate or contract the tissue with the active electrode(s). In other embodiments, the power supply is combined with the probe such that the coagulation electrode receives power when the power supply is in the coagulation mode (low voltage), and the active electrode(s) receive power when the power supply is in the ablation mode (higher voltage).

In a method according to one embodiment of the present invention, one or more active electrodes are brought into close proximity to tissue at a target site, and the power supply is activated in the ablation mode such that sufficient voltage is applied between the active electrodes and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply and to convert the system into the coagulation mode. In this mode, the active electrodes may be pressed against the severed vessel to provide sealing and/or coagulation of the vessel. Alternatively, a coagulation electrode located on the same or a different probe may be pressed against the severed vessel. Once the vessel is adequately sealed, the surgeon activates a control (e.g., another foot pedal) to increase the voltage of the power supply and convert the system back into the ablation mode.

The present invention is also useful for removing or ablating tissue around nerves, such as spinal or cranial nerves, e.g., the olfactory nerve on either side of the nasal cavity, the optic nerve within the optic and cranial canals, and the palatine nerve within the nasal cavity, soft palate, uvula and tonsil, etc. One of the significant drawbacks with prior art microdebriders and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation® process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Peripheral nerves usually comprise a connective tissue sheath, or epineurium, enclosing the bundles of nerve fibers to protect these nerve fibers. This protective tissue sheath typically comprises a fatty tissue (e.g., adipose tissue) having substantially different electrical properties than the normal target tissue, such as the turbinates, polyps, mucous tissue or the like, that are, for example, removed from the nose during sinus procedures. The system of the present invention measures the electrical properties of the tissue at the tip of the probe with one or more active electrode(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the active electrode(s), either individually or to the complete array of electrodes, if and when the tissue encountered at the tip or working end of the probe is normal tissue based on the measured electrical properties.

In one embodiment, the current limiting elements (discussed in detail below) are configured such that the active electrodes will shut down or turn off when the electrical impedance of tissue at the tip of the probe reaches a threshold level. When this threshold level is set to the impedance of the fatty tissue surrounding nerves, the active electrodes will shut off whenever they come in contact with, or in close proximity to, nerves. Meanwhile, the other active electrodes, which are in contact with or in close proximity to nasal tissue, will continue to conduct electric current to the return electrode. This selective ablation or removal of lower impedance tissue in combination with the Coblation® mechanism of the present invention allows the surgeon to precisely remove tissue around nerves or bone.

In addition to the above, applicant has discovered that the Coblation® mechanism of the present invention can be manipulated to ablate or remove certain tissue structures, while having little effect on other tissue structures. As discussed above, the present invention uses a technique of vaporizing electrically conductive fluid to form a plasma layer or pocket around the active electrode(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conductive liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine to form gaseous or liquid Coblation® by-products.

The energy evolved by the energetic electrons may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, components of adipose tissue have double bonds that require a substantially higher energy level than 4 to 5 eV to break. Accordingly, the present invention in its current configuration generally does not ablate or remove such fatty tissue. However, the present invention may be used to effectively ablate cells to release the inner fat content in a liquid form. Of course, factors may be changed such that these double bonds can be broken (e.g., increasing the voltage or changing the electrode configuration to increase the current density at the electrode tips).

In another aspect of the invention, a loop electrode is employed to resect, shape or otherwise remove tissue fragments from the treatment site, and one or more active electrodes are employed to ablate (i.e., break down the tissue by processes including molecular dissociation or disintegration) the non-ablated tissue fragments in situ. Once a tissue fragment is cut, partially ablated or resected by the loop electrode, one or more active electrodes will be brought into close proximity to these fragments (either by moving the probe into position, or by drawing the fragments to the active electrodes with a suction lumen). Voltage is applied between the active electrodes and the return electrode to volumetrically remove the fragments through molecular dissociation, as described above. The loop electrode and the active electrodes are preferably electrically isolated from each other such that, for example, current can be limited (passively or actively) or completely interrupted to the loop electrode as the surgeon employs the active electrodes to ablate tissue fragments (and vice versa).

In another aspect of the invention, the loop electrode(s) are employed to ablate tissue using the Coblation® mechanisms described above. In these embodiments, the loop electrode(s) provides a relatively uniform smooth cutting or ablation effect across the tissue. In addition, loop electrodes generally have a larger surface area exposed to electrically conductive fluid (as compared to the smaller active electrodes described above), which increases the rate of ablation of tissue. Preferably, the loop electrode(s) extend a sufficient distance from the electrode support member selected to achieve a desirable ablation rate, while minimizing power dissipation into the surrounding medium (which could cause undesirable thermal damage to surrounding or underlying tissue). In an exemplary embodiment, the loop electrode has a length from one end to the other end of about 0.5 to 20 mm, usually about 1 to 8 mm. The loop electrode usually extends about 0.25 to 10 mm from the distal end of the support member, preferably about 1 to 4 mm.

The loop electrode(s) may have a variety of cross-sectional shapes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be removed along the length of a solid or hollow wire electrode to form D or C shaped wires, respectively, with edges facing in the cutting direction. Alternatively, material can be removed at closely spaced intervals along the electrode length to form transverse grooves, slots, threads or the like along the electrodes.

In some embodiments, the loop electrode(s) will have a "non-active" portion or surface to selectively reduce undesirable current flow from the non-active portion or surface into tissue or surrounding electrically conductive liquids (e.g., isotonic saline, blood, or blood/non-conducting irrigant mixtures). Preferably, the "non-active" electrode portion will be coated with an electrically insulating material. This can be accomplished, for example, with plasma deposited coatings of an insulating material, thin-film deposition of an insulating material using evaporative or sputtering techniques (e.g., $SiO_2$ or $Si_3N_4$), dip coating, or by providing an electrically insulating support member to electrically insulate a portion of the external surface of the electrode. The electrically insulated non-active portion of the active electrode(s) allows the surgeon to selectively resect and/or ablate tissue, while minimizing necrosis or ablation of surrounding non-target tissue or other body structures.

In addition, the loop electrode(s) may comprise a single electrode extending from first and second ends to an insulating support in the shaft, or multiple, electrically isolated electrodes extending around the loop. One or more return electrodes may also be positioned along the loop portion. Further descriptions of these configurations can be found in U.S. application Ser. No. 08/687,792, filed on Jul. 18, 1996, now U.S. Pat. No. 5,843,019, which as already been incorporated herein by reference.

The electrosurgical probe will comprise a shaft or a handpiece having a proximal end and a distal end which supports one or more active electrode(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. The distal portion of the shaft may comprise a flexible material, such as plastics, malleable stainless steel, etc, so that the physician can mold the distal portion into different configurations for different applications. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Thus, the shaft will typically have a length of at least 5 cm for oral procedures and at least 10 cm, more typically being 20 cm, or longer for endoscopic procedures. The shaft will typically have a diameter of at least 0.5 mm and frequently in the range of from about 1 to 10 mm. Of course, for dermatological procedures on the outer skin, the shaft may have any suitable length and diameter that would facilitate handling by the surgeon.

For procedures within the nose and joints, the shaft will have a suitable diameter and length to allow the surgeon to reach the target by delivering the probe shaft through a percutaneous opening in the patient (e.g., a portal formed in the joint in arthroscopic surgery, or through one of the patient's nasal passages in FESS). Thus, the shaft will usually have a length in the range of from about 5 to 25 cm, and a diameter in the range of from about 0.5 to 5 mm. For procedures requiring the formation of a small hole or channel in tissue, such as treating swollen turbinates, the shaft diameter will usually be less than 3 mm, preferably less than about 1 mm. Likewise, for procedures in the ear, the shaft should have a length in the range of about 3 to 20 cm, and a diameter of about 0.3 to 5 mm. For procedures in the mouth or upper throat, the shaft will have any suitable length and diameter that would facilitate handling by the surgeon. For procedures in the lower throat, such as laryngectomies, the shaft will be suitably designed to access the larynx. For example, the shaft may be flexible, or have a distal bend to accommodate the bend in the patient's throat. In this regard, the shaft may be a rigid shaft having a specifically designed bend to correspond with the geometry of the mouth and throat, or it may have a flexible distal end, or it may be part of a catheter. In any of these embodiments, the shaft may also be introduced through rigid or flexible endoscopes. Specific shaft designs will be described in detail in connection with the figures hereinafter.

The current flow path between the active electrode(s) and the return electrode(s) may be generated by submerging the tissue site in an electrically conductive fluid (e.g., a viscous fluid, such as an electrically conductive gel), or by directing an electrically conductive fluid along a fluid path to the target site (i.e., a liquid, such as isotonic saline, or a gas, such as argon). This latter method is particularly effective in a dry environment (i.e., the tissue is not submerged in fluid) because the electrically conductive fluid provides a suitable current flow path from the active electrode to the return electrode. A more complete description of an exemplary method of directing electrically conductive fluid between the active and return electrodes is described in commonly assigned U.S. patent application Ser. No. 08/485,219, filed Jun. 7, 1995, now U.S. Pat. No. 5,697,281, the contents of which are incorporated by reference herein in their entirety for all purposes.

In some procedures, it may also be necessary to retrieve or aspirate the electrically conductive fluid after it has been directed to the target site. For example, in procedures in the nose, mouth or throat, it may be desirable to aspirate the fluid so that it does not flow down the patient's throat. In addition, it may be desirable to aspirate small pieces of tissue that are not completely disintegrated by the high frequency energy, air bubbles, or other fluids at the target site, such as blood, mucus, the gaseous products of ablation, etc. Accordingly, the system of the present invention can include a suction lumen in the probe, or on another instrument, for aspirating fluids from the target site.

In some embodiments, the probe will include one or more aspiration electrode(s) coupled to the distal end of the suction lumen for ablating, or at least reducing the volume of, tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. In some embodiments, the probe will be designed to use suction force to draw loose tissue, such as synovial tissue to the aspiration or ablation electrode(s) on the probe, which are then energized to ablate the loose tissue.

In other embodiments, the aspiration lumen can be positioned proximal of the active electrodes a sufficient distance such that the aspiration lumen will primarily aspirate air bubbles and body fluids such as blood, mucus, or the like. Such a configuration allows the electrically conductive fluid to dwell at the target site for a longer period. Consequently, the plasma can be created more aggressively at the target site and the tissue can be treated in a more efficient manner. Additionally, by positioning the aspiration lumen opening somewhat distant from the active electrodes, it may not be necessary to have ablation electrodes at the lumen opening since, in this configuration, tissue fragments will typically not be aspirated through the lumen.

The present invention may use a single active electrode or an electrode array distributed over a contact surface of a probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment. Such unwanted application of electrical energy results from power dissipation into surrounding electrically conductive liquids, such as blood, normal saline, electrically conductive gel and the like. The active electrodes may be independently current-limited by isolating the terminals from each other and connecting each terminal to a separate power source that is isolated from the other active electrodes. Alternatively, the active electrodes may be connected to each other at either the proximal or distal ends of the probe to form a single connector that couples to a power source.

In one configuration, each individual active electrode in the electrode array is electrically insulated from all other active electrodes in the array within the probe and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the probe, connectors, cable, controller, or along the conductive path from the controller to the distal tip of the probe. Alternatively, the resistance and/or capacitance may occur on the surface of the active electrode(s) due to oxide layers which form selected active electrodes (e.g., titanium or a resistive coating on the surface of metal, such as platinum).

The tip region of the probe may comprise many independent active electrodes designed to deliver electrical energy in the vicinity of the tip. The selective application of electrical energy to the conductive fluid is achieved by connecting each individual active electrode and the return electrode to a power source having independently controlled or current limited channels. The return electrode(s) may comprise a single tubular member of conductive material proximal to the electrode array at the tip which also serves as a conduit for the supply of the electrically conductive fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the active electrodes with conduction of high frequency current from each individual active electrode to the return electrode. The current flow from each individual active electrode to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the active electrode(s) for appropriate time intervals effects cutting, removing, ablating, shaping, contracting or otherwise modifying the target tissue. The tissue volume over which energy is dissipated (i.e., over which a high current density exists) may be precisely controlled, for example, by the use of a multiplicity of small active electrodes whose effective diameters or principal dimensions range from about 5 mm to 0.01 mm, preferably from about 2 mm to 0.05 mm, and more preferably from about 1 mm to 0.1 mm. In these embodiments, electrode areas for both circular and non-circular terminals will have a contact area (per active electrode) below 25 mm$^2$, preferably being in the range from 0.0001 mm$^2$ to 1 mm$^2$, and more preferably from 0.005 mm$^2$ to 0.5 mm$^2$. The circumscribed area of the electrode array is in the range from 0.25 mm$^2$ to 75 mm$^2$, preferably from 0.5 mm to 40 mm$^2$, and will usually include at least two isolated active electrodes, preferably at least five active electrodes, often greater than 10 active electrodes and even 50 or more active electrodes, disposed over the distal contact surfaces on the shaft. The use of small diameter active electrodes increases the electric field intensity and reduces the extent or depth of tissue heating as a consequence of the divergence of current flux lines which emanate from the exposed surface of each active electrode.

The area of the tissue treatment surface can vary widely, and the tissue treatment surface can assume a variety of geometries, with particular areas and geometries being selected for specific applications. Active electrode surfaces can have areas in the range from 0.25 mm$^2$ to 75 mm$^2$, usually being from about 0.5 mm$^2$ to 40 mm$^2$. The geometries can be planar, concave, convex, hemispherical, conical, linear "in-line" array or virtually any other regular or irregular shape. Most commonly, the active electrode(s) or active electrode(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

The electrically conductive fluid should have a threshold conductivity to provide a suitable conductive path between the active electrode(s) and the return electrode(s). The electrical conductivity of the fluid (in units of millisiemens per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the active electrode(s) and the return electrode(s) to maintain the conductive path therebetween. In addition, this will help to maintain a vapor or plasma layer between the active electrode(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The voltage applied between the return electrode(s) and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed at about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular FESS procedure, arthroscopic surgery, dermatological procedure, ophthalmic procedures, open surgery or other endoscopic surgery procedure. A description of a suitable power source can be found in U.S. Patent Application No. 60/062,997, filed Oct. 23, 1997, the complete disclosure of which has been incorporated herein by reference.

The power source may be current limited or otherwise controlled so that undesired heating of the target tissue or surrounding (non-target) tissue does not occur. In one embodiment of the present invention, current limiting inductors are placed in series with each independent active electrode, where the inductance of the inductor is in the range of 10uH to 50,000uH, depending on the electrical properties of the target tissue, the desired tissue heating rate, and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or conductive gel), the resistance of the current limiting resistor increases significantly, thereby minimizing the power delivery from the active electrode into the low resistance medium (e.g., saline irrigant or conductive gel).

It should be clearly understood that the invention is not limited to electrically isolated active electrodes, or even to a plurality of active electrodes. For example, the array of active electrodes may be connected to a single lead that extends through the probe shaft to a power source of high frequency current. Alternatively, the probe may incorporate a single electrode that extends directly through the probe shaft or is connected to a single lead that extends to the power source. The active electrode may have a ball shape (e.g., for tissue vaporization and desiccation), a twizzle shape (for vaporization and needle-like cutting), a spring shape (for rapid tissue debulking and desiccation), a twisted metal shape, an annular or solid tube shape or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode or the like. In one embodiment, the probe comprises a single active electrode that extends from an insulating member, e.g., ceramic, at the distal end of the probe. The insulating member is preferably a tubular structure that separates the active electrode from a tubular or annular return electrode positioned proximal to the insulating member and the active electrode.

Figure 2:
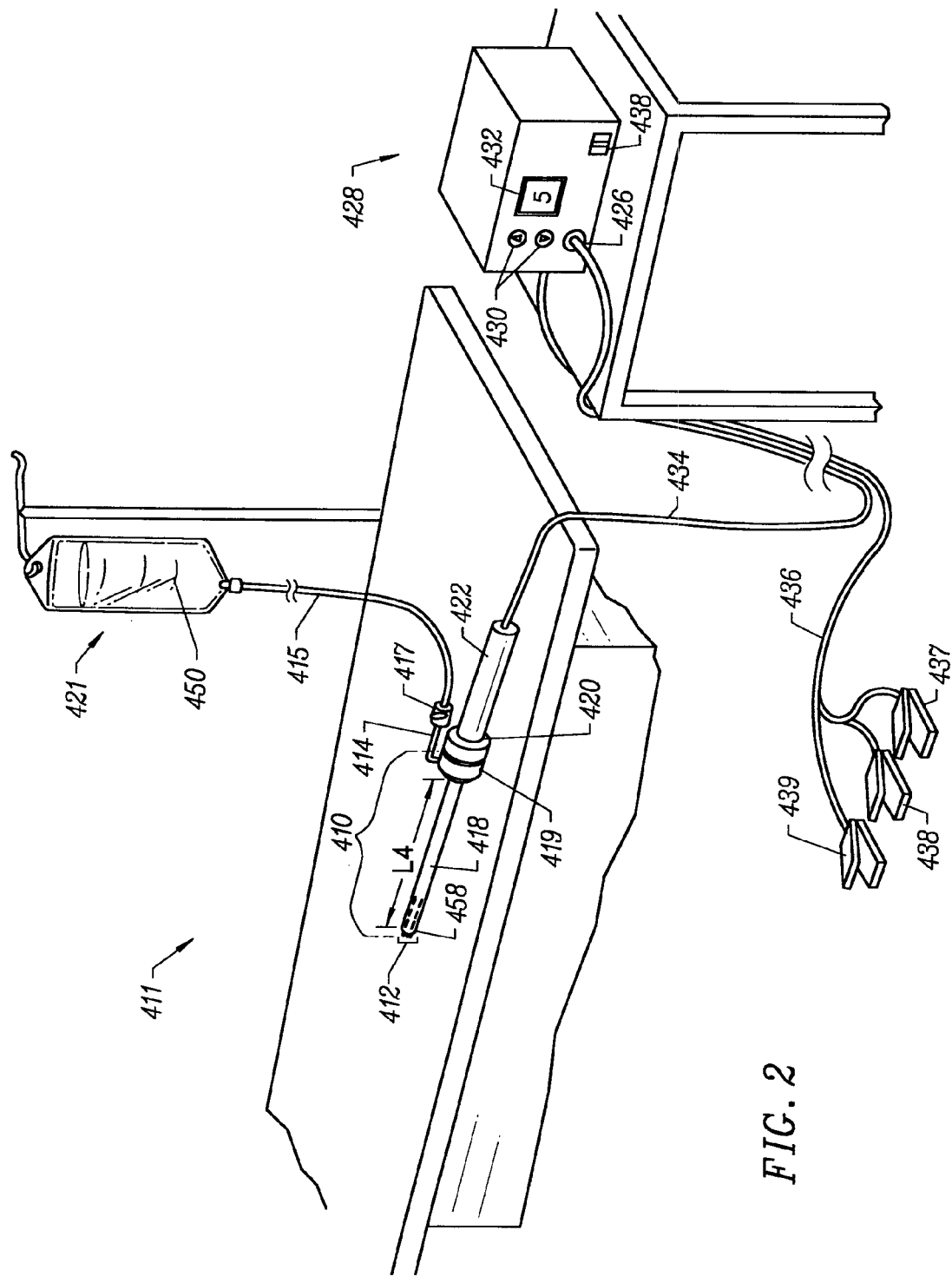
FIG. 2 is a perspective view of another electrosurgical system incorporating a power supply, an electrosurgical probe and a supply of electrically conductive fluid for delivering the fluid to the target site.

Referring now to FIG. 2, an exemplary electrosurgical system 411 for treatment of tissue in 'dry fields' will now be described in detail. Of course, system 411 may also be used in a 'wet field', i.e., the target site is immersed in electrically conductive fluid. However, this system is particularly useful in 'dry fields' where the fluid is preferably delivered through an electrosurgical probe to the target site. As shown, electrosurgical system 411 generally comprises an electrosurgical handpiece or probe 410 connected to a power supply 428 for providing high frequency voltage to a target site and a fluid source 421 for supplying electrically conductive fluid 450 to probe 410. In addition, electrosurgical system 411 may include an endoscope (not shown) with a fiber optic head light for viewing the surgical site, particularly in sinus procedures or procedures in the ear or the back of the mouth. The endoscope may be integral with probe 410, or it may be part of a separate instrument. The system 411 may also include a vacuum source (not shown) for coupling to a suction lumen or tube in the probe 410 for aspirating the target site.

As shown, probe 410 generally includes a proximal handle 419 and an elongate shaft 418 having an array 412 of active electrodes 458 at its distal end. A connecting cable 434 has a connector 426 for electrically coupling the active electrodes 458 to power supply 428. The active electrodes 458 are electrically isolated from each other and each of the terminals 458 is connected to an active or passive control network within power supply 428 by means of a plurality of individually insulated conductors (not shown). A fluid supply tube 415 is connected to a fluid tube 414 of probe 410 for supplying electrically conductive fluid 450 to the target site.

Similar to the above embodiment, power supply 428 has an operator controllable voltage level adjustment 430 to change the applied voltage level, which is observable at a voltage level display 432. Power supply 428 also includes first, second and third foot pedals 437, 438, 439 and a cable 436 which is removably coupled to power supply 428. The foot pedals 437, 438, 439 allow the surgeon to remotely adjust the energy level applied to active electrodes 458. In an exemplary embodiment, first foot pedal 437 is used to place the power supply into the ablation mode and second foot pedal 438 places power supply 428 into the "coagulation" mode. The third foot pedal 439 allows the user to adjust the voltage level within the "ablation" mode. In the ablation mode, a sufficient voltage is applied to the active electrodes to establish the requisite conditions for molecular dissociation of the tissue (i.e., vaporizing a portion of the electrically conductive fluid, ionizing charged particles within the vapor layer, and accelerating these charged particles against the tissue). As discussed above, the requisite voltage level for ablation will vary depending on the number, size, shape and spacing of the electrodes, the distance to which the electrodes extend from the support member, etc. Once the surgeon places the power supply in the ablation mode, voltage level adjustment 430 or third foot pedal 439 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 428 applies a low enough voltage to the active electrodes (or the coagulation electrode) to avoid vaporization of the electrically conductive fluid and subsequent molecular dissociation of the tissue. The surgeon may automatically toggle the power supply between the ablation and coagulation modes by alternately stepping on foot pedals 437, 438, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply actuate foot pedal 438, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by actuating foot pedal 437. A specific design of a suitable power supply for use with the present invention can be found in Provisional Patent Application No. 60/062,997 filed Oct. 23, 1997, previously incorporated herein by reference.

Figure 3:
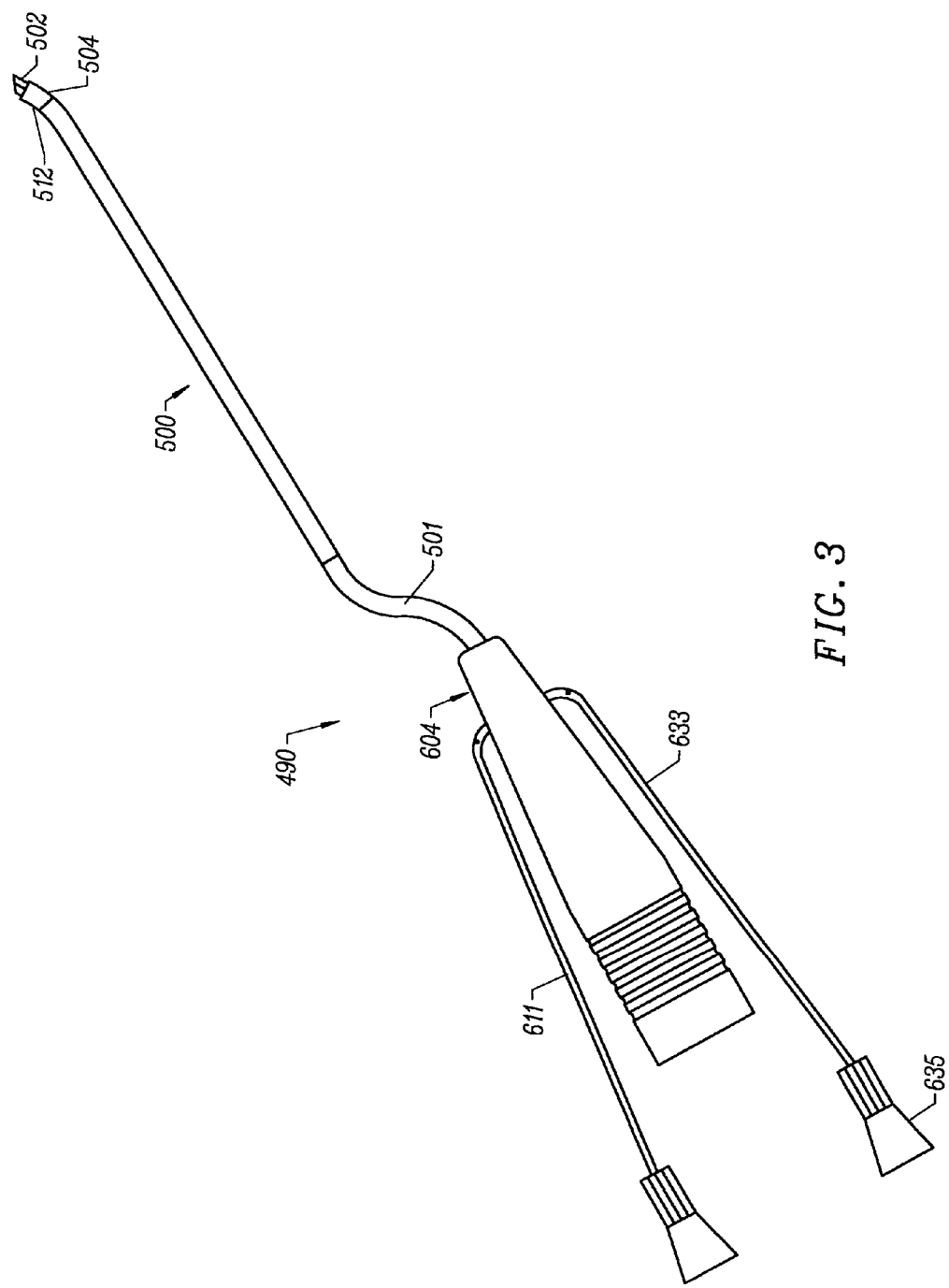
FIG. 3 is a side view of another electrosurgical probe according to the present invention incorporating aspiration electrodes for ablating aspirated tissue fragments and/or tissue strands, such as synovial tissue.
Figure 4:
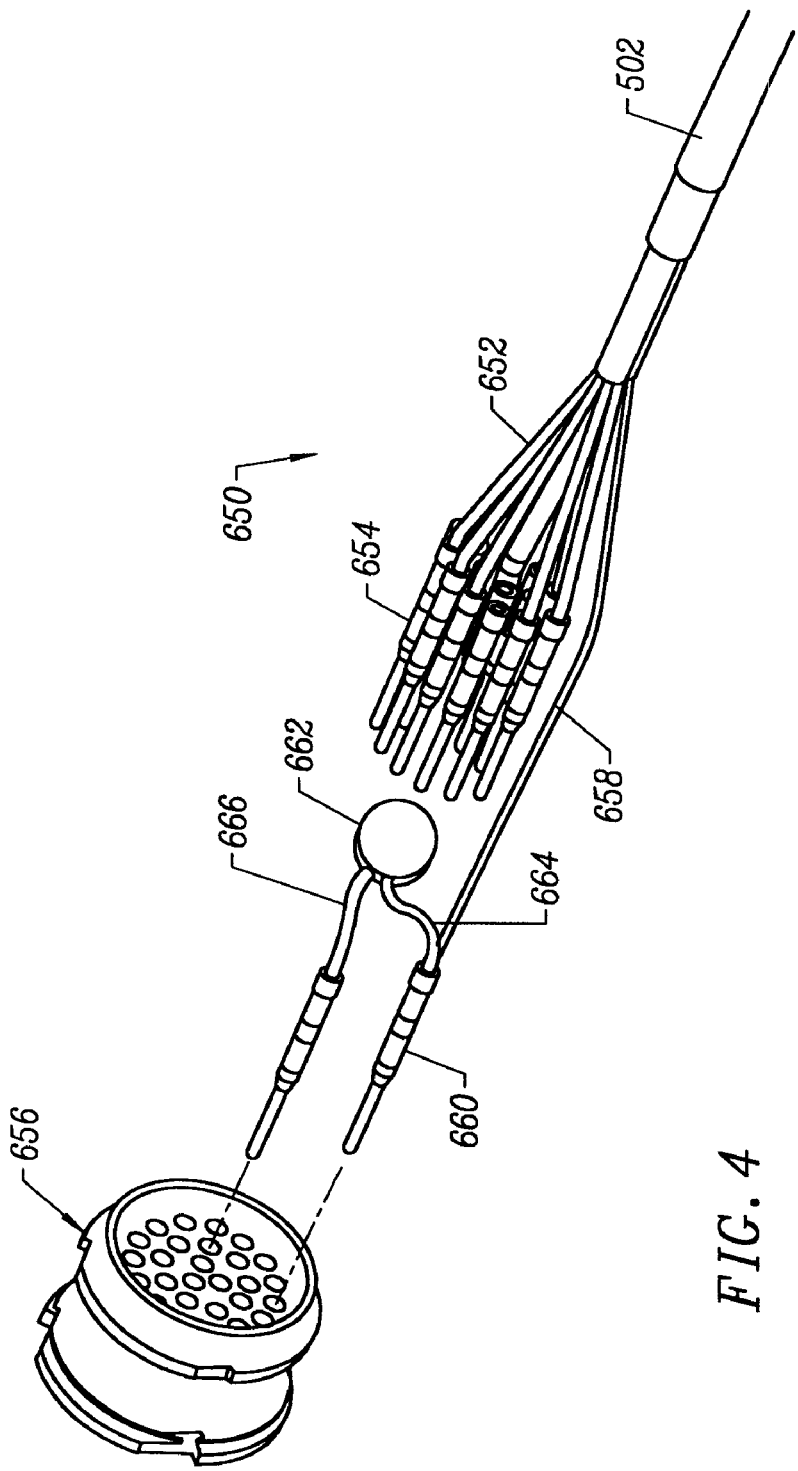
FIG. 4 is an exploded view of a proximal portion of the electrosurgical probe.

FIGS. 3 and 4 illustrate an exemplary electrosurgical probe 490 constructed according to the principles of the present invention. As shown in FIG. 3, probe 490 generally includes an elongated shaft 500 which may be flexible or rigid, a handle 604 coupled to the proximal end of shaft 500 and an electrode support member 502 coupled to the distal end of shaft 500. Shaft 500 preferably includes a bend 501 that allows the distal section of shaft 500 to be offset from the proximal section and handle 604. This offset facilitates procedures that require an endoscope, such as FESS, because the endoscope can, for example, be introduced through the same nasal passage as the shaft 500 without interference between handle 604 and the eyepiece of the endoscope. In one embodiment, shaft 500 preferably comprises a plastic material that is easily molded into the desired shape.

In an alternative embodiment (not shown), shaft 500 comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 500 includes an electrically insulating jacket 508 which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact.

Handle 604 typically comprises a plastic material that is easily molded into a suitable shape for handling by the surgeon. Handle 604 defines an inner cavity (not shown) that houses the electrical connections 650 (FIG. 4), and provides a suitable interface for connection to an electrical connecting cable 422 (see FIG. 2). Electrode support member 502 extends from the distal end of shaft 500 (usually about 1 to 20 mm), and provides support for a plurality of electrically isolated active electrodes 504. As shown in FIG. 3, a fluid tube 633 extends through an opening in handle 604, and includes a connector 635 for connection to a fluid supply source, for supplying electrically conductive fluid to the target site. Depending on the configuration of the distal surface of shaft 500, fluid tube 633 may extend through a single lumen (not shown) in shaft 500, or it may be coupled to a plurality of lumens (also not shown) that extend through shaft 500 to a plurality of openings at its distal end. In the representative embodiment, fluid tube 633 extends along the exterior of shaft 500 to a point just proximal of return electrode 512. In this embodiment, the fluid is directed through an opening 637 past return electrode 512 to the active electrodes 504. Probe 490 may also include a valve 417 (FIG. 3) or equivalent structure for controlling the flow rate of the electrically conductive fluid to the target site.

In several variations of the invention, a return electrode is not directly connected to the active electrode or. To complete this current path so that active electrode(s) are electrically connected to return electrode, electrically conductive fluid (e.g., isotonic saline) is caused to flow therebetween. The electrically conductive fluid may be delivered through a fluid tube (see, e.g., FIG. 3, element 633) to an opening near the distal end of the device. Alternatively, the fluid may be delivered by a fluid delivery element that is separate from probe. In arthroscopic surgery, for example, the joint cavity will be flooded with isotonic saline and the probe will be introduced into this flooded cavity. Electrically conductive fluid will be continually resupplied to maintain the conduction path between return electrode and active electrodes.

In alternative embodiments, the fluid path may be formed in probe by, for example, an inner lumen or an annular gap between the return electrode and a tubular support member within a shaft of the device. This annular gap may be formed near the perimeter of the shaft such that the electrically conductive fluid tends to flow radially inward towards the target site, or it may be formed towards the center of the shaft so that the fluid flows radially outward. In both of these embodiments, a fluid source (e.g., a bag of fluid elevated above the surgical site or having a pumping device), is coupled to probe via a fluid supply tube that may or may not have a controllable valve. A more complete description of an electrosurgical probe incorporating one or more fluid lumen(s) can be found in parent patent application Ser. No. 08/485,219, filed on Jun. 7, 1995, now U.S. Pat. No. 5,697,281, the complete disclosure of which is incorporated herein by reference.

FIG. 4 illustrates the electrical connections 650 within handle 604 for coupling active electrodes 504 and return electrode 512 to the power supply 428. As shown, a plurality of wires 652 extend through shaft 500 to couple terminals 504 to a plurality of pins 654, which are plugged into a connector block 656 for coupling to a connecting cable 422 (FIG. 2). Similarly, return electrode 512 is coupled to connector block 656 via a wire 658 and a plug 660. Alternatively, the device may have an integrated cable fixedly attached to the connections where the proximal portion of the cable (the end of the cable opposite to the device) contains connections allowing for coupling of the device to a power supply.

Figure 5:
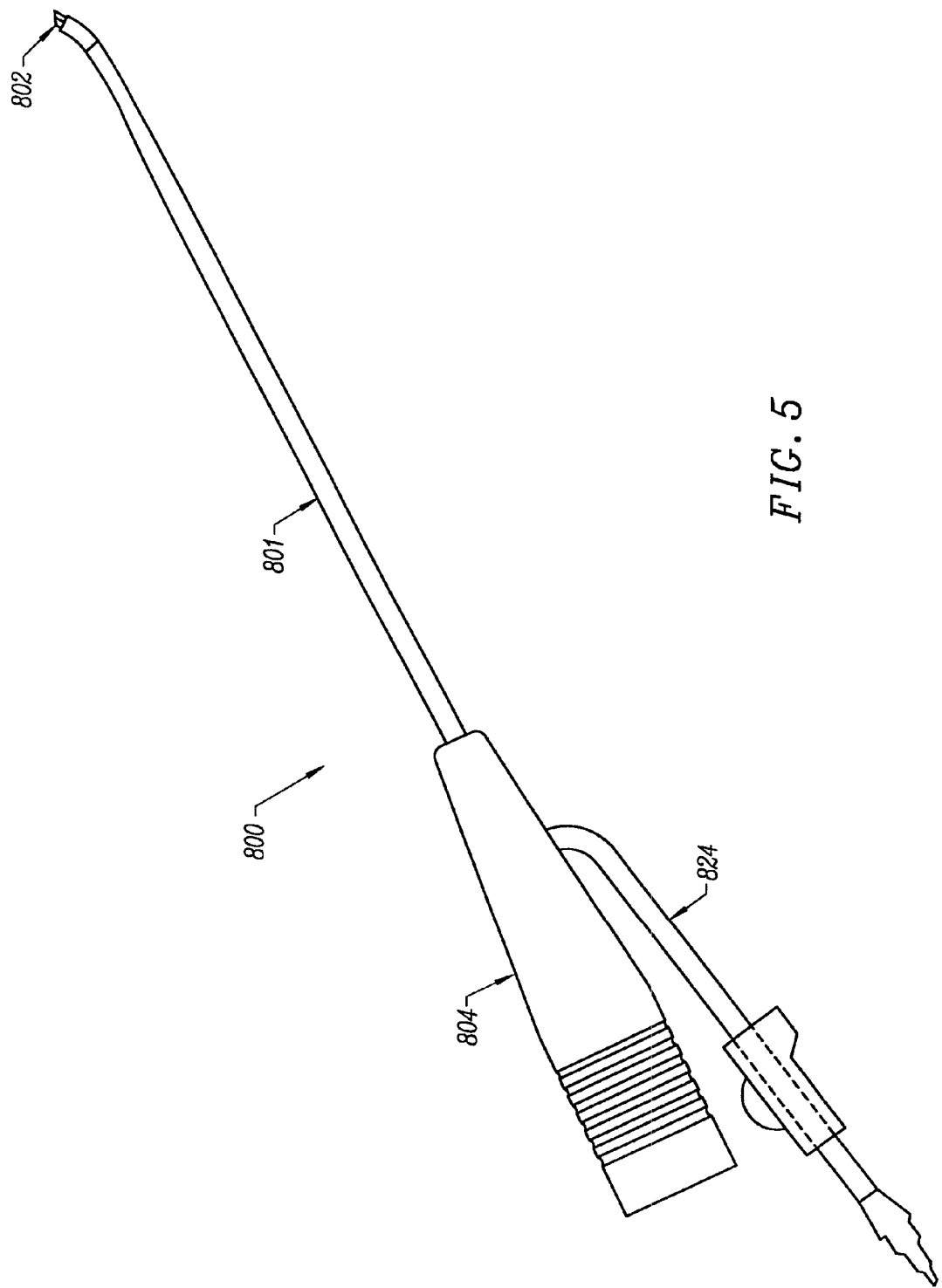
FIG. 5 is a perspective view of another embodiment of the present invention.
Figure 6:
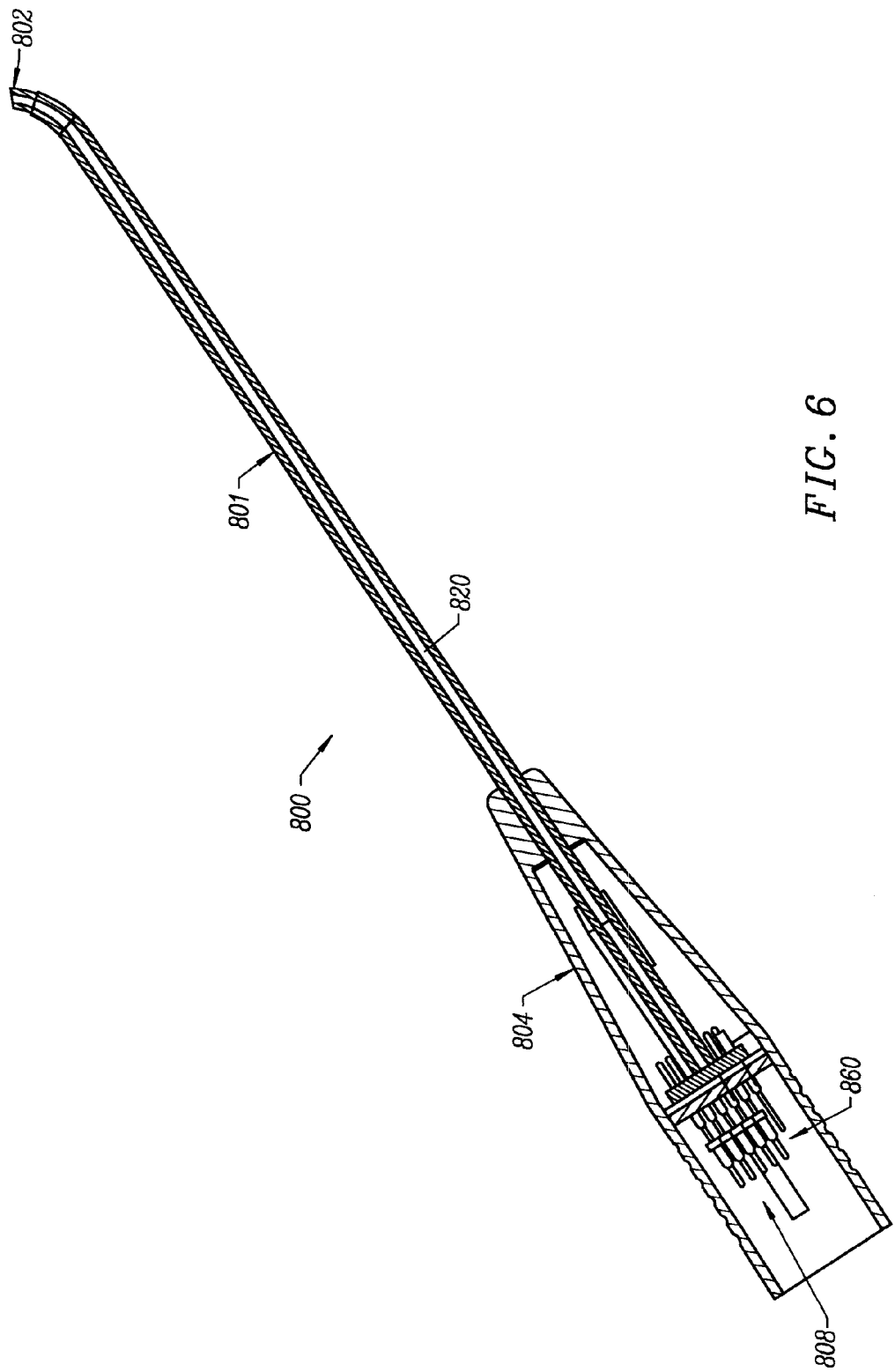
FIG. 6 is a side-cross-sectional view of the electrosurgical probe of FIG. 5.
Figure 7:
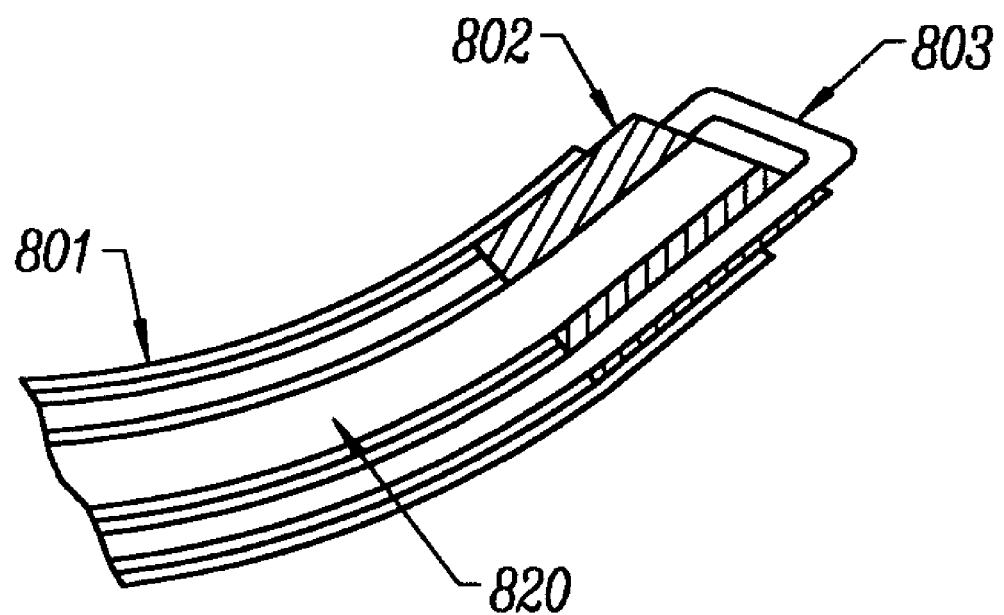
FIG. 7 is an enlarged detailed cross-sectional view of the distal end portion of the probe of FIG. 5.
Figure 8:
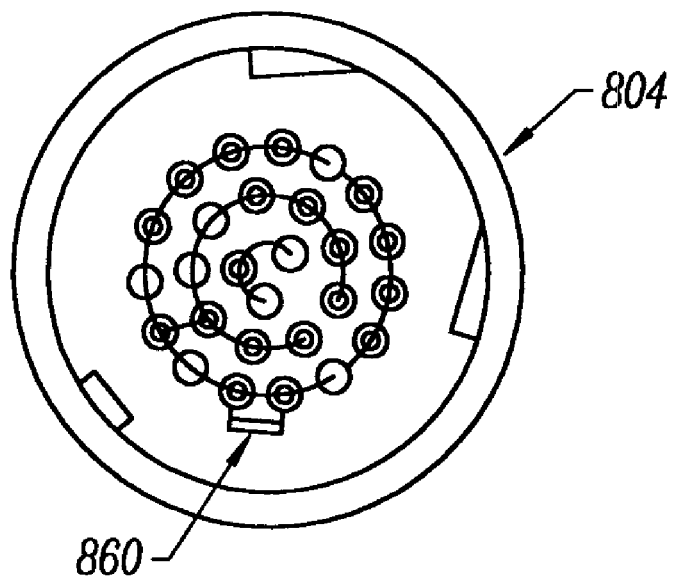
FIGS. 8 and 9 show the proximal end and the distal end, respectively, of the probe of FIG. 5.
Figure 9:
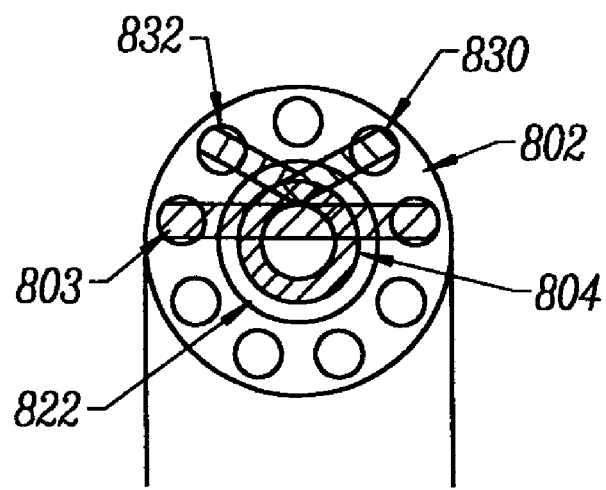
Figure 10:
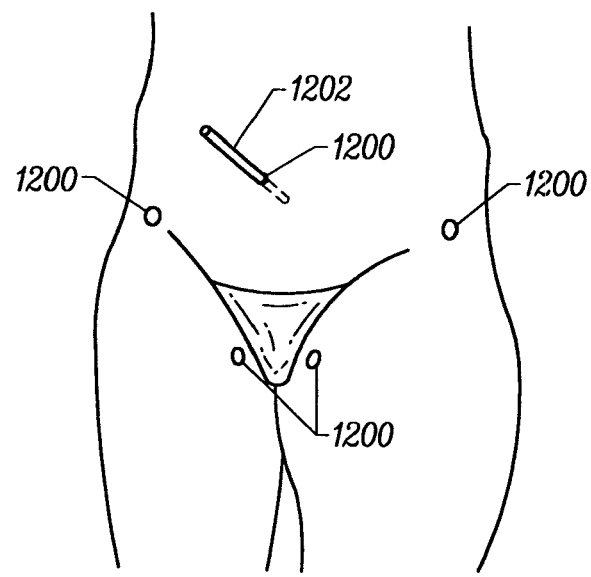
FIG. 10 illustrates a method for removing fatty tissue from the abdomen, groin or thigh region of a patient according to the present invention.
Figure 11:
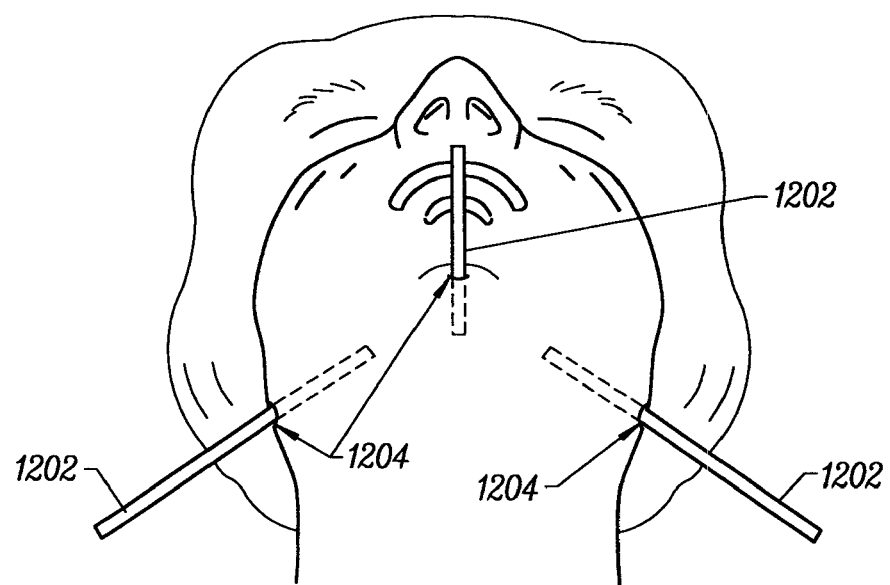
FIG. 11 illustrates a method for removing fatty tissue in the head and neck region of a patient according to the present invention.

FIGS. 5-9 illustrate another embodiment of the present invention. As shown in FIG. 5, an electrosurgical probe 800 includes an elongated shaft 801 which may be flexible or rigid, a handle 804 coupled to the proximal end of shaft 801 and an electrode support member 802 coupled to the distal end of shaft 801. As in previous embodiments, probe 800 includes an active loop electrode 803 (e.g., FIG. 7) and a return electrode 812 (not shown), the latter spaced proximally from active loop electrode 803. The probe 800 further includes a suction lumen 820 (FIG. 6) for aspirating excess fluids, bubbles, tissue fragments, and/or products of ablation from the target site. As shown in FIGS. 6 and 9, suction lumen 820 extends through support member 802 to a distal opening 822, and extends through shaft 801 and handle 804 to an external connector 824 for coupling to a vacuum source. Typically, the vacuum source is a standard hospital pump that provides suction pressure to connector 824 and lumen 820.

As shown in FIG. 6, handle 804 defines an inner cavity 808 that houses the electrical connections 850 (discussed above), and provides a suitable interface for connection to an electrical connecting cable 22 (see FIG. 1). As shown in FIG. 8, the probe will also include a coding resistor 860 having a value selected to program different output ranges and modes of operation for the power supply. This allows a single power supply to be used with a variety of different probes in different applications (e.g., dermatology, cardiac surgery, neurosurgery, arthroscopy, etc).

Electrode support member 802 extends from the distal end of shaft 801 (usually about 1 to 20 mm), and provides support for loop electrode 803 and a ring electrode 804 (see FIG. 9). As shown in FIG. 7, loop electrode 803 has first and second ends extending from the electrode support member 802. The first and second ends are each coupled to, or integral with, one or more connectors, e.g., wires (not shown), that extend through the shaft of the probe to its proximal end for coupling to the high frequency power supply. The loop electrode usually extends about 0.5 to about 10 mm from the distal end of support member, preferably about 1 to 2 mm. Loop electrode 803 usually extends further away from the support member than the ring electrode 804 to facilitate ablation of tissue. As discussed below, loop electrode 803 is especially configured for tissue ablation, while the ring electrode 804 ablates tissue fragments that are aspirated into suction lumen 820.

Referring to FIG. 9, ring electrode 804 preferably comprises a tungsten or titanium wire having two ends 830, 832 coupled to electrical connectors (not shown) within support member 802. The wire is bent to form one-half of a figure eight, thereby forming a ring positioned over opening 822 of suction lumen 820. This inhibits passage of tissue fragments large enough to clog suction lumen 820. Moreover, voltages applied between ring electrode 804 and return electrode 812 provide sufficient energy to ablate these tissue fragments into smaller fragments that are then aspirated through lumen 820. In a presently preferred embodiment, ring electrode 804 and loop electrode 803 are electrically isolated from each other. However, electrodes 804, 803 may be electrically coupled to each other in some applications.

The systems of the present invention may include a bipolar arrangement of electrodes designed to ablate tissue at the target site, and then aspirate tissue fragments, as described above. Alternatively, the instrument may also include a rotating shaft with a cutting tip for cutting tissue in a conventional manner. In this embodiment, the electrode(s) serve to effect hemostasis at the target site and to reduce clogging of the aspiration lumen, while the rotating shaft and cutting tip do the bulk of tissue removal by cutting the tissue in a conventional manner.

The system and method of the present invention may also be useful to efficaciously ablate (i.e., disintegrate) cancer cells and tissue containing cancer cells, such as cancer on the surface of the epidermis, eye, colon, bladder, cervix, uterus and the like. The present invention's ability to completely disintegrate the target tissue can be advantageous in this application because simply vaporizing and fragmenting cancerous tissue may lead to spreading of viable cancer cells (i.e., seeding) to other portions of the patient's body or to the surgical team in close proximity to the target tissue. In addition, the cancerous tissue can be removed to a precise depth while minimizing necrosis of the underlying tissue.

In another aspect, the present invention provides an electrosurgical probe having at least one active loop electrode for resecting and ablating tissue. In comparison to the planar electrodes, ball electrodes, or the like, the active loop electrodes provide a greater current concentration to the tissue at the target site. The greater current concentration can be used to aggressively create a plasma within the electrically conductive fluid, and hence a more efficient resection of the tissue at the target site. In use, the loop electrode(s) are typically employed to ablate tissue using the Coblation® mechanisms as described above. Voltage is applied between the active loop electrodes and a return electrode to volumetrically loosen fragments from the target site through molecular dissociation. Once the tissue fragments are loosened from the target site, the tissue fragments can be ablated in situ within the plasma (i.e., break down the tissue by processes including molecular dissociation or disintegration).

In some embodiments, the loop electrode(s) provide a relatively uniform smooth cutting or ablation effect across the tissue. The loop electrodes generally have a larger surface area exposed to electrically conductive fluid (as compared to the smaller active electrodes described above), which increases the rate of ablation of tissue.

Applicants have found that the current concentrating effects of the loop electrodes further provide reduced current dissipation into the surrounding tissue, and consequently improved patient comfort through the reduced stimulation of surrounding nerves and muscle. Preferably, the loop electrode(s) extend a sufficient distance from the electrode support member to achieve current concentration and an improved ablation rate while simultaneously reducing current dissipation into the surrounding medium (which can cause undesirable muscle stimulation, nerve stimulation, or thermal damage to surrounding or underlying tissue). In an exemplary embodiment, the loop electrode has a length from one end to the other end of about 0.5 mm to 20 mm, usually about 1 mm to 8 mm. The loop electrode usually extends about 0.25 mm to 10 mm from the distal end of the support member, preferably about 1 mm to 4 mm.

The loop electrode(s) may have a variety of cross-sectional shapes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be removed along the length of a solid or hollow wire electrode to form D or C shaped wires, respectively, with edges facing in the cutting direction. Alternatively, material can be removed at closely spaced intervals along the electrode length to form transverse grooves, slots, threads or the like along the electrodes.

In yet another aspect, the present invention provides an electrosurgical probe having an aspiration lumen with an opening that is spaced proximally from the active electrodes. Applicants have found that, by spacing the suction lumen opening proximal of the active electrodes, a more aggressive plasma can be created. In use, the saline is delivered to the target site and allowed to remain in contact with the electrodes and tissue for a longer period of time. By increasing the distance between the aspiration lumen and the conductive fluid, the dwell time of the conductive fluid is increased and the plasma can be aggressively created. Advantageously, by moving the aspiration lumen out of the target area, the suction will primarily aspirate blood and gas bubbles from the target site, while leaving the conductive fluid in the target area. Consequently, less conductive fluid and tissue fragments are aspirated from the target site and less clogging of the aspiration lumen occurs.

In a further aspect, the present invent provides an electrosurgical probe having a conductive fluid delivery lumen that has at least one distal opening positioned at least partially around the active electrodes. The configuration of the openings can be completely around the active electrodes (e.g., 0 configuration or annular shaped) or partially around the active electrodes (e.g., U configuration or C configuration) such that delivery of the conductive fluid immerses the active electrodes with conductive fluid during the ablation or resection procedure. Because the conductive fluid can be delivered from a plurality of directions, the dwell time of the conductive fluid is increased, and consequently the creation of the plasma can be improved.

In a preferred embodiment, the conductive fluid lumen comprises a plurality of openings that are positioned so as to substantially surround the active electrode array. As above, by "substantially surround", is meant that the openings are at least partially around the active electrodes. In some configurations, the openings will be equally spaced around the active electrodes. However, it will be appreciated that in other alternative embodiments, the openings will only partially surround the active electrodes or can be unevenly spaced about the active electrodes.

With reference to FIGS. 12-19I there follows a description of an electrosurgical probe 1400 including a resection unit 1406, according to various embodiments of the instant invention. Probe 1400 is adapted for aggressive ablation, for resection, or for combined ablation and resection of tissue. Probe 1400 may be used in a broad range of surgical procedures including, without limitation, those listed or described hereinabove. In some embodiments, resection unit 1406 may be used to resect tissue by mechanical abrasion, cutting, or severing of tissue. In some embodiments, resection unit 1406 may be used to ablate tissue, e.g., via a Coblation® (cool ablation) mechanism. The Coblation® mechanism has been described hereinabove. Briefly, and without being bound by theory, Coblation® involves the localized generation of a plasma by the application of a high frequency voltage between at least one active electrode and a return electrode in the presence of an electrically conductive fluid. The plasma thus generated causes the breakdown of tissues, e.g., via molecular dissociation, to form low molecular weight ablation by-products. Such low molecular weight ablation by-products may be easily removed from a target site, e.g., via aspiration. Coblation® allows the controlled removal of tissue, in which both the quantity and quality of tissue removed can be accurately determined. In some embodiments, resection unit 1406 may be used for combined resection and ablation: to resect tissue by application of a mechanical force to the tissue and, concurrently therewith, to electrically ablate ("Coblate") the tissue contacted by resection unit 1406. Applicants have found that a combination of mechanical resection and electrical ablation by resection unit 1406 provides advantageous tissue removal, as compared with mechanical resection or electrical ablation alone. Advantages of tissue removal by combined resection and ablation by resection unit 1406 include a more rapid and aggressive tissue removal, as compared with ablation alone; and a more controlled and less traumatic tissue removal, as compared with mechanical resection alone.

Figure 12:
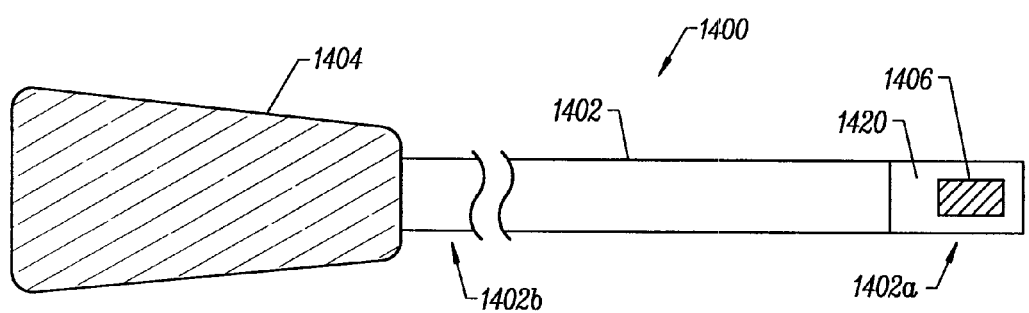
FIG. 12 shows an electrosurgical probe including a resection unit, according to another embodiment of the invention.
Figure 13:
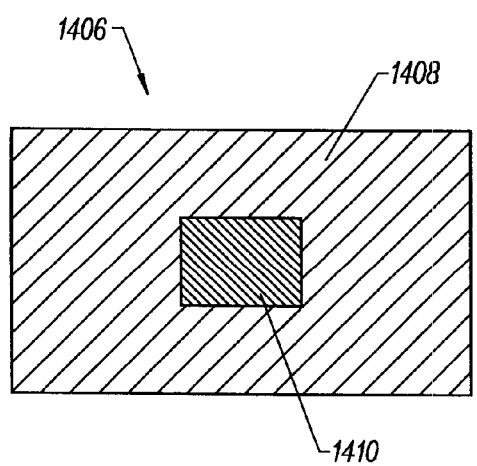
FIG. 13 shows a resection unit of an electrosurgical probe, the resection unit including a resection electrode on a resection electrode support.

FIG. 12 shows probe 1400 including a shaft 1402 affixed at shaft proximal end portion 1402b to a handle 1404. Resection unit 1406 is disposed on shaft distal end portion 1402a. Although FIG. 12 shows only a single resection unit 1406 on shaft 1402, certain embodiments of the instant invention may include a plurality of resection units 1406 which may be alike or dissimilar in various respects (for example, the size and shape of electrode support 1408, and the number, arrangement, and type of resection electrodes 1410) (FIG. 13). In the embodiment of FIG. 12, a return electrode 1420 is located at shaft distal end portion 1402a. Return electrode 1420 may be in the form of an annular band. Resection unit 1406 is shown in FIG. 12 as being arranged within, or surrounded by, return electrode 1420. In other embodiments, resection unit 1406 may be arranged adjacent to return electrode 1420. Under the invention, shaft 1402 may be provided in a range of different lengths and diameters. Preferably, shaft 1402 has a length in the range of from about 5 cm to about 30 cm; more preferably in the range of from about 10 cm to about 25 cm. Preferably, shaft 1402 has a diameter in the range of from about 1 mm to about 20 mm; more preferably in the range of from about 2 mm to about 10 mm.

FIG. 13 schematically represents resection unit 1406 of probe 1400, wherein resection unit 1406 includes a resection electrode 1410 on a resection electrode support member 1408. In FIG. 13 resection electrode 1410 is represented as a single "box" located within support 1408, however, other arrangements and numbers of resection electrode 1410 are contemplated and are within the scope of the invention (see, for example, FIGS. 16A-F). Resection electrode support 1408 may comprise an electrically insulating, and durable or refractory material, such as a glass, a ceramic, a silicone, a polyurethane, a urethane, a polyimide, silicon nitride, teflon, or alumina, and the like. Resection electrode support 1408 is shown in FIG. 13 as being substantially square in outline, however, a broad range of other shapes are also possible. The size of resection electrode support 1408 may depend on a number of factors, including the diameter or width of shaft 1402. In one embodiment, support 1408 may be mounted laterally on shaft 1402 as an annular band, i.e., support 1408 may completely encircle shaft 1402. Typically support 1408 represents or occupies from about 2% to 100% of the circumference of shaft 1402. More typically, support 1408 occupies from about 50% to 80% of the circumference of shaft 1402, most typically from about 10% to 50% of the circumference of shaft 1402. In embodiments wherein support 1408 is mounted terminally on shaft 1402, support 1408 typically occupies from about 5% to 100% of the cross-sectional area of shaft 1402, more typically from about 10% to 95% of the cross-sectional area of shaft 1402.

FIGS. 14A-D each show an electrosurgical probe 1400, according to certain embodiments of the invention. Probe 1400 is depicted in FIGS. 14A-D as being linear, however, according to various embodiments of the invention, shaft 1402 may include one or more curves or bends therein (see, for example, FIGS. 34A-B). Resection electrodes 1410 are omitted from FIGS. 14A-D for the sake of clarity. However, as described elsewhere herein, each resection unit 1406 includes at least one resection electrode 1410 (see, for example, FIGS. 16A-F, 18A-D).

Figure 14A:
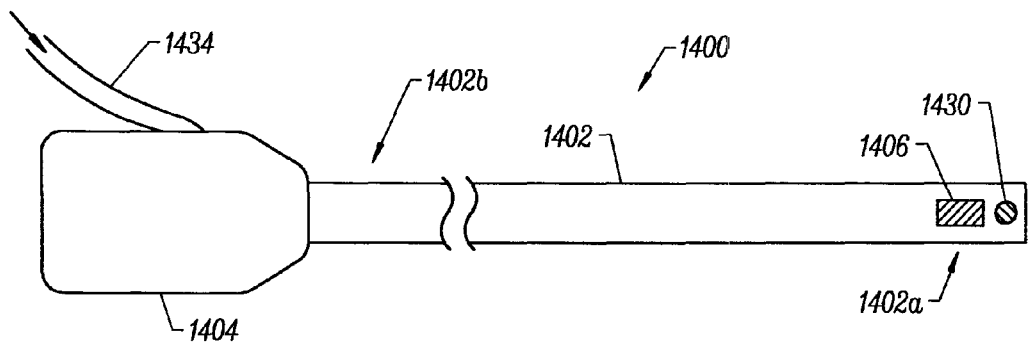
FIGS. 14A-D each show an electrosurgical probe including a resection unit, according to various embodiments of the invention.
Figure 15A:
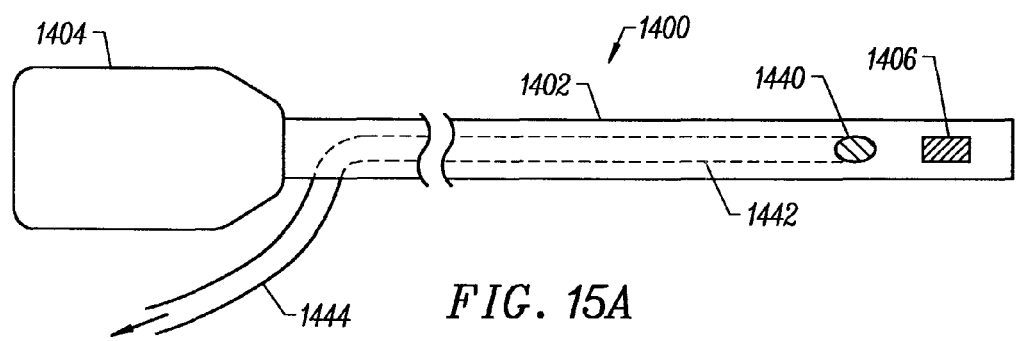
FIG. 15A shows an electrosurgical probe including a resection unit and an aspiration device, according to the invention.
Figure 15B:
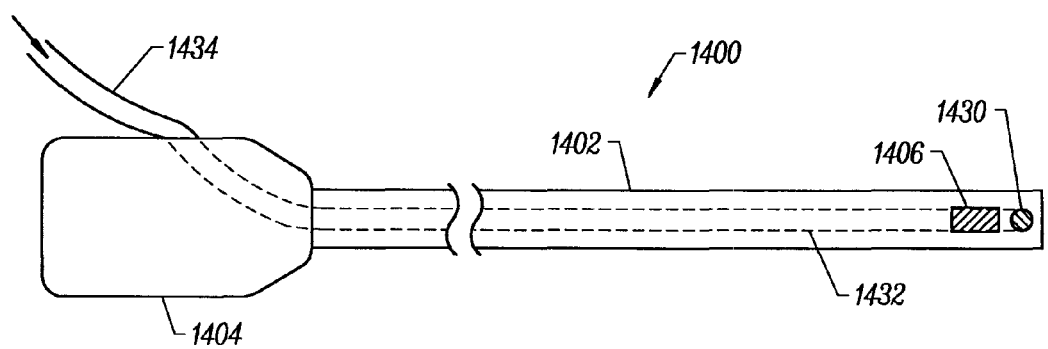
FIG. 15B shows an electrosurgical probe including a resection unit and a fluid delivery device, according to one embodiment of the invention.

With reference to FIG. 14A, probe 1400 includes a fluid delivery tube 1434, and a fluid delivery port 1430 located distal to resection unit 1406 on shaft distal end portion 1402a. Fluid delivery port 1430 is coupled to fluid delivery tube 1434 via a fluid delivery lumen 1432 (FIG. 15B). Fluid delivery tube 1434 is, in turn, coupled to a source of an electrically conductive fluid (see, e.g., FIG. 2). Fluid delivery port 1430 is adapted to provide a quantity of an electrically conductive fluid to shaft distal end portion 1402a during a procedure, as is described elsewhere herein in enabling detail.

Figure 14B:
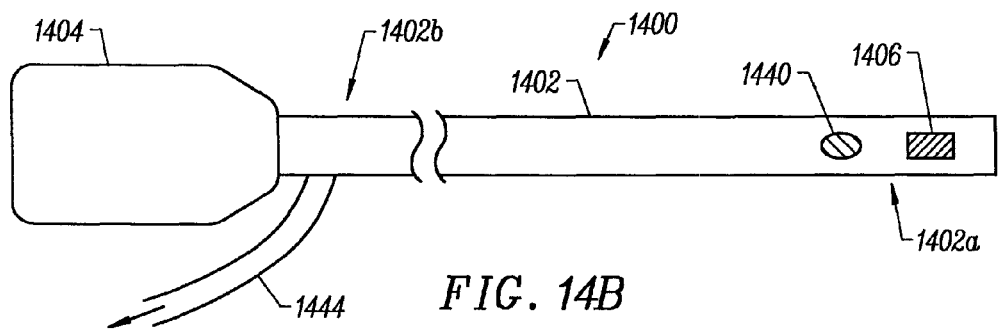
Figure 14C:
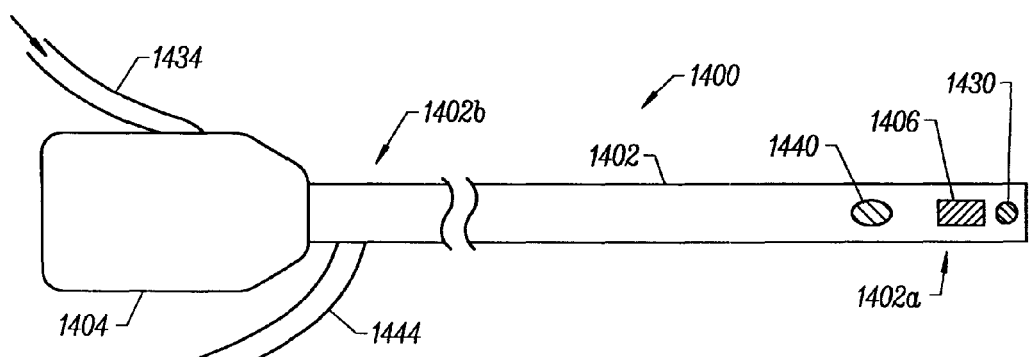

FIG. 14B shows probe 1400 including an aspiration tube 1444 and an aspiration port 1440 located proximal to resection unit 1406. In the embodiment depicted in FIG. 14B, aspiration tube 1444 is shown as being connected to probe 1400 at shaft proximal end 1402b, however other arrangements for coupling aspiration tube 1444 to probe 1400 are possible under the invention. FIG. 14C shows probe 1400 including both an aspiration tube 1444 and a fluid delivery tube 1434; and both a fluid delivery port 1430 and an aspiration port 1440. Although fluid delivery port 1430 is depicted in FIGS. 14A, 14C as a single port located distal to resection unit 1406, other arrangements of fluid delivery port(s) 1430/ 1430' with respect to resection unit 1406, are contemplated according to various embodiments of the invention. Aspiration port 1440 is located proximal to resection unit 1406. Preferably, aspiration port 1440 is located a distance of at least 2 mm proximal to resection unit 1406. More preferably, aspiration port 1440 is located a distance in the range of from about 4 mm to about 50 mm proximal to resection unit 1406. In one embodiment, aspiration port 1440 may have a screen (not shown) to prevent relatively large fragments of resected tissue from entering aspiration lumen 1442 (FIG. 15A). Such a screen may serve as an active electrode and cause ablation of tissue fragments which contact the screen. Alternatively, the screen may serve as a mechanical sieve or filter to exclude entry of relatively large tissue fragments into lumen 1442.

Figure 14D:
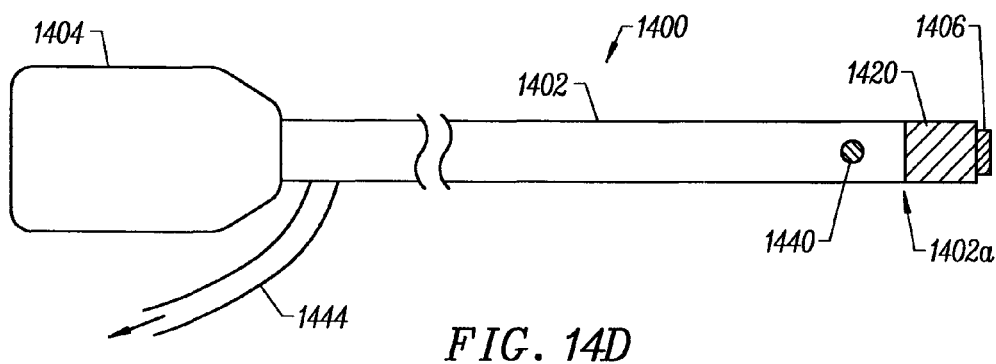

FIG. 14D shows probe 1400 in which resection unit 1406 is located at the distal terminus of shaft 1402. In this embodiment, return electrode 1420 is located at shaft distal end 1402a, and aspiration port 1440 is located proximal to return electrode 1420. The embodiment of FIG. 14D may further include one or more fluid delivery ports 1430 (see, for example, FIG. 15B) for delivering an electrically conductive fluid to, at least, resection unit 1406. In certain embodiments, fluid delivery port(s) 1430 deliver a quantity of an electrically conductive fluid to shaft distal end 1402a sufficient to immerse resection unit 1406 and return electrode 1420. In some embodiments, fluid delivery port(s) 1430 deliver a quantity of an electrically conductive fluid from shaft distal end 1402a sufficient to immerse the tissue at a site targeted for ablation and/or resection.

FIG. 15A shows electrosurgical probe 1400 including resection unit 1406 and aspiration port 1440 proximal to resection unit 1406, according to one embodiment of the invention. Aspiration port 1440 is coupled to aspiration tube 1444 via an aspiration lumen 1442. Aspiration tube 1444 may be coupled to a vacuum source, as is well known in the art. Aspiration lumen 1442 serves as a conduit for removal of unwanted materials (e.g., excess fluids and resected tissue fragments) from the surgical field or target site of an ablation and/or resection procedure, essentially as described hereinabove with reference to other embodiments of an electrosurgical probe. The embodiment of FIG. 15A may further include a fluid delivery device (see, for example, FIG. 15B).

FIG. 15B shows electrosurgical probe 1400 including resection unit 1406 and fluid delivery port 1430 located distal to resection unit 1406, according to one embodiment of the invention. Fluid delivery port 1430 is coupled to fluid delivery tube 1434 via a fluid delivery lumen 1432. Fluid delivery lumen 1432 serves as a conduit for providing a quantity of an electrically conductive fluid to resection unit 1406 and/or the target site of an ablation and resection procedure. The embodiment of FIG. 15B may further include an aspiration device (see, for example, FIG. 15A). In the embodiment of FIG. 15B, tube 1434 is coupled to probe 1400 at handle 1404, however other arrangements for coupling tube 1434 to probe 1400 are also within the scope of the invention.

FIGS. 16A-F each show a resection unit 1406a-f as seen in plan view, wherein each resection unit 1406a-f includes a resection electrode support 1408 and at least one resection electrode head 1412, according to various embodiments of the invention. Each resection electrode 1410 (e.g., FIG. 13), may have a single terminal or resection electrode head 1412, such that each resection electrode head 1412 is independently coupled to a power supply (e.g., power supply 428 of FIG. 2). Alternatively, each resection electrode 1410 may have a plurality of terminals or resection electrode heads 1412. Each resection electrode 1410 may be coupled to a power supply unit (not shown in FIGS. 16A-F) via a connection block and connector cable, essentially as described hereinabove (e.g., with reference to FIGS. 2 & 4).

FIG. 16A indicates the longitudinal axis 1406' of resection units 1406a-f, as well as electrode support distal end 1408a (indication of longitudinal axis 1406' and support distal end 1408a are omitted from FIGS. 16A-F for the sake of clarity, however the orientation of resection units 1406b-f is the same as that of resection unit 1406a). In each of FIGS. 16A-F, resection electrode heads 1412 are depicted as having an elongated, substantially rectangular shape in plan view. However, other shapes and arrangements for resection electrode heads 1412 are also within the scope of the invention.

FIGS. 16A-F show just some of the arrangements of resection electrode head(s) 1412 on each resection electrode support 1408, according to various embodiments. Briefly, FIG. 16A shows a single resection electrode head 1412 located substantially centrally within support 1408 and aligned approximately perpendicular to longitudinal axis 1406'. FIG. 16B shows a plurality of resection electrode heads 1412 arranged substantially parallel to each other and aligned substantially perpendicular to axis 1406'. FIG. 16C shows a plurality of resection electrode heads 1412 arranged substantially parallel to each other and aligned substantially perpendicular to axis 1406', and an additional resection electrode head 1412 arranged substantially parallel to axis 1406'. FIG. 16D shows a plurality of resection electrode heads 1412 arranged substantially parallel to each other and aligned at an angle intermediate between parallel to axis 1406' and perpendicular to axis 1406'. FIG. 16E shows a plurality of resection electrode heads 1412 including a first substantially parallel array 1412a aligned at a first angle with respect to axis 1406' and a second substantially parallel array 1412b aligned at a second angle with respect to axis 1406'. FIG. 16F shows a plurality of resection electrode heads 1412 having an arrangement similar to that described for FIG. 16E, wherein resection electrode heads 1412 are of different sizes.

Figure 17:
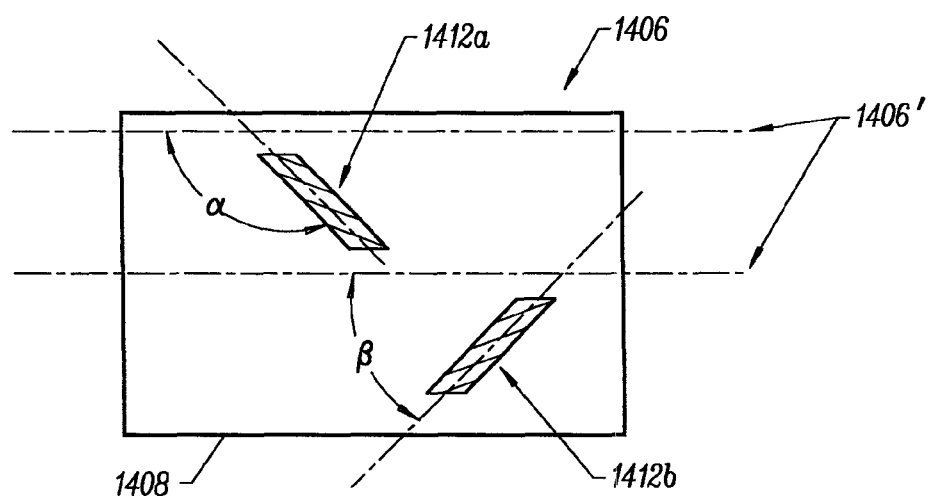
FIG. 17 illustrates an arrangement of a resection electrode head with respect to the longitudinal axis of a resection unit.

FIG. 17 illustrates an angle at which a resection electrode head 1412 may be arranged on electrode support 1408 with respect to the longitudinal axis 1406' of resection unit 1406. According to certain embodiments, resection electrode heads 1412 may be arranged on electrode support 1408 at an angle in the range of from 0° to about 175° with respect to longitudinal axis 1406'. In embodiments having first and second parallel arrays of resection electrode heads 1412, e.g., FIG. 16E, first array 1412a is preferably arranged at an angle α in the range of from about 90° to 170°, and more preferably from about 105° to 165°. Second array 1412b is preferably arranged at an angle β in the range of from about 10° to 90°, and more preferably from about 15° to 75°.

Figure 18A:
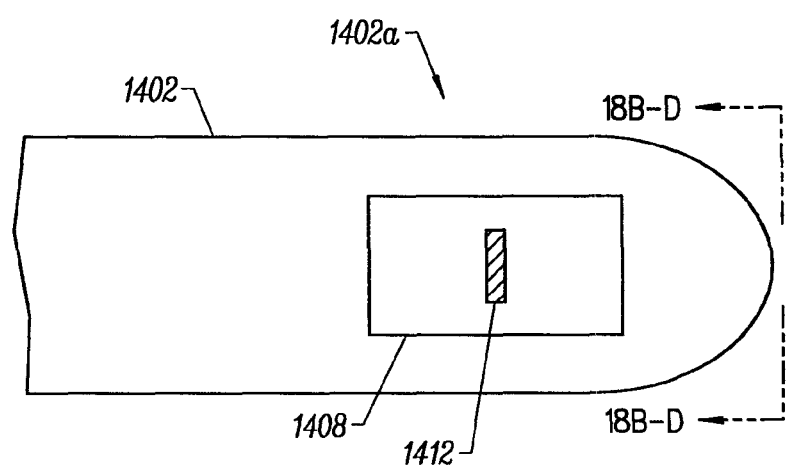
FIG. 18A shows, in plan view, a resection electrode support disposed on a shaft distal end of an electrosurgical probe.
Figure 18B:
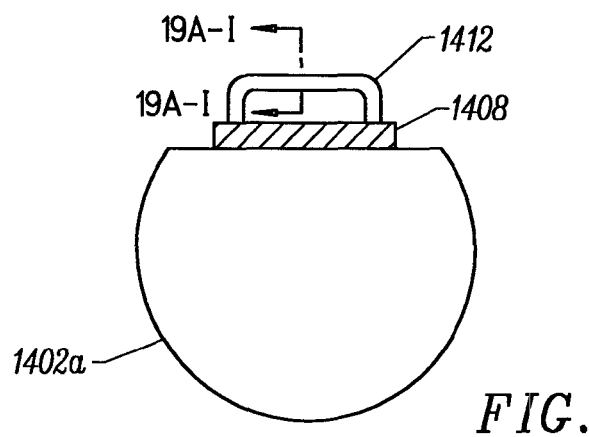
FIGS. 18B-D each show a profile of a resection electrode head on a resection electrode support.
Figure 18C:
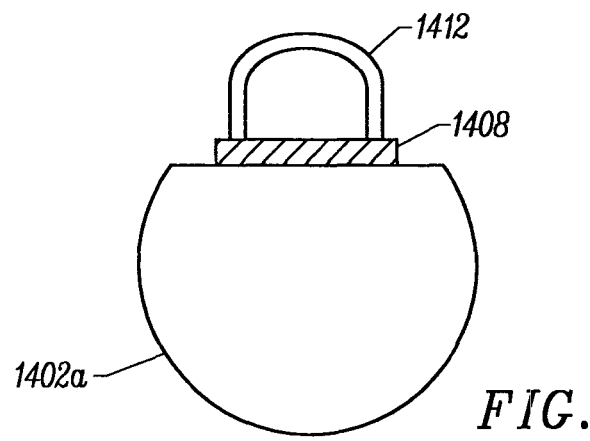
Figure 18D:
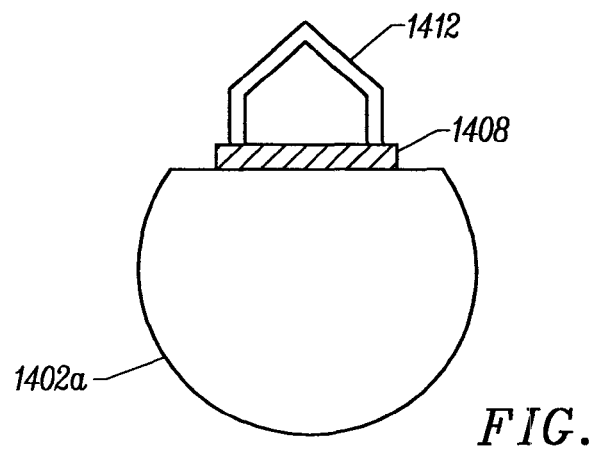

FIG. 18A shows in plan view a resection electrode support 1408 arranged on shaft distal end portion 1402a, wherein electrode support 1408 includes resection electrode head 1412. FIGS. 18B-D each show a profile of a resection electrode head 1412 on an electrode support 1408 as seen along the line 18B-D of FIG. 18A. From an examination of FIGS. 18B-D it can be readily seen that, according to certain embodiments of the invention, resection electrode head 1412 may protrude a significant distance from the external surface of shaft 1402. Typically, each resection electrode head 1412 protrudes from resection electrode support 1408 by a distance in the range of from about 0.1 to 20 mm, and preferably by a distance in the range of from about 0.2 to 10 mm. Resection electrode head 1412 may have a profile which is substantially square or rectangular; arched or semi-circular; or angular and pointed, as represented by FIGS. 18B-D, respectively. Other profiles and shapes for resection electrode head 1412 are also within the scope of the invention. Only one resection electrode head 1412 is depicted per electrode support 1408 in FIGS. 18A-D. However, according to the invention, each electrode support 1408 may have a plurality of resection electrode heads 1412 arranged thereon in a variety of arrangements (see, e.g., FIGS. 16A-F).

In the embodiments of FIGS. 18B-D, each electrode head 1412 is in the form of a filament or wire of electrically conductive material. In one embodiment, the filament or wire comprises a metal. Such a metal is preferably a durable, corrosion resistant metal. Suitable metals for construction of resection electrode head 1412 include, without limitation, tungsten, stainless steel alloys, platinum or its alloys, titanium or its alloys, molybdenum or its alloys, and nickel or its alloys. In embodiments wherein each electrode head 1412 is in the form of a filament or wire, the diameter of the wire is preferably in the range of from about 0.05 mm to about 5 mm, more preferably in the range of from about 0.1 to about 2 mm.

FIGS. 19A-I each show a cross-section of the filament or wire of resection electrode head 1412 as seen, for example, along the lines 19A-I of FIG. 18B. Evidently, a variety of different cross-sectional shapes for resection electrode head 1412 are possible. For example, resection electrode head 1412 may be substantially round or circular, substantially square, or substantially triangular in cross-section, as depicted in FIGS. 19A-C, respectively. Resection electrode head 1412 may have a cross-section having at least one curved side. For example, head 1412d of FIG. 19D has two substantially parallel sides and two concave sides. Head 1412e of FIG. 19E has four concave sides forming four cusps, while head 1412f (FIG. 19F) includes three concave sides forming three cusps. FIGS. 19G-I each depict a cross-section of a wire or filament having serrations on at least one side thereof. Resection electrode head 1412g comprises a filament having a substantially circular cross-section, wherein the circumference of the filament is serrated. In another embodiment (not shown) a selected portion of the circumference of a substantially round filament may be serrated. Resection electrode head 1412h (FIG. 19H) comprises a filament having a substantially square cross-section, Wherein a leading or cutting edge portion 1413h of the filament is serrated. FIG. 19I shows a head 1412i comprising a filament of an electrically conductive material having a substantially crescent-shaped or semi-circular cross-sectional shape, wherein cutting edge portion 1413i is serrated. In addition, other cross-sectional shapes for electrode head 1412 are contemplated and are within the scope of the invention. Preferably, the cross-sectional shape and other features of resection electrode head 1412 promote high current densities in the vicinity of resection electrode head 1412 following application of a high frequency voltage to resection electrode head 1412. More preferably, the cross-sectional shape and other features of resection electrode head 1412 promote high current densities in the vicinity of a leading or cutting edge, e.g., edge 1413h, 1413i, of resection electrode head 1412 following application of a high frequency voltage to resection electrode head 1412. As noted previously, high current densities promote generation of a plasma in the presence of an electrically conductive fluid, and the plasma in turn efficiently ablates tissue via the Coblation® procedure or mechanism. Preferably, the cross-sectional shape and other features of resection electrode head 1412 are also adapted for maintenance of the plasma in the presence of a stream of fluid passing over resection electrode head 1412. In one embodiment, the cross-sectional shape and other features of resection electrode head 1412 are also adapted for the efficient mechanical resection, abrading, or severing of, at least, soft tissue (such as skeletal muscle, skin, cartilage, etc.).

In one embodiment a cutting edge, e.g., edge 1413h, 1413i, is adapted for both ablating and resecting tissue. Depending on the embodiment, cutting edge 1413h, 1413i may be oriented, or point, in various directions relative to the longitudinal axis of shaft 1402. For example, depending on the particular embodiment of probe 1400, and on the particular surgical procedure(s) for which embodiments of probe 1400 are designed to perform, cutting edge 1413h, 1413i may be oriented distally, proximally, or laterally.

Figure 20:
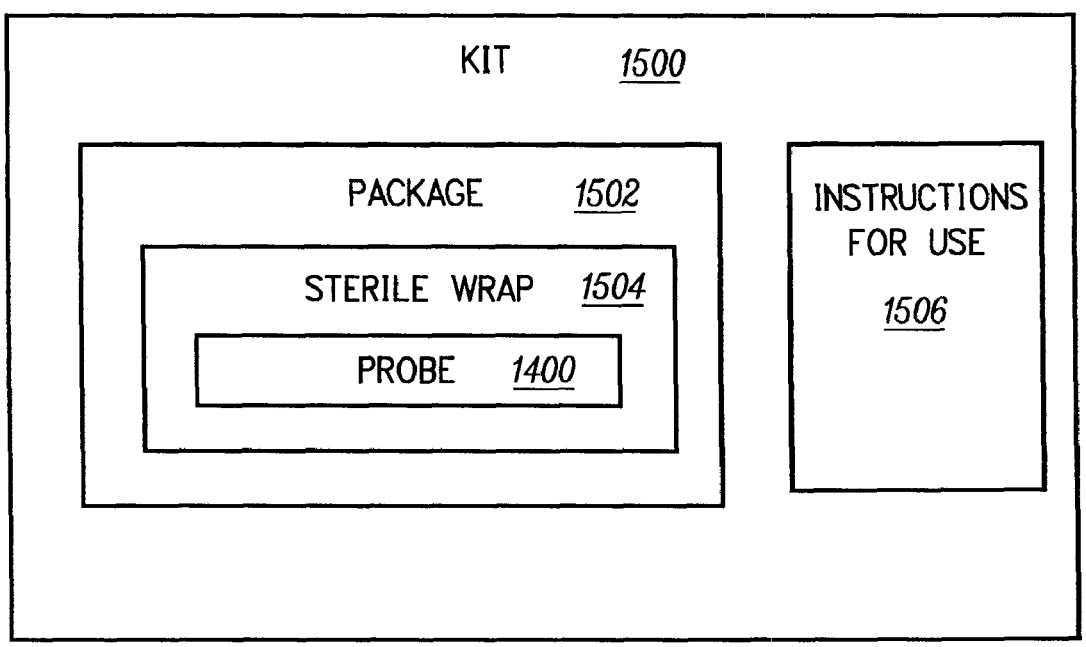
FIG. 20 schematically represents a surgical kit for resection and ablation of tissue, according to another embodiment of the invention.

Referring now to FIG. 20, a surgical kit 1500 for resecting and/or ablating tissue according to the invention will now be described. FIG. 20 schematically represents surgical kit 1500 including electrosurgical probe 1400, a package 1502 for housing probe 1400, a surgical instrument 1504, and an instructions for use 1506. Instructions for use 1506 include instructions for using probe 1400 in conjunction with apparatus ancillary to probe 1400, such as power supply 428 (FIG. 2). Package 1502 may comprise any suitable package, such as a box, carton, etc. In an exemplary embodiment, package 1502 includes a sterile wrap or wrapping 1504 for maintaining probe 1400 under aseptic conditions prior to performing a surgical procedure.

An electrosurgical probe 1400 of kit 1500 may comprise any of the embodiments described hereinabove. For example, probe 1400 of kit 1500 may include shaft 1402 having at least one resection electrode 1410 at shaft distal end 1402a, and at least one connector (not shown) extending from the at least one resection electrode 1410 to shaft proximal end 1402*b* for coupling resection electrode 1410 to a power supply. Probe 1400 and kit 1500 are disposable after a single procedure. Probe 1400 may or may not include a return electrode 1420.

Instructions for use 1506 generally includes, without limitation, instructions for performing the steps of: adjusting a voltage level of a high frequency power supply to effect resection and/or ablation of tissue at the target site; connecting probe 1400 to the high frequency power supply; positioning shaft distal end 1402*a* within an electrically conductive fluid at or near the tissue at the target site; and activating the power supply to effect resection and/or ablation of the tissue at the target site. An appropriate voltage level of the power supply is usually in the range of from about 40 to 400 volts RMS for operating frequencies of about 100 to 200 kHz. Instructions 1506 may further include instruction for advancing shaft 1402 towards the tissue at the target site, and for moving shaft distal end portion 1402*a* in relation to the tissue. Such movement may be performed with or without the exertion of a certain mechanical force on the target tissue via resection unit 1406, depending on parameters such as the nature of the procedure to be performed, the type of tissue at the target site, the rate at which the tissue is to be removed, and the particular design or embodiment of probe 1400/resection unit 1406.

Figure 21A:
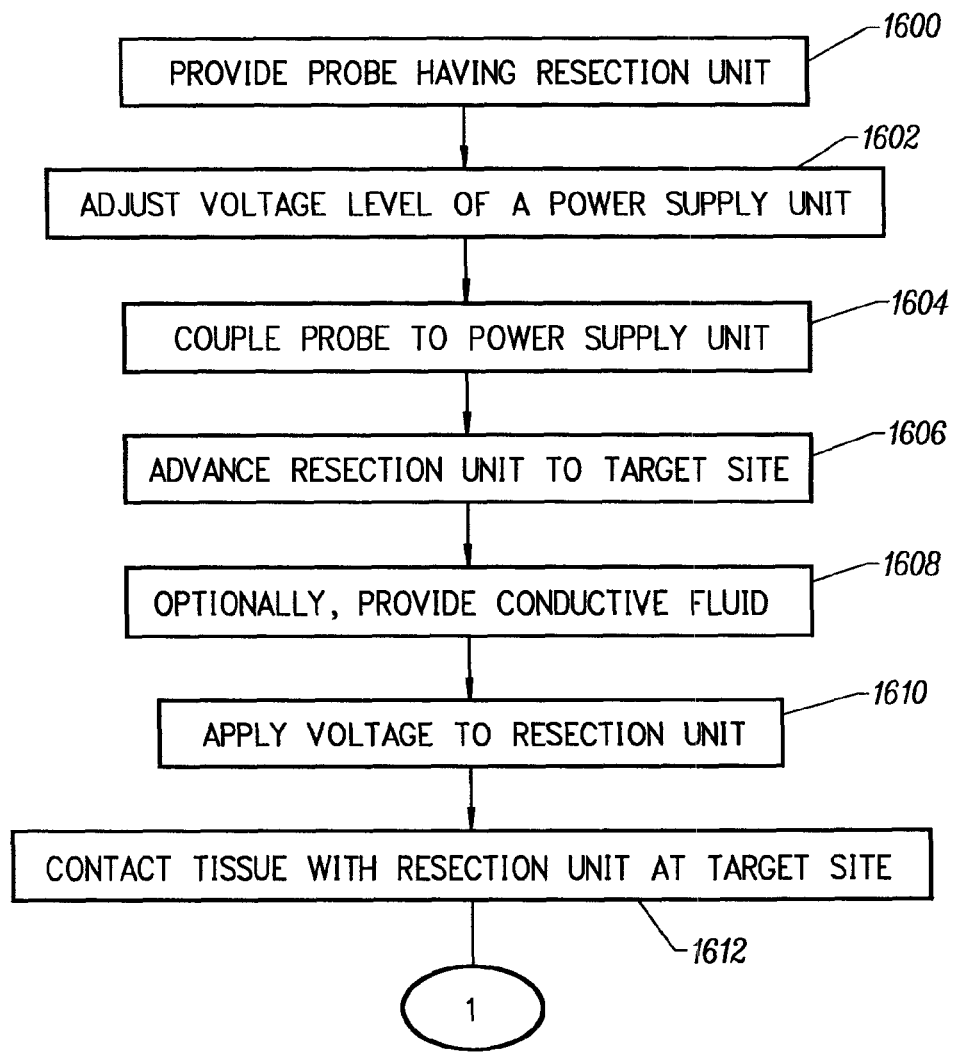
FIGS. 21A-B schematically represent a method of performing a resection and ablation electrosurgical procedure, according to another embodiment of the invention.
Figure 21B:
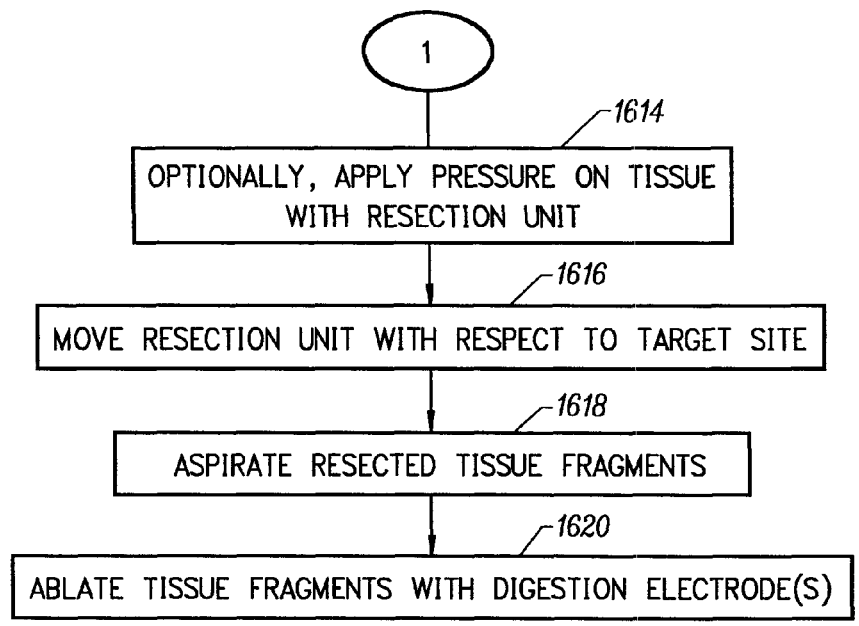

FIGS. 21A-B schematically represent a method of performing a resection and ablation electrosurgical procedure, according to another embodiment of the invention, wherein step 1600 (FIG. 421A) involves providing an electrosurgical probe having a resection unit. The probe provided in step 1600 includes a shaft distal end, wherein the resection unit is disposed at the shaft distal end, either laterally or terminally. The resection unit includes an electrode support comprising an insulating material and at least one resection electrode head arranged on the electrode support. Step 1602 involves adjusting a voltage level of a power supply, wherein the power supply is capable of providing a high frequency voltage of a selected voltage level and frequency. The voltage selected is typically between about 5 kHz and 20 MHz, essentially as described hereinabove. The RMS voltage will usually be in the range of from about 5 volts to 1000 volts, and the peak-to-peak voltage will be in the range of from about 10 to 2000 volts, again as described hereinabove. The actual or preferred voltage will depend on a number of factors, including the number and size of resection electrodes comprising the resection unit.

Step 1604 involves coupling the probe to the power supply unit. Step 1606 involves advancing the resection unit towards tissue at a target site whence tissue is to be removed. In optional step 1608, a quantity of an electrically conductive fluid may be applied to the resection unit and/or to the target site. For performance of a resection and ablation procedure in a dry field, optional step 1608 is typically included in the procedure. Step 1608 may involve the application of a quantity of an electrically conductive fluid, such as isotonic saline, to the target site. The quantity of an electrically conductive fluid may be controlled by the operator of the probe. The quantity of an electrically conductive fluid applied in step 1608 may be sufficient to completely immerse the resection unit and/or to completely immerse the tissue at the target site. Step 1610 involves applying a high frequency voltage to the resection unit via the power supply unit. Step 1612 involves contacting the tissue at the target site with the resection unit.

With reference to FIG. 21B, optional step 1614 involves exerting pressure on the tissue at the target site by applying a force to the probe, while the resection unit is in contact with the tissue at the target site, in order to effect resection of tissue. Typically, such a force is applied manually by the operator (surgeon), although mechanical application of a force to the probe, e.g., by a robotic arm under computer control, is also possible. The amount of any force applied in optional step 1614 will depend on factors such as the nature of the tissue to be removed, the design or embodiment of the probe, and the amount of tissue to be resected. For example, in the absence of any mechanical force applied to the tissue, tissue removal from the target site is primarily or solely by ablation. On the other hand, with the electrical power turned off, either transiently or for all or a portion of a procedure, the probe may be used for mechanical resection of tissue. Typically, however, the probe is used for the concurrent electrical ablation and mechanical resection of tissue.

Step 1616 involves moving the resection unit of the probe with respect to the tissue at the target site. Typically, step 1616 involves moving the resection unit and the at least one resection electrode head in a direction substantially perpendicular to a direction of any pressure exerted in step 1614, or in a direction substantially parallel to a surface of the tissue at the target site. Typically, step 1616 is performed concurrently with one or more of steps 1608 through 1614. In one embodiment, step 1616 involves repeatedly moving the resection unit with respect to the tissue at the target site until an appropriate quantity of tissue has been removed from the target site. Typically, a portion of the tissue removed from the target site is in the form of resected tissue fragments. Step 1618 involves aspirating the resected tissue fragments from the target site via at least one aspiration port on the shaft, wherein the at least one aspiration port is coupled to an aspiration lumen. In one embodiment, the probe includes at least one digestion electrode capable of aggressively ablating resected tissue fragments. Step 1620 involves ablating resected tissue fragments with the at least one digestion electrode. In one embodiment, the at least one digestion electrode is arranged within the aspiration lumen, and the resected tissue fragments are ablated within the aspiration lumen.

Figure 22:
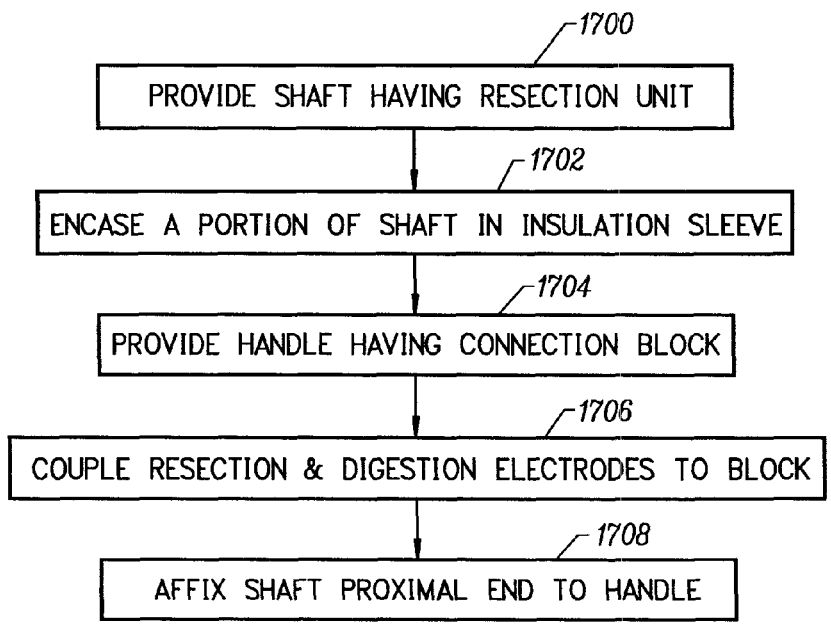
FIG. 22 schematically represents a method of making a resection and ablation electrosurgical probe, according to yet another embodiment of the invention.

FIG. 22 schematically represents a method of making a resection and ablation electrosurgical probe, according to the invention, wherein step 1700 involves providing a shaft having a resection unit. The shaft provided in step 1700 includes a shaft proximal end and a shaft distal end, wherein the resection unit is disposed at the shaft distal end, either laterally or terminally. In one embodiment, the shaft comprises an electrically conductive lightweight metal cylinder. The resection unit includes an electrode support comprising an insulating material and at least one resection electrode arranged on the electrode support. Each resection electrode includes a resection electrode head. Each resection electrode head typically comprises a wire, filament, or blade of a hard or rigid, electrically conductive solid material, such as tungsten, stainless steel alloys, platinum or its alloys, titanium or its alloys, molybdenum or its alloys, nickel or its alloys, and the like.

Typically, the shaft provided in step 1700 further includes at least one digestion electrode capable of aggressively ablating tissue fragments. In one embodiment, the at least one digestion electrode is arranged within the aspiration lumen. Each digestion electrode typically comprises an electrically conductive metal, such as tungsten, stainless steel alloys, platinum or its alloys, titanium or its alloys, molybdenum or its alloys, nickel or its alloys, aluminum, gold, or copper, and the like. Typically, the shaft provided in step 1700 further includes a return electrode.

In one embodiment, the method includes step 1702 which involves encasing a portion of the shaft within an insulating sleeve to provide an electrically insulated proximal portion of the shaft and an exposed distal portion of the shaft. The exposed distal portion of the shaft defines a return electrode of the probe. The insulating sleeve typically comprises a substantially cylindrical length of a flexible insulating material such as polytetrafluoroethylene, a polyimide, and the like. Such flexible insulating materials are well known in the art. In one embodiment, the resection electrode support is disposed on the return electrode. The resection electrode support typically comprises an electrically insulating material such as a glass, a ceramic, a silicone, a polyurethane, a urethane, a polyimide, silicon nitride, teflon, alumina, or the like. The electrode support serves to electrically insulate the at least one resection electrode head from the return electrode. Step 1704 involves providing a handle having a connection block. Step 1706 involves coupling the resection electrodes and the digestion electrodes to the connection block. The connection block provides a convenient mechanism by which the resection and digestion electrodes may be coupled to a high frequency power supply. Step 1708 involves affixing the shaft proximal end to the handle.

FIGS. 23A and 23B show a side view and an end-view, respectively, of an electrosurgical suction apparatus 2100, according to another embodiment of the invention. Apparatus 2100 generally includes a shaft 2102 having a shaft distal end portion 2102a and a shaft proximal end portion 2102b, the latter affixed to a handle 2104. An aspiration tube 2144, adapted for coupling apparatus 2100 to a vacuum source, is joined at handle 2104. An electrically insulating electrode support 2108 is disposed on shaft distal end portion 2102a. Electrode support 2108 may comprise a durable or refractory material such as a ceramic, a glass, a fluoropolymer, or a silicone rubber. In one embodiment, electrode support 2108 comprises an alumina ceramic. A plurality of active electrodes 2110 are arranged on electrode support 2108.

Shaft 2102 may comprise an electrically conducting material, such as stainless steel alloys, tungsten, platinum or its alloys, titanium or its alloys, molybdenum or its alloys, and nickel or its alloys. An insulating sleeve 2118 covers a portion of shaft 2102. An exposed portion of shaft 2102 located between sleeve distal end 2118a and electrode support 2108 defines a return electrode 2116. In an alternative embodiment (not shown), shaft 2102 may comprise an insulating material and a return electrode may be provided on the shaft, for example, in the form of an annulus of an electrically conductive material.

Figure 23C:
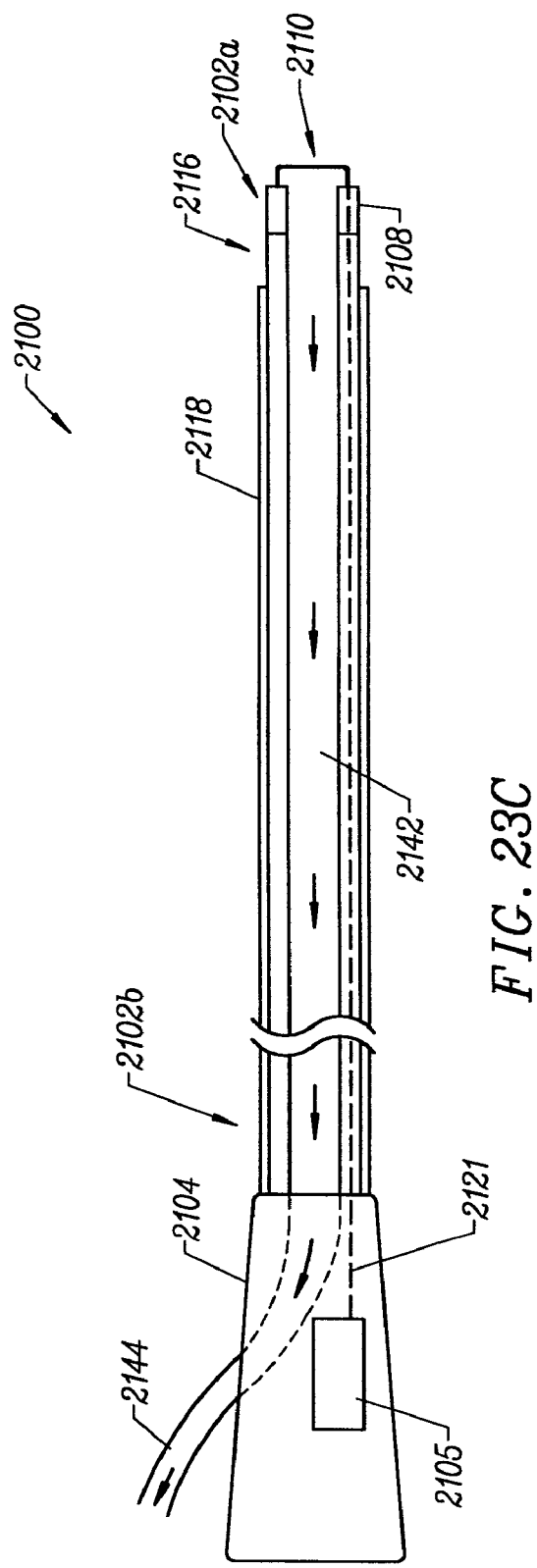
FIG. 23C shows a longitudinal cross-section of the apparatus of FIGS. 23A, 23B.

FIG. 23B shows an end-view of apparatus 2100, taken along the lines 23B-23B of FIG. 23A. A plurality of active electrodes 2110 are arranged substantially parallel to each other on electrode support 2108. A void within electrode support 2108 defines an aspiration port 2140. Typically, the plurality of active electrodes 2110 span or traverse aspiration port 2140, wherein the latter is substantially centrally located within electrode support 2108. Aspiration port 2140 is in communication with an aspiration channel 2142 (FIG. 23C) for aspirating unwanted materials from a surgical site.

FIG. 23C shows a longitudinal cross-section of the apparatus of FIG. 23A. Aspiration channel 2142 is in communication at its proximal end with aspiration tube 2144. Aspiration port 2140, aspiration channel 2142, and aspiration tube 2144 provide a convenient aspiration unit or element for removing unwanted materials, e.g., ablation by-products, excess saline, from the surgical field during a procedure. The direction of flow of an aspiration stream during use of apparatus 2100 is indicated by the solid arrows. Handle 2104 houses a connection block 2105 adapted for independently coupling active electrodes 2110 and return electrode 2116 to a high frequency power supply (e.g., FIG. 1). An active electrode lead 2121 couples each active electrode 2110 to connection block 2105. Return electrode 2116 is independently coupled to connection block 2105 via a return electrode connector (not shown). Connection block 2105 thus provides a convenient mechanism for independently coupling active electrodes 2110 and return electrode 2116 to a power supply (e.g., power supply 28, FIG. 1).

Figure 24A:
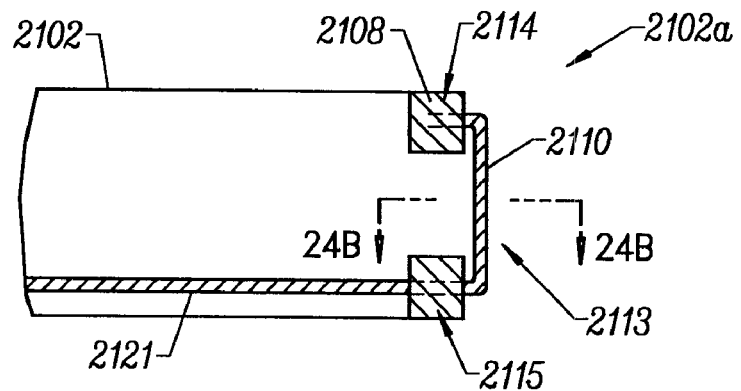
FIG. 24A shows a longitudinal cross-section of the shaft distal end of an electrosurgical suction apparatus, according to the invention.
Figure 24B:
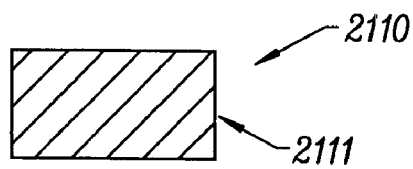
FIG. 24B shows a transverse cross-sectional view of an active electrode of the apparatus of FIG. 24A as taken along the lines 24B-24B.

FIG. 24A is a longitudinal cross-section of the shaft distal end 2102a of an electrosurgical suction apparatus 2100, showing the arrangement of active electrode 2110 according to one embodiment. Active electrode 2110 includes a loop portion 2113, a free end 2114, and a connected end 2115. Active electrode 2110 is disposed on electrode support 2108, and is in communication at connected end 2115 with active electrode lead 2121 for coupling active electrode 2110 to connection block 2105. Aspiration channel 2142 is omitted from FIG. 24A for the sake of clarity. FIG. 24B is a cross-section of active electrode 2110 as taken along the lines 24B-24B of FIG. 24A, showing an electrode distal face 2111. Although FIG. 24B shows a substantially rectangular shape for active electrode 2110, other shapes (e.g., those depicted in FIGS. 19A-I) are also possible under the invention.

Figure 24C:
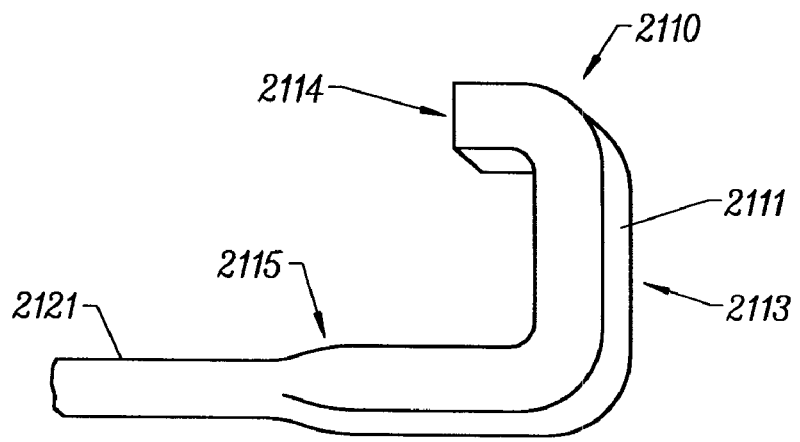
FIG. 24C shows an active electrode in communication with an electrode lead.

FIG. 24C shows in more detail active electrode 2110 in the form of a loop of flattened wire in communication with electrode lead 2121, according to one embodiment of the invention. Typically, free end 2114 terminates within electrode support 2108 or within another electrically insulating material. In this embodiment, electrode lead 2121 is integral with active electrode 2110. Electrode lead 2121 and active electrode 2110 may each comprise a highly conductive, corrosion-resistant metal such as tungsten, stainless steel alloys, platinum or its alloys, titanium or its alloys, molybdenum or its alloys, nickel or its alloys, iridium, aluminum, gold, copper, and the like. In one embodiment, one or both of electrode lead 2121 and active electrode 2110 may each comprise a platinum/iridium alloy, such as an alloy comprising from about 85% to 95% platinum and from about 5% to 15% iridium.

FIG. 25A shows an electrosurgical suction apparatus 2100 having an outer sheath 2152 external to shaft 2102 to provide an annular fluid delivery channel 2150, according to another aspect of the invention. The distal terminus of outer sheath 2152 defines an annular fluid delivery port 2156 at a location proximal to return electrode 2116. Outer sheath 2152 is in communication at its proximal end with a fluid delivery tube 2154 at handle 2104. Fluid delivery port 2156, fluid delivery channel 2150, and tube 2154 provide a convenient fluid delivery unit for providing an electrically conductive fluid (e.g., isotonic saline) to the distal end of the suction apparatus or to a target site undergoing treatment. The direction of flow of an electrically conductive fluid during use of apparatus 2100 is indicated by the solid arrows. An extraneous electrically conductive fluid forms a current flow path between active electrodes 2110 and return electrode 2116, and can facilitate generation of a plasma in the vicinity of active electrodes 2110, as described hereinabove. Provision of an extraneous electrically conductive fluid may be particularly valuable in a dry field situation (e.g., in situations where there is a paucity of native electrically conductive bodily fluids, such as blood, synovial fluid, etc.). In an alternative embodiment, an electrically conductive fluid, such as saline, may be delivered to the distal end of suction apparatus 2100 by a separate device (not shown). FIG. 25B is a transverse cross-section of shaft 2102 of the apparatus of FIG. 25A, and shows the relationship between outer sheath 2152, shaft 2102, and fluid delivery port 2156. Aspiration channel 2142 and electrode lead 2121 are omitted from FIGS. 25A, 25B for the sake of clarity.

Figure 26A:
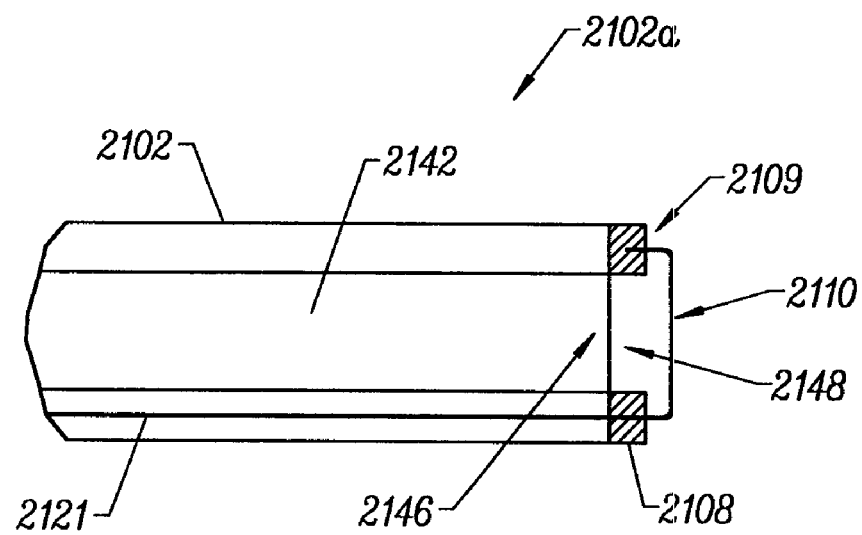
FIG. 26A shows a longitudinal cross-section of the shaft distal end of an electrosurgical suction apparatus having a baffle.
Figure 26B:
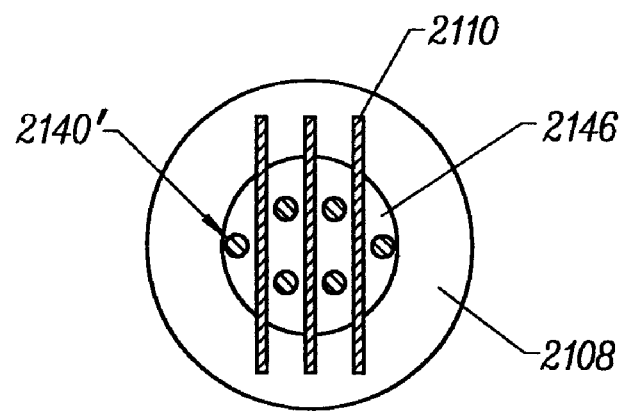
FIG. 26B is an end view of the apparatus of FIG. 26A, according to another embodiment of the invention.

With reference to FIG. 26A there is shown in longitudinal cross-section the shaft distal end 2102a of an electrosurgical suction apparatus 2100 including a baffle or trap 2146, according to another embodiment, wherein baffle 2146 is arranged transversely within shaft 2102 at the distal end of aspiration channel 2142. In the embodiment shown, baffle 2146 is recessed with respect to treatment surface 2109 to define a holding chamber 2148 within the void of electrode support 2108. As seen in the end view of FIG. 26B, baffle 2146 includes a plurality of aspiration ports 2140'. The size, number, and arrangement of ports 2140' on baffle 2146 is at least to some extent a matter of design choice. A plurality of active electrodes 2110 are arranged substantially parallel to each other on electrode support 2108. During a procedure involving resection or ablation of tissue, any relatively large resected tissue fragments or other tissue debris drawn by suction to a location proximal to active electrodes 2110 may be retained by baffle 2146 within holding chamber 2148. By relatively large resected tissue fragments is meant those fragments too large to be readily drawn through ports 2140' in an aspiration stream. Such tissue fragments temporarily retained by baffle 2146 are conveniently positioned with respect to active electrodes 2110, and are readily digested by one or more of active electrodes 2110 by a suitable high frequency voltage applied between active electrodes 2110 and return electrode 2116. As an additional advantage, because aspiration channel 2142 is wider than each of aspiration ports 2140', the former is not subject to being clogged by resected tissue fragments or other debris. Using the configuration of FIGS. 26A, 26B only aspirations ports 2140' are subject to (temporary) blockage; as pointed out above, any tissue fragments too large to pass through ports 2140' are rapidly digested by active electrodes 2110. Baffle 2146 may be constructed from an electrically insulating material, such as various plastics. Alternatively, baffle 2146 may comprise an electrically conducting material such as various metals, in which case baffle 2146 is typically electrically isolated.

Figure 27A:
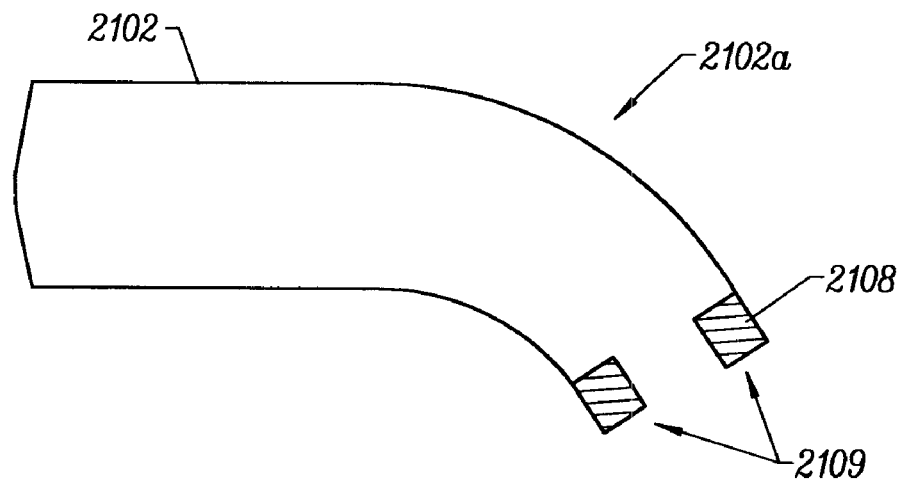
FIGS. 27A and 27B each show a longitudinal cross-section of the shaft distal end of an electrosurgical suction apparatus, according to two different embodiments of the invention.

FIG. 27A is a longitudinal cross-section of a shaft distal end 2102a of a suction apparatus 2100, according to another embodiment, wherein shaft distal end 2102a is curved. The distal end of electrode support 2108 defines a treatment surface 2109 (the latter perhaps best seen in FIG. 28A). A curve in shaft distal end 2102a may facilitate access of treatment surface 2109 to a site targeted for electrosurgical treatment. Active electrodes 2110, which typically protrude from treatment surface 2109 (e.g., FIGS. 28A, 28B), are omitted from FIG. 27A for the sake of clarity.

Figure 27B:
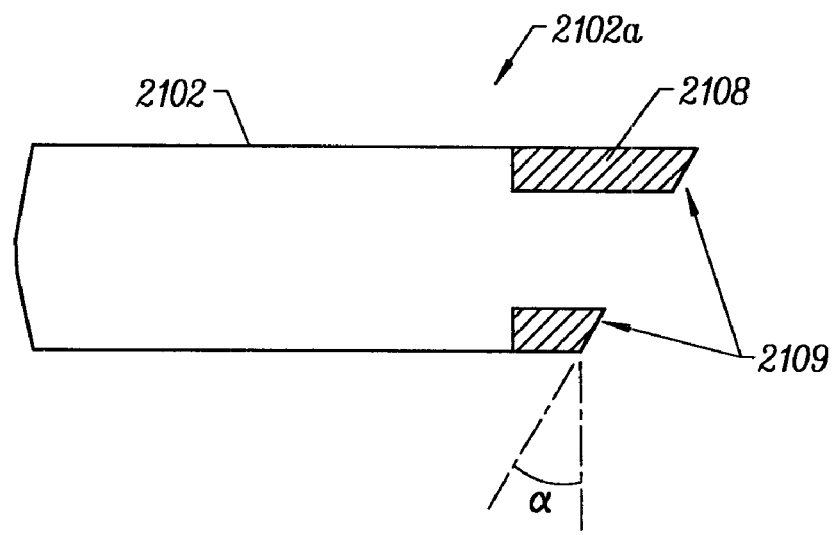

FIG. 27B is a longitudinal cross-section of shaft distal end 2102a of a suction apparatus 2100, according to another embodiment of the invention, wherein the distal end of electrode support 2108 is beveled at an angle, $\propto$. Typically angle $\propto$ is in the range of from about 15° to 60°, more typically from about 20° to 45°, and usually from about 25° to 35°. Active electrodes 2110 are omitted from FIG. 27B for the sake of clarity. A beveled treatment surface 2109 may facilitate access of shaft distal end portion 2102a to tissue at a target site as well as manipulation of shaft 2102 during treatment.

Figure 28A:
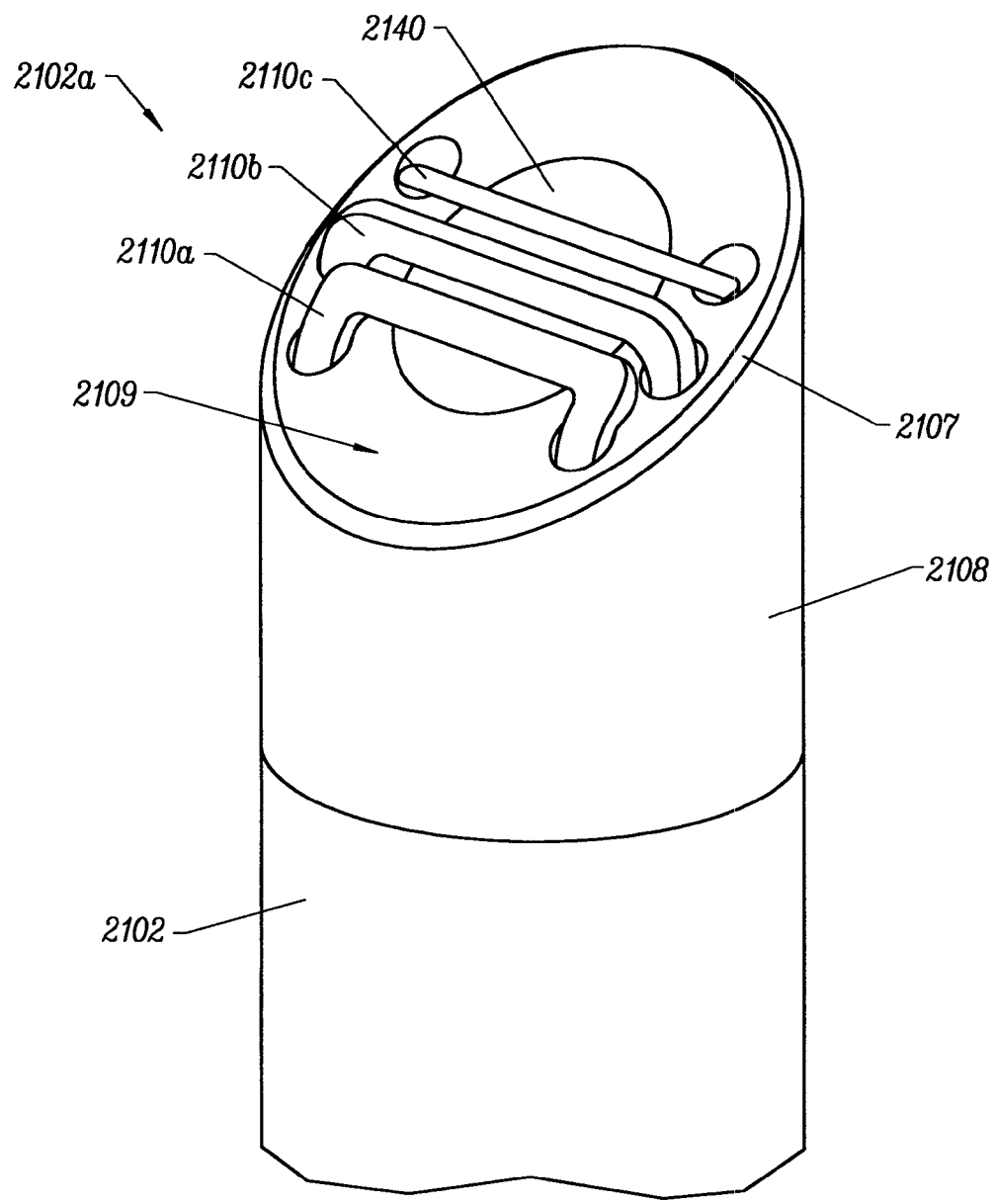
FIGS. 28A and 28B show a perspective view and a side view, respectively, of the shaft distal end of an electrosurgical suction apparatus, according to another embodiment of the invention.

FIG. 28A shows a specific configuration of a shaft distal end 2102a of an electrosurgical suction apparatus 2100, according to one embodiment of the invention. The distal end of electrode support 2108 defines a beveled treatment surface 2109. A first, a second, and a third active electrode 2110a,b,c extend from treatment surface 2109. Treatment surface 2109 includes a rounded perimeter 2107 which serves to eliminate sharp edges from electrode support 2108. The presence of rounded perimeter 2107 prevents mechanical damage to delicate or sensitive tissues during use of apparatus 2100. Electrode support 2108 encircles aspiration port 2140.

Loop portions 2113 (e.g., FIG. 24C) of first, second, and third active electrodes, 2110a, 2110b, 2110c, traverse or bridge aspiration port 2140. First, second, and third active electrodes, 2110a, 2110b; 2110c are arranged substantially parallel to each other, and protrude from treatment surface 2109. In the case of second active electrode 2110b, the orientation with respect to treatment surface 2109 of free end 2114, loop portion 2113, and connected end 2115 is at least substantially the same. In contrast, in the case of first and third active electrodes 2110a, 2110c, the orientation with respect to treatment surface 2109 of loop portion 2113 is different from the orientation of connected end 2115 and free end 2114. That is to say, the orientation of active electrodes 2110a and 2110c with respect to treatment surface 2109 changes from a first direction in the region of connected end 2115 and free end 2114, to a second direction in the region of loop portion 2113.

Furthermore, loop portions 2113 of first, second, and third active electrodes, 2110a, 2110b, 2110c are oriented in different directions. Thus, second electrode 2110b extends substantially in the direction of the longitudinal axis of shaft 2102, and distal face 2111b is also oriented in the direction of the longitudinal axis of shaft 2102. First and third electrodes 2110a, 2110c flank second electrode 2110b, loop portions 2113 of first and second electrodes 2110a, 2110c are oriented towards second electrode 2110b, and distal faces 2111a, 2111c both face towards second electrode 2110b. In other words, first, second, and third electrodes 2110a, 2110b, 2110c all point in different directions.

Figure 28B:
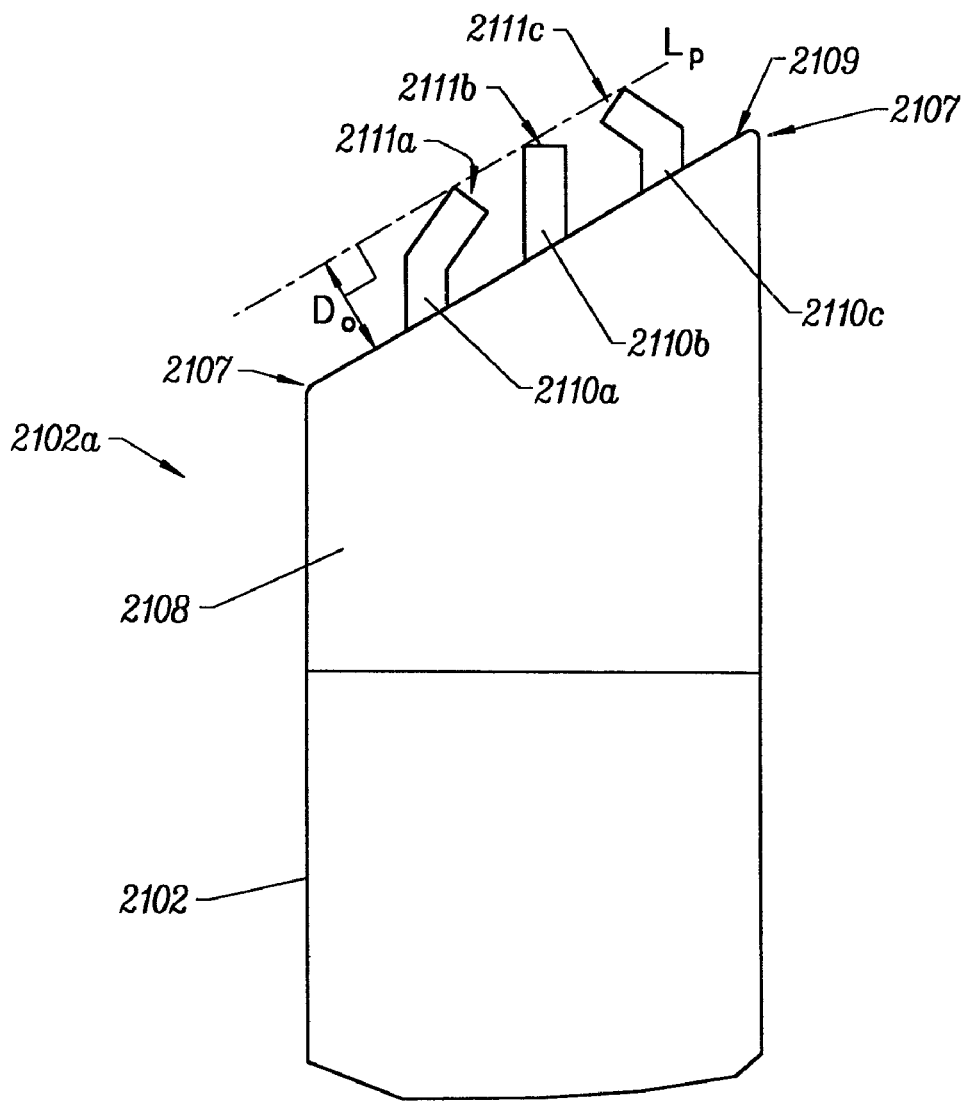

Perhaps as best seen in FIG. 28B, each active electrode 2110a-c includes a distal face 2111a-c. In the embodiment of FIGS. 28A, 28B, each distal face 2111a, 2111b, 2111c faces, or is oriented in, a different direction as described with reference to FIG. 28A. Furthermore, a dashed line Lp drawn parallel to treatment surface 2109 illustrates that the orthogonal distance, Do from treatment surface 2109 to each distal face 2111a,b,c is substantially the same for each of active electrodes 2110a,b,c.

Electrosurgical suction apparatus 2100 described with reference to FIGS. 23A through 23B can be used for the removal, resection, ablation, and contouring of tissue during a broad range of procedures, including procedures described hereinabove with reference to other apparatus and systems of the invention. Typically during such procedures, the apparatus is advanced towards the target tissue such that treatment surface 2109 and active electrodes 2110 are positioned so as to contact, or be in close proximity to, the target tissue. Each of the plurality of active electrodes includes a loop portion adapted for ablating tissue via molecular dissociation of tissue components upon application of a high frequency voltage to the apparatus. In one embodiment, an electrically conductive fluid may be delivered to the distal end of the apparatus via a fluid delivery channel to provide a convenient current flow path between the active and return electrodes. A high frequency voltage is applied to the apparatus from a high frequency power supply to ablate the tissue at the target site. Suitable values for various voltage parameters are presented hereinabove.

Unwanted materials, such as low molecular weight ablation by-products, excess extraneously supplied fluid, resected tissue fragments, blood, etc., are conveniently removed from the target site via the integral aspiration unit of the invention. Typically, such an aspiration unit comprises an aspiration channel in communication with a distal aspiration port and a proximal aspiration tube, the latter coupled to a suitable vacuum source (not shown). Vacuum sources suitable for use in conjunction with apparatus and systems of the invention are well known in the art.

In one embodiment, the apparatus may be reciprocated or otherwise manipulated during application of the high frequency voltage, such that loop portion 2113 including distal face 2111 of each active electrode moves with respect to the target tissue, and the tissue in the region of each distal face 2111 is ablated via molecular dissociation of tissue components. The apparatus is capable of effectively removing tissue in a highly controlled manner, and is particularly useful in procedures requiring a smooth and/or contoured tissue surface.

Figure 29:
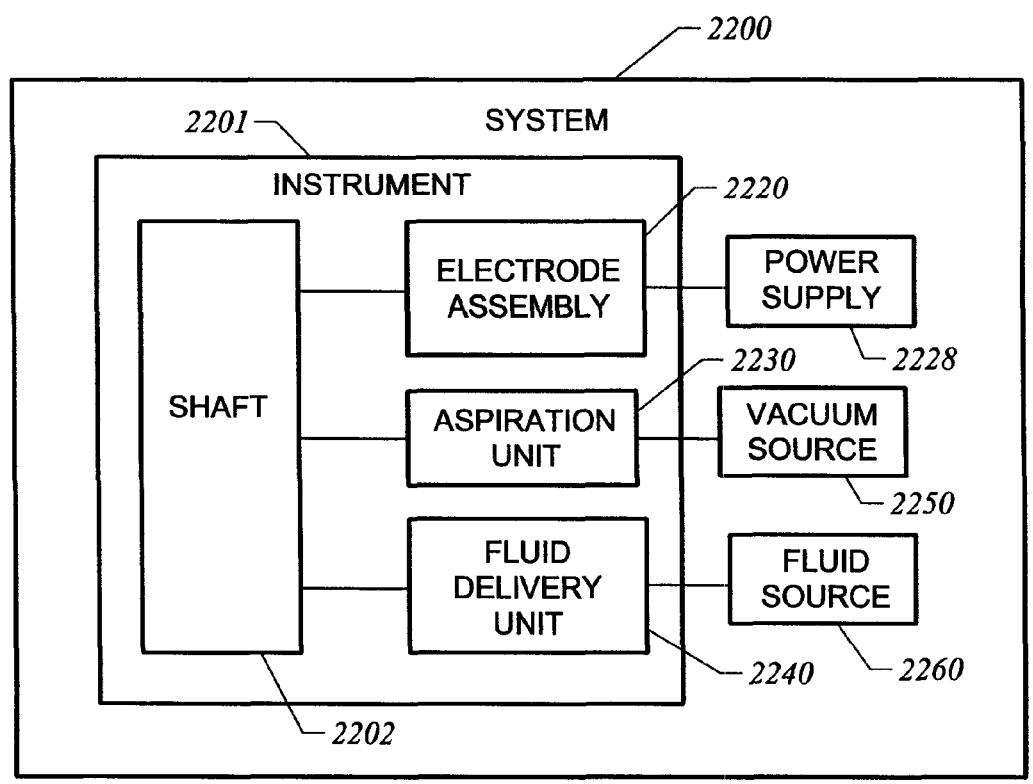
FIG. 29 is a block diagram schematically representing an electrosurgical system, according to one embodiment of the invention.

FIG. 29 is a block diagram schematically representing an electrosurgical system 2200, according to one embodiment of the invention. System 2200 includes an electrosurgical instrument 2201, such as a probe or catheter, including a shaft 2202 and an electrode assembly 2220. System 2200 further includes a high frequency power supply 2228 coupled to electrode assembly 2220. Typically, instrument 2201 further includes an aspiration unit 2230 and a fluid delivery unit 2240 coupled, respectively, to a vacuum source 2250 and a fluid source 2260. Aspiration unit 2230 is adapted for aspirating excess or unwanted materials from a working end of instrument 2201 or from a surgical site during a procedure. Fluid delivery unit 2240 is adapted for delivering an electrically conductive fluid to the working end of instrument 2201, or to a surgical site, during certain procedures.

Figure 30:
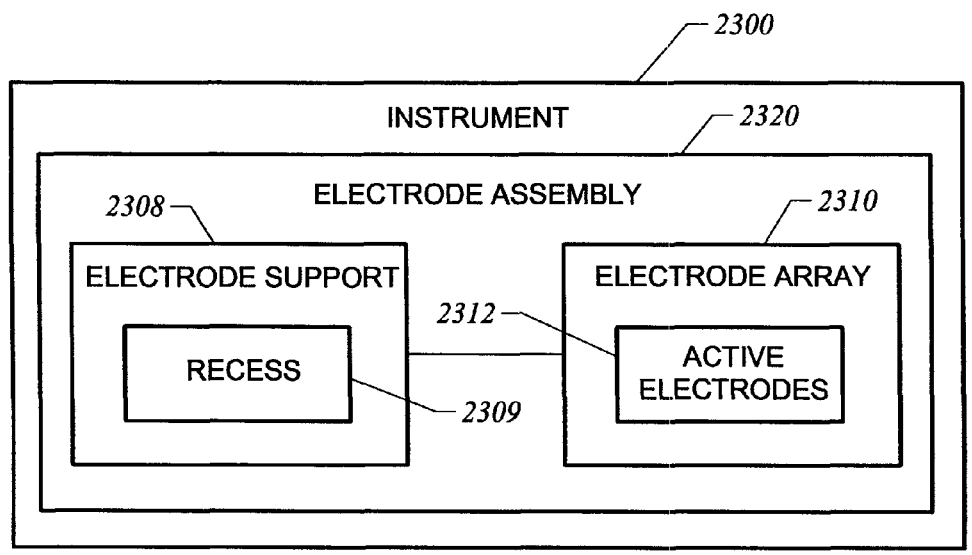
FIG. 30 is a block diagram schematically representing an electrosurgical instrument including an electrode assembly, according to one aspect of the invention.

FIG. 30 is a block diagram schematically representing an electrosurgical instrument 2300, according to another aspect of the invention. Instrument 2300 includes an electrode assembly 2320 comprising an electrode array 2310. In one embodiment, electrode assembly 2320 is disposed on an electrically insulating electrode support 2308. Electrode array 2310 includes a plurality of active electrodes 2312. Each active electrode 2312 is adapted for at least one of the following functions: i) localized ablation of a target tissue, ii) localized coagulation of a target tissue, and iii) digestion of resected tissue fragments. In one embodiment, electrode support 2308 comprises a ceramic, a glass, or a silicone rubber. According to one aspect of the invention, the electrode support includes a tissue treatment surface, and the plurality of active electrodes are arranged substantially parallel to each other on the treatment surface (e.g., FIGS. 35 and 37). Other configurations for the electrode assembly are also within the scope of the invention. According to one aspect of the invention, the electrode support includes a recess within the tissue treatment surface (e.g., FIGS. 34C and 34E).

Figure 31:
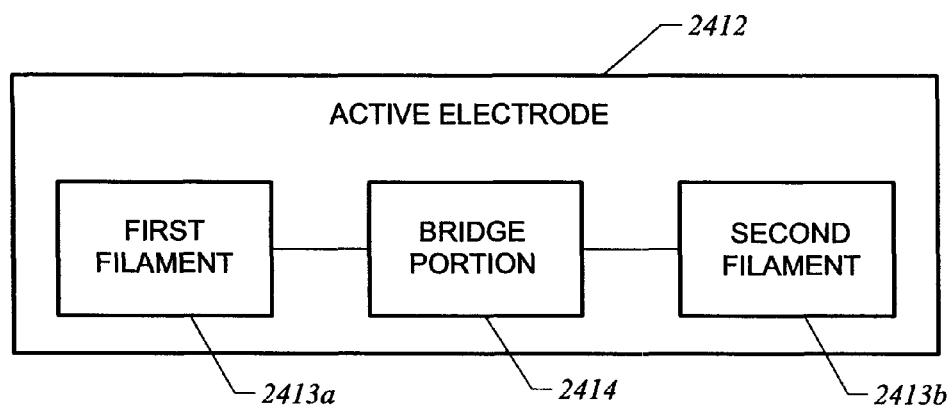
FIG. 31 is a block diagram schematically representing an active electrode for an electrosurgical instrument, according to another embodiment of the invention.

FIG. 31 is a block diagram schematically representing an active electrode 2412 for an electrosurgical instrument, according to another embodiment of the invention. Active electrode 2412 includes a first filament 2413a, a second filament 2413b, and a bridge portion 2414. Typically, bridge portion 2414 is suspended between first filament 2413a and second filament 2413b. According to one embodiment of the invention, the cross-sectional area of bridge portion 2414 is greater than that of either first filament 2413a or second filament 2413b. In one embodiment, the bridge portion includes a first distal face, and a second distal face contiguous with the first distal face to define a distal edge (e.g., FIGS. 34B-D). Typically, active electrode 2412 comprises a material such as stainless steel, molybdenum, platinum, tungsten, palladium, iridium, titanium, or their alloys.

Figure 32:
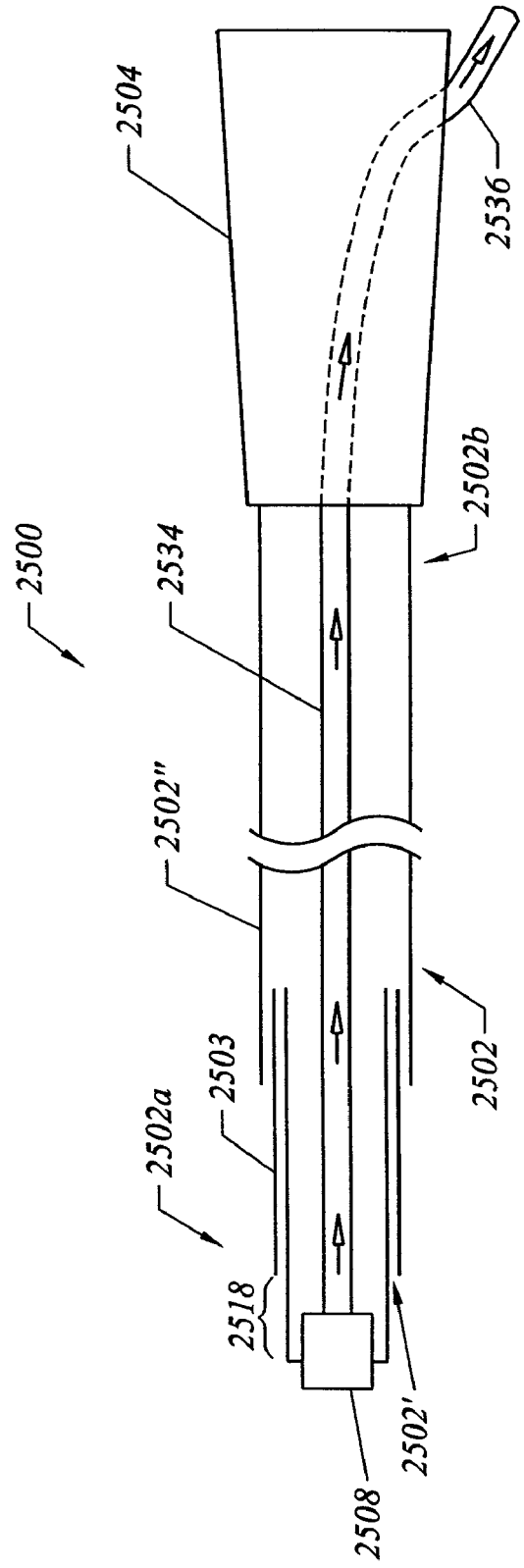
FIG. 32 schematically represents an electrosurgical instrument as seen in side view, according to another aspect of the invention.

FIG. 32 schematically represents an electrosurgical instrument or probe 2500 as seen in side view, according to another aspect of the invention. Electrosurgical instrument 2500 includes a shaft 2502, having a shaft distal end 2502a and a shaft proximal end 2502b, and a handle 2504 affixed to shaft proximal end 2502b. Shaft 2502 includes an inner shaft 2502' and an outer shaft 2502". A proximal portion of inner shaft 2502' is ensheathed within an electrically insulating sleeve or sheath 2503. In one embodiment, inner shaft 2502' comprises a metal tube, and an exposed distal portion of inner shaft 2502' defines a return electrode 2518. Inner shaft 2502' may comprise stainless steel, or the like, while sheath 2503 may comprise a heat shrink tube. Outer shaft 2502" may comprise an electrically insulating material, such as various resin-based composite materials, which may include a fibrous component. In one embodiment, outer shaft 2502" comprises a Polygon Tube™ (Polygon Company, Walkerton, Ind.).

Again with reference to FIG. 32, an electrically insulating electrode support or spacer 2508 is disposed at shaft distal end 2502a. Typically, at least one active electrode is disposed on electrode support 2508. (Active electrodes are omitted from FIG. 32, e.g., for the sake of clarity.) An aspiration lumen 2534 is disposed within shaft 2502. A distal end of aspiration lumen 2534 is coupled to a void in electrode support 2508 (e.g., FIGS. 34E, 35). A proximal end of aspiration lumen 2534 is coupled to an aspiration tube 2536. Aspiration lumen 2534 is adapted for removing unwanted materials from the working end of instrument 2500 via an aspiration stream (represented in FIG. 32 by open arrows). As shown in FIG. 32, aspiration tube 2536 extends from handle 2504, although other configurations are possible under the invention. In one embodiment, the aspiration lumen may be accommodated within a multi-lumen tube (not shown), wherein the multi-lumen tube lies longitudinally within shaft 2502. In one embodiment, the multi-lumen tube is formed as a plastic extrusion product, the latter well known in the art. Aspiration tube 2536 is adapted for coupling to a suitable vacuum source. Such vacuum sources are well known to the skilled artisan.

Figure 33A:
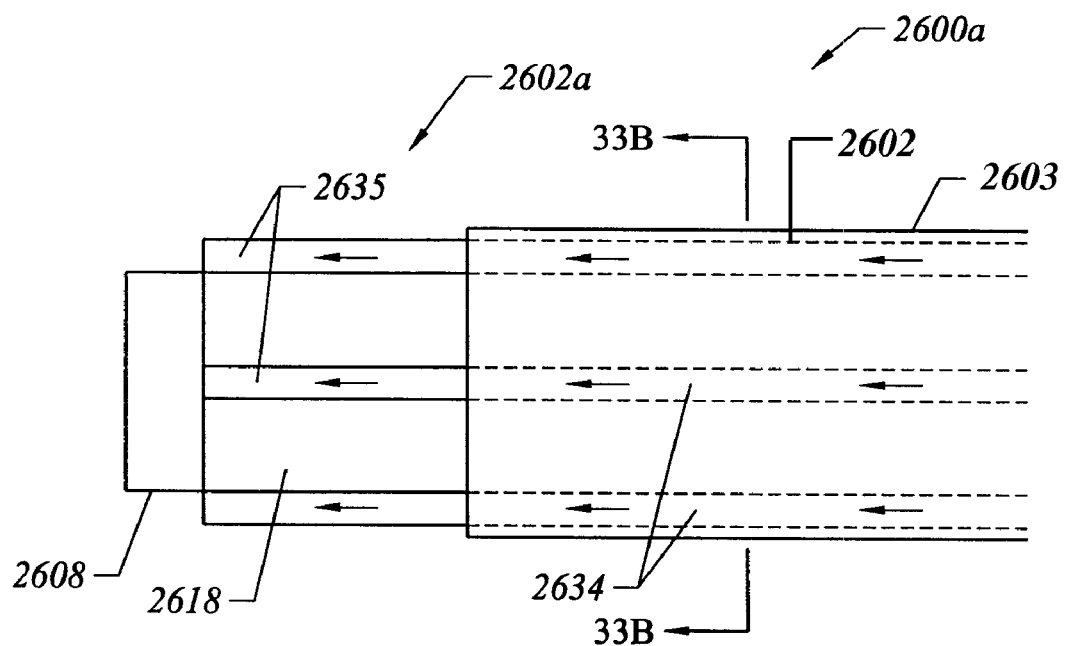
FIGS. 33A and 33B are a side view and a cross-sectional view, respectively, of the distal end portion of an electrosurgical instrument having a fluid delivery element, according to the invention.

FIG. 33A is a side view of the working or distal end 2600a of an electrosurgical instrument having a fluid delivery element, according to another aspect of the invention. A shaft 2602, e.g., comprising a metal tube, includes a plurality of external, longitudinal grooves 2635. An electrically insulating electrode support or spacer 2608 is disposed at a shaft distal end 2602a. Active electrodes (e.g., FIGS. 34A-D) are omitted from FIG. 33A for the sake of clarity. A portion of shaft 2602 is ensheathed within an electrically insulating sleeve or sheath 2603. A longitudinal void or fluid channel 2634 is defined jointly by each groove 2635 and an inner surface of sheath 2603. In one embodiment, grooves 2635 are restricted to a distal portion of the shaft. Each of the plurality of fluid channels 2634 may be coupled to a fluid source via a fluid delivery tube (e.g., FIGS. 15B, 25A), whereby an electrically conductive fluid, e.g., saline, may be delivered to working end 2600a in the vicinity of electrode support 2608. An exposed distal portion of shaft 2602 defines a return electrode 2618. Thus, grooves 2635 extend along return electrode 2618, whereby fluid may be delivered directly to return electrode 2618. In some embodiments, the distal end of the shaft may be curved (e.g., FIGS. 24A, 34B), and each groove may follow the contour or curve of the shaft.

Figure 33B:
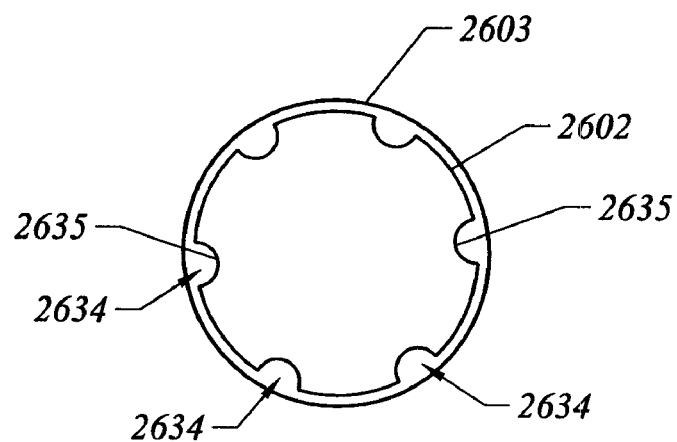

FIG. 33B is a cross-sectional view taken along the lines 23B-23B of FIG. 33A showing sheath 2603 ensheathing shaft 2602, a plurality of external grooves 2635 on shaft 2602, and a corresponding plurality of fluid channels 2634 between shaft 2602 and an internal surface of sheath 2603. In one embodiment, sheath 2603 comprises a heat shrink tube. Although FIG. 33B shows six external grooves/fluid delivery channels 2635/2634, other numbers and arrangements are also within the scope of the invention.

Figure 34A:
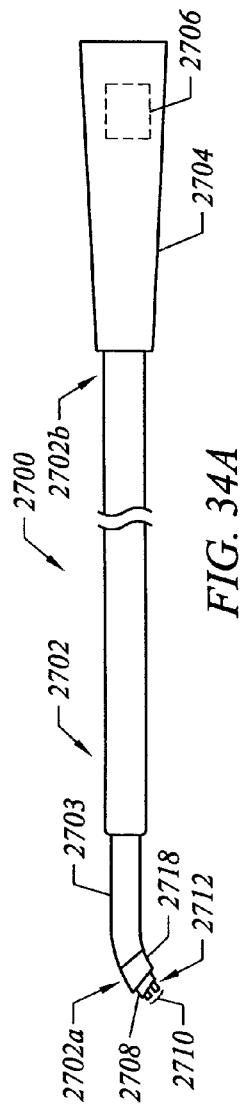
FIG. 34A is a side view of an electrosurgical instrument, according to one embodiment of the invention.

FIG. 34A is a side view of an electrosurgical instrument 2700, according to one embodiment of the invention. Instrument 2700 includes a shaft 2702, having a shaft distal end 2702a and a shaft proximal end 2702b, and a handle 2704 at shaft proximal end 2702b. A distal portion of shaft 2702 is ensheathed within an electrically insulating sleeve or sheath 2703. In one embodiment, sheath 2703 may comprise a heat shrink tube. An exposed (non-insulated) portion of shaft distal end 2702a defines a return electrode. In one embodiment, return electrode 2718 comprises an exposed, or naked, length of a metal tube or cylinder. In the embodiment shown in FIG. 34A, shaft distal end 2702a is curved.

Again with reference to FIG. 34A, an electrically insulating electrode support 2708 is disposed at shaft distal end 2702a. At least one active electrode 2712 is disposed on electrode support 2708. FIG. 34A shows an electrode array 2710 comprising two active electrodes 2712. However, electrode arrays having other numbers of active electrodes are also within the scope of the invention. Handle 2704 houses a connection block 2706. Each active electrode 2712 and return electrode 2718 are coupled to connection block 2706 via one or more electrode leads or filaments (e.g., FIG. 23C). Connection block 2706 permits the facile connection of active electrodes 2712 and return electrode 2718 to a high frequency power supply (e.g., FIGS. 1, 29). In one embodiment, each active electrode is independently coupled to a separate channel of the high frequency power supply.

Figure 34C:
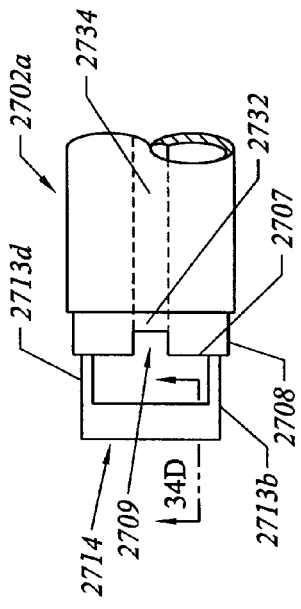
FIG. 34C shows the working end of the instrument, as seen along the lines 34C-34C of FIG. 34B.
Figure 34E:
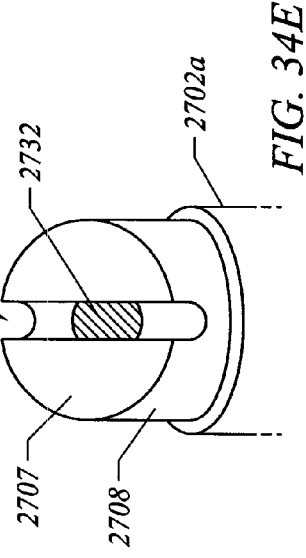
FIG. 34E is a perspective view of the working end of the instrument of FIG. 34A, with the electrode(s) omitted for the sake of clarity.
Figure 34B:
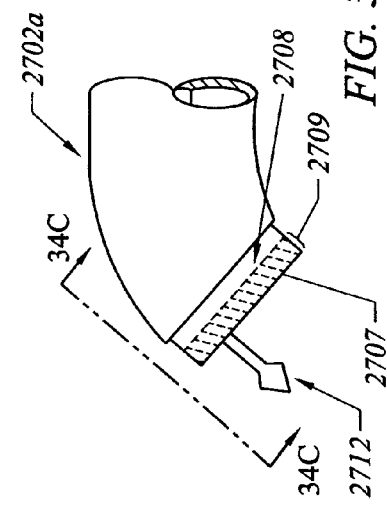
FIG. 34B is a side view of the working or distal end of the instrument of FIG. 34A.

FIG. 34B is a side view of the working or distal end of instrument 2700 of FIG. 34A, showing active electrode 2712 protruding from electrode support 2708. Only a single active electrode is shown in FIG. 34B, for the sake of clarity. Thus, the numbers of active electrodes shown in the Drawings should not be construed as limiting the invention. Electrode support 2708 includes a treatment surface 2707 and a recess 2709 within treatment surface 2707.

FIG. 34C shows the working end of instrument 2700 as seen along the lines 34C-34C of FIG. 34B. Each active electrode 2712 includes first and second filaments 2713a, 2713b extending from treatment surface 2707 of support 2708, and a bridge portion 2714 between first filament 2713a and second filament 2713b. Bridge portion 2714 is coupled to connection block 2706 (FIG. 34A) via at least one of first filament 2713a and second filament 2713b. Bridge portion 2714 is spaced from treatment surface 2707 by a minimum distance typically in the range of from about 0.05 to 3 mm. More typically, bridge portion 2714 is spaced from treatment surface 2707 by a distance not less than from about 0.1 to 2 mm. Bridge portion 2714 spans recess 2709. A void within recess 2709 defines an aspiration port 2732. Aspiration port 2732 is in communication proximally within an aspiration lumen 2734 within shaft 2702.

Figure 34D:
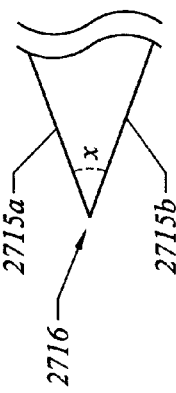
FIG. 34D shows a distal portion of the bridge portion of an active electrode as seen along the lines 34D-34D of FIG. 34C.

FIG. 34D shows a distal portion of bridge portion 2714 of active electrode 2712 as seen along the lines 34D-34D of FIG. 34C. Thus, bridge portion 2714 includes a first distal face 2715a and a second distal face 2715b contiguous with first distal face 2715a to define a distal edge 2716, wherein distal edge 2716 is characterized by angle x. Typically, angle x is an acute angle in the range of from about 25° to 85°. In one embodiment, angle x is in the range of from about 30° to 65°. Each active electrode 2712 may have one or more other edges in addition to distal edge 2716. While not being bound by theory, applicant believes that the presence of edge(s) on the active electrode(s) generates relatively high current densities and promotes formation of a plasma in the vicinity of the active electrode(s) upon application of a high frequency voltage between the active electrode(s) and the return electrode.

FIG. 34E is a perspective view of the working end of instrument 2700 of FIG. 34A, showing the location of recess 2709 with respect to treatment surface 2707, as well as the location of aspiration port 2732 within recess 2709. In the embodiment shown in FIG. 34E, treatment surface 2707 is substantially planar, recess 2709 is substantially linear and bisects treatment surface 2707, while aspiration port 2732 is substantially centrally located within recess 2709. However, other configurations and locations for these elements are also within the scope of the invention. The active electrode(s) are omitted from FIG. 34E for the sake of clarity.

Figure 35:
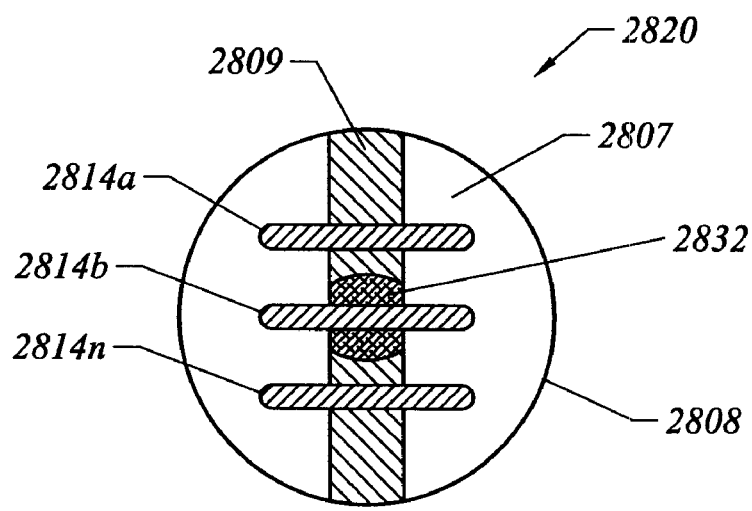
FIG. 35 is a face view of an electrode assembly of an electrosurgical instrument illustrating the configuration of a plurality of active electrodes in relation to an electrode support, according to another embodiment of the invention.

FIG. 35 is a face view of an electrode assembly 2820 of an electrosurgical instrument, illustrating the configuration of a plurality of active electrodes on an electrode support 2808, each active electrode including a bridge portion, 2814a-n. Electrode support 2808 includes a treatment surface 2807 and a recess 2809. Bridge portions 2814a, 2814b, 2814n are arranged substantially parallel to each other on treatment surface 2707. Each bridge portion 2814a, 2814b, 2814n spans recess 2809 and is arranged substantially orthogonal thereto. An aspiration port 2832 is located within recess 2809. In the embodiment shown in FIG. 35, bridge portion 2814b spans aspiration port 2832. Although FIG. 35 shows three parallel active electrodes, other numbers and configurations of active electrodes are also within the scope of the invention.

Figure 36:
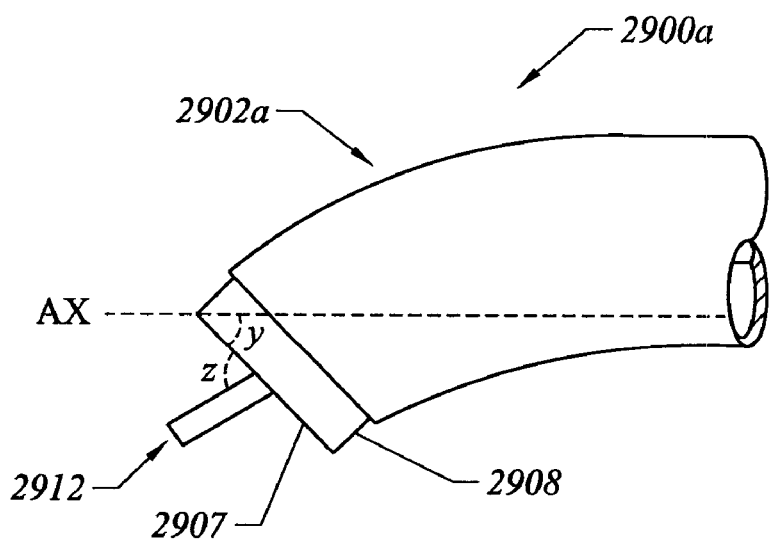
FIG. 36 is a side view of a working or distal end of an electrosurgical instrument showing an active electrode protruding from a surface of an electrode support, according to another embodiment of the invention.

FIG. 36 is a side view of a working or distal end 2900a of an electrosurgical instrument, including a shaft distal end 2902a and an electrode support 2908 disposed at shaft distal end 2902a. Electrode support 2908 includes a treatment surface 2907 arranged at an angle, y with respect to the longitudinal axis, AX of the instrument. In one embodiment, angle γ is in the range of from about 25° to 75°, and often from about 30° to 60°. An active electrode 2912 extends distally from electrode support 2908 at an angle, z with respect to treatment surface 2907. In one embodiment, angle z is in the range of from about 35° to 95°, and in some instances from about 60° to 85°. For the sake of clarity, a single active electrode 2912 is schematically represented in FIG. 36 as a rectangular shape. Instruments of the invention may feature active electrodes having various geometries, e.g., as described hereinabove.

Figure 37:
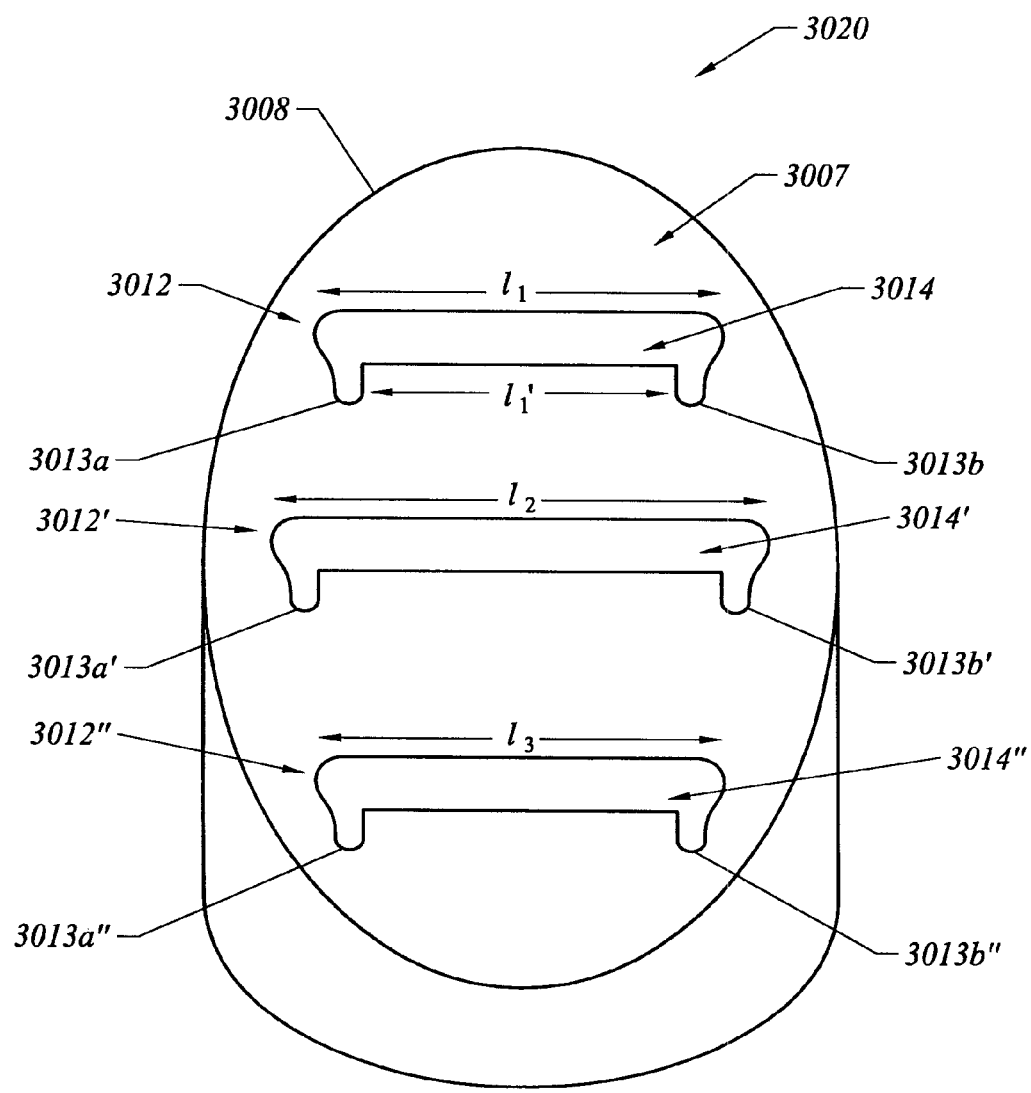
FIG. 37 is a perspective view of an electrode support of an electrosurgical instrument, showing a plurality of active electrodes on a treatment surface of the electrode support.

FIG. 37 is a perspective view of an electrode assembly 3020 for an electrosurgical instrument, according to one embodiment of the invention. Electrode assembly 3020 includes first, second, and third active electrodes 3012, 3012', and 3012" arranged parallel to each other on a treatment surface 3007 of an electrode support 3008. As shown, treatment surface 3007 is substantially planar. First, second, and third active electrodes 3012, 3012', and 3012" each comprise a first filament 3013a, 3013a', and 3013a", respectively; a second filament 3013b, 3013b', and 3013b", respectively; and a bridge portion 3014, 3014', and 3014", respectively. In one embodiment, each bridge portion is arranged substantially orthogonal to both the first and second filaments, and each bridge portion is oriented in substantially the same direction. Bridge portions 3014, 3014', and 3014", have lengths represented as $l_1$, $l_2$, and $l_3$, respectively. As shown in FIG. 37, $l_1$ is approximately the same as $l_3$, while $l_2$ is greater than $l_1$ and $l_3$. In one embodiment, the distance between the first and second filaments of an active electrode (e.g., electrode 3012) is less than the length of the corresponding bridge portion. Thus, the distance 11' between first and second filaments 3013a, 3013b is less than the length $l_1$ of bridge portion 3014. Typically, each pair of filaments, e.g., first and second filaments 3013a, 3013b, extend through a corresponding pair of electrode ports (not shown) located within support 3008.

Figure 38:
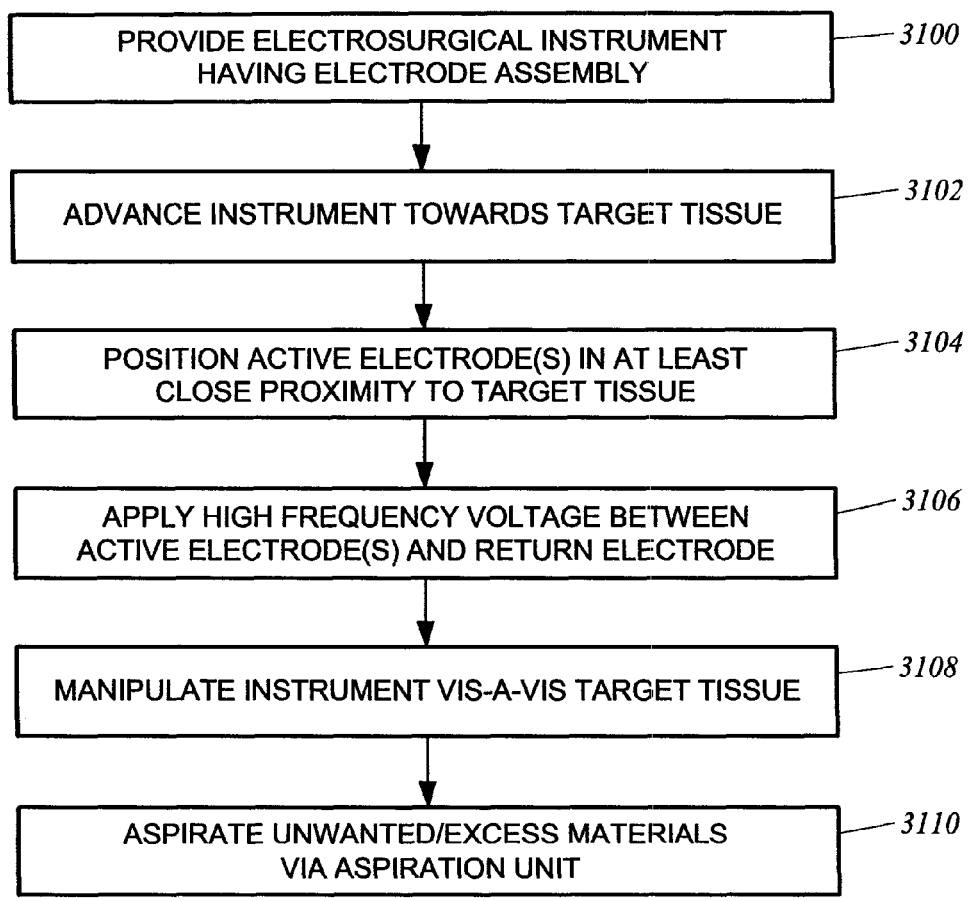
FIG. 38 schematically represents a series of steps involved in a method of treating a target tissue during a surgical procedure, according to another embodiment of the invention.

FIG. 38 schematically represents a series of steps involved in a method of treating a target tissue during a surgical procedure, according to another embodiment of the invention, wherein step 3100 involves providing an electrosurgical instrument or probe adapted for treating the target tissue. In one embodiment, an instrument provided in step 3100 is adapted for the controlled ablation of the target tissue, as well as spot coagulation of tissue, and the digestion of resected tissue fragments. Electrosurgical instruments of step 3100 may have certain elements, features, and characteristics of various embodiments of the invention described hereinabove. In one embodiment, an instrument provided in step 3100 includes a distal or working end, and an electrode assembly disposed at the working end, wherein the electrode assembly comprises at least one active electrode disposed on an electrically insulating electrode support. According to one aspect of the invention, an instrument of step 3100 is adapted for the controlled removal of soft tissue during laparoscopic procedures. In one embodiment, such an instrument is adapted for the controlled removal and/or coagulation of ectopic endometrial lesions or implants. In use, instruments of the invention are coupled to a high frequency power supply (e.g., FIG. 1) adapted for operation in the ablation mode or the sub-ablation mode. In one embodiment, the instrument has a curved working end (e.g., FIG. 34A).

Step 3102 involves advancing the working end of the instrument towards a target tissue. In one embodiment, the instrument is advanced towards the target tissue via a laparoscope. In one embodiment, the instrument is adapted for advancement through a 5 mm cannula. Step 3104 involves positioning the electrode assembly in at least close proximity to the target tissue, e.g., such that at least one active electrode is in contact with, or adjacent to, the target tissue. As an example, the target tissue may be an endometrial implant located on the bowel, the ovaries, the urinary bladder, or the ureter of a patient.

Step 3106 involves applying a high frequency voltage between the active electrode(s) and a return electrode, in either the ablation mode or the sub-ablation mode, such that the target tissue is ablated (e.g., via Coblation®), or coagulated (sub-ablation mode). The parameters of the applied voltage are typically within the ranges cited hereinabove, e.g., in the range of from about 200 volts RMS to 1000 volts RMS in the ablation mode, and in the range of from about 10 volts RMS to 150 volts RMS in the sub-ablation mode. In one embodiment, the return electrode is integral with the probe, and comprises a non-insulated portion of a metal tube located proximal to the active electrode(s). During and/or prior to step 3106, an electrically conductive fluid, such as isotonic saline, may be delivered to the working end of the instrument, or to the target tissue, via a fluid delivery element integral with the instrument. Such fluid may provide a current flow path between the active electrode(s) and the return electrode.

Optional step 3108 involves manipulating the instrument such that the electrode assembly is translated with respect to the target tissue. In one embodiment, the electrode assembly is positioned according to step 3104, and thereafter the instrument is manipulated such that the active electrode(s) repeatedly move over the target tissue in a smooth "brushing" motion, whereby target tissue is selectively removed with little or no collateral damage to underlying tissue. Removal of target tissue (e.g., abnormal tissue, such as neoplasms, or ectopic endometrial tissue) according to the invention may result in the formation of gaseous by-products and, in some instances, resected fragments of target tissue. It is generally advantageous to remove such ablation by-products and resected tissue fragments from the surgical site. To this end, the instrument is typically adapted for aspirating unwanted or excess materials, including gaseous ablation by-products, from the surgical site. Step 3110 involves aspirating such unwanted or excess materials from the surgical site, or from the working end of the instrument; via an aspiration unit which may be integral with the instrument. In some embodiments, the active electrode(s) are adapted for digesting tissue fragments to form smaller fragments and/or gaseous ablation by-products, thereby preventing blockage of the aspiration unit by larger tissue fragments.

Instruments of the invention may be used during a broad range of laparoscopic procedures, including the removal or coagulation of endometrial tissue from the bowel, ovaries, ureter, urinary bladder, or other sites of the abdominal cavity, including ablation of endometriomas, as well as appendectomies, and the removal of fibroid tumors, and the like.

Other modifications and variations can be made to the disclosed embodiments without departing from the subject invention. For example, other numbers and arrangements of the active electrodes on the electrode support are possible, under the invention. In addition, certain elements or features of various disclosed embodiments may be substituted for corresponding or analogous elements or features of other disclosed embodiments, or may be combined with elements and features of other disclosed embodiments, as will be apparent to the skilled artisan. Therefore, while certain embodiments of the present invention have been described in detail, by way of example and for clarity of understanding, a variety of changes, adaptations, and modifications will be obvious to those of skill in the art. Therefore, the scope of the present invention is limited solely by the appended claims.

What is claimed is:

1. An electrosurgical apparatus for treating tissue at a target site, comprising:
   a shaft having a shaft distal end and a shaft proximal end;
   an electrically insulating electrode support disposed at the shaft distal end;
   a plurality of active electrodes arranged substantially parallel to each other on the electrode support, wherein the shaft comprises an inner shaft and an outer sheath, wherein a proximal portion of the inner shaft lies within the outer sheath, and a distal portion of the inner shaft extends distally from the outer sheath; and
   wherein the distal portion of the inner shaft is exposed and comprises a return electrode spaced proximal from the plurality of active electrodes.

2. The apparatus of claim 1, wherein the inner shaft comprises a metal tube.

3. The apparatus of claim 2, wherein the metal tube comprises stainless steel.

4. The apparatus of claim 2, wherein the metal tube has a curved distal end.

5. The apparatus of claim 1, wherein the outer sheath comprises an electrically insulating tube.

6. The apparatus of claim 1, the outer sheath further comprising an electrically insulating sleeve ensheathing a length of the inner shaft, wherein the inner shaft includes at least one longitudinal, external groove.

7. The apparatus of claim 1, wherein the return electrode comprises a plurality of external, longitudinal grooves.

8. The apparatus of claim 1, further comprising a fluid delivery unit, wherein the fluid delivery unit is fluidly coupled to the shaft for delivering an electrically conductive fluid to the shaft distal end.

9. The apparatus of claim 8, wherein the fluid delivery unit comprises a plurality of fluid delivery channels, each fluid delivery channel defined jointly by an external groove in the inner shaft and an inner surface of the outer sheath, wherein the outer sheath comprises an electrically insulating sleeve ensheathing a length of the inner shaft.

10. The apparatus of claim 1, wherein each of the plurality of active electrodes comprises a first filament, a second filament, and a bridge portion suspended between the first filament and the second filament.

11. The apparatus of claim 10, wherein the electrode support includes a substantially planar treatment surface, and wherein each bridge portion is spaced from the treatment surface by a minimum distance in the range of from about 0.05 mm to 3 mm.

12. The apparatus of claim 10, wherein the electrode support includes a treatment surface and a recess within the treatment surface, and each bridge portion spans the recess.

13. The apparatus of claim 12, wherein the treatment surface is bisected by the recess.

14. The apparatus of claim 12, further comprising an aspiration unit adapted for aspirating excess or unwanted materials from a working end of the apparatus or from a surgical site.

15. The apparatus of claim 14, wherein the aspiration unit includes an aspiration port, and wherein the aspiration port lies within the recess.

16. The apparatus of claim 1, wherein each of the plurality of active electrodes including a distal edge, wherein the distal edge is characterized by an acute angle in the range of from about 25° to 85°.

17. The apparatus of claim 1, wherein the electrode support comprises a ceramic.

18. The apparatus of claim 1, further comprising a connection block adapted for coupling the plurality of active electrodes to a high frequency power supply, wherein each of the plurality of active electrodes comprises a bridge portion, a first filament, and a second filament, and wherein at least one of the first filament and the second filament is coupled to the connection block.

19. An electrosurgical instrument, comprising:
a shaft having a shaft distal end, the shaft distal end having a plurality of longitudinal, external grooves;
an electrode assembly disposed at the shaft distal end; and
an electrically insulating sheath external to the shaft distal end, the sheath and the plurality of grooves jointly defining a corresponding plurality of fluid delivery channels external to the shaft distal end, each of the plurality of fluid delivery channels adapted as a fluid conduit.

20. The instrument of claim 19, wherein the electrically insulating sheath comprises a heat shrink tube.

21. The instrument of claim 19, wherein the electrode assembly comprises an electrically insulating electrode support having a treatment surface, and at least one active electrode disposed on the treatment surface.

22. The instrument of claim 21, wherein each active electrode includes a distal edge, each distal edge characterized as having an acute angle.

23. The instrument of claim 19, wherein the shaft distal end is curved.

* * * * *